United States Patent
Brinkmann et al.

(10) Patent No.: US 9,303,075 B2
(45) Date of Patent: Apr. 5, 2016

(54) CELL-PENETRATING PEPTIDES AND USES THEREOF

(71) Applicant: Hoffmann-La Roche Inc., Nutley, NJ (US)

(72) Inventors: Ulrich Brinkmann, Weilheim (DE); Alexander Haas, Munich (DE); Daniela Maisel, Penzberg (DE)

(73) Assignee: HOFFMANN-LA ROCHE INC., Nutley, NJ (US)

(*) Notice: Subject to any disclaimer, the term of this patent is extended or adjusted under 35 U.S.C. 154(b) by 0 days.

(21) Appl. No.: 13/712,088

(22) Filed: Dec. 12, 2012

(65) Prior Publication Data

US 2013/0164219 A1    Jun. 27, 2013

Related U.S. Application Data

(63) Continuation of application No. PCT/EP2011/059853, filed on Jun. 14, 2011.

(30) Foreign Application Priority Data

Jun. 14, 2010  (EP) .................................... 10165793
Dec. 15, 2010  (EP) .................................... 10195278

(51) Int. Cl.
| | |
|---|---|
| *C07K 14/435* | (2006.01) |
| *C07K 1/107* | (2006.01) |
| *C07K 14/47* | (2006.01) |
| *C07K 14/00* | (2006.01) |
| *A61K 47/48* | (2006.01) |

(52) U.S. Cl.
CPC ........... *C07K 14/47* (2013.01); *A61K 47/48323* (2013.01); *C07K 1/1075* (2013.01); *C07K 1/1077* (2013.01); *C07K 14/00* (2013.01); *C07K 14/435* (2013.01)

(58) Field of Classification Search
None
See application file for complete search history.

(56) References Cited

U.S. PATENT DOCUMENTS

| 7,015,311 B1 | 3/2006 | Johnson et al. |
|---|---|---|
| 7,067,473 B1 | 6/2006 | Masure |
| 7,173,007 B1 | 2/2007 | Zaiou et al. |

FOREIGN PATENT DOCUMENTS

| WO | 97/08196 A1 | 3/1997 |
|---|---|---|
| WO | 03/106491 A2 | 12/2003 |
| WO | 2007/069068 A2 | 6/2007 |
| WO | 2011/003557 A1 | 1/2011 |
| WO | 2011/003557 A8 | 1/2011 |
| WO | WO 2011003780 A1 * | 1/2011 |

OTHER PUBLICATIONS

Uniprot. ASM3B_HUMAN, B4DEC6_HUMAN.*
Examination Report issued in the corresponding European Patent Application No. 11729276.3, pp. 1-7 (Issued Apr. 2, 2014).
Office Action issued in the corresponding Chinese Patent Application No. 201180029464.X (Issued Feb. 17, 2014), pp. 1-10, with English Translation in 9 pages.
PCT/EP2011/059853 International Search Report., pp. 1-8 (published Feb. 23, 2012).
Fonseca, S.B. et al., "Recent advanced in the use of cell-penetrating peptides for medical and biological applications" Advanced Drug Delivery Reviews 61(11):953-964 (Sep. 30, 2009).
Green, M. et al., "Autonomous functional domains of chemically synthesized human immunodeficiency virus tat trans-activator protein" Cell 55(6):1179-1188 (Dec. 23, 1988).
Heitz, F. et al., "Twenty years of cell-penetrating peptides: from molecular mechanisms to therapeutics" British Journal of Pharmacology 157(2):195-206 (Mar. 20, 2009).
Human cathelin-like protein, CAP18/LL-37 protein fragment (aa:132-170), XP002604128, retrieved from EBI accession No. GSP:AEV74707, p. 1 (May 31, 2007).
Snyder, E.L. et al., "Recent advances in the use of protein transduction domains for the delivery of peptides, proteins and nucleic acids in vivo" Expert Opinion on Drug Delivery 2(1):43-51 (Jan. 1, 2005).
Decision to Grant Patent issued in Japanese Patent Application No. 2013-514688, dated Mar. 26, 2015, in 3 pages.
Haas et al., "Human-protein-derived peptides for intracellular delivery of biomolecules", Biochem. J., 442:583-593 (2012).
2nd Office Action issued in Chinese Patent Application No. 201180029464.X, dated Jan. 4, 2015, with English Translation (total in 9 pages).
Altschul et al., "Basic local alignment search tool" J. Mol. Biol. 215:403-410 (1990).
Lipman et al., "Rapid and sensitive protein similarity searches" Science 227:1435-1441 (1985).
Smith et al., "Identification of common molecular subsequences" J. Mol. Biol. 147:195-197 (1981).
El-Andaloussi et al., "Cargo-dependent cytotoxicity and delivery efficacy of cell-penetrating peptides: a comparative study" Biochem. J. 407:285-292 (2007).
Further Examination Report issed in New Zealand Patent Application No. 603732, issued on Jan. 12, 2015 (in 3 pages).

* cited by examiner

*Primary Examiner* — Amber D Steele
*Assistant Examiner* — Schuyler Milton
(74) *Attorney, Agent, or Firm* — Scott L. Ausenhus

(57) ABSTRACT

The present invention relates to the identification and functional characterization of human cell-penetrating peptides (CPPs) and their use; in particular as transfection vehicles.

29 Claims, 16 Drawing Sheets

Fig. 7
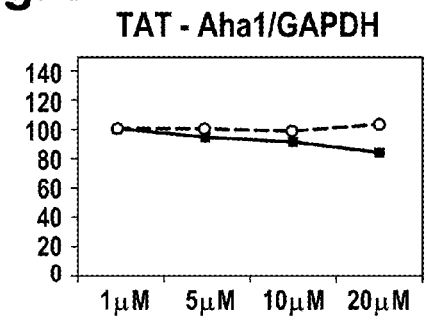
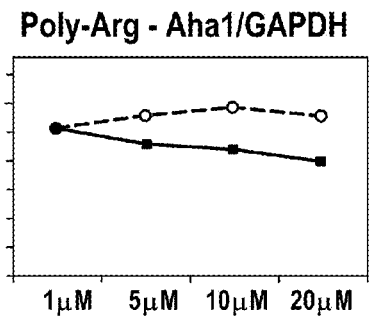
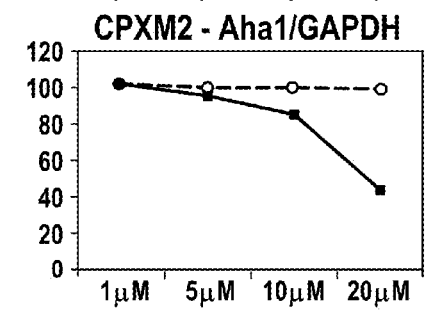
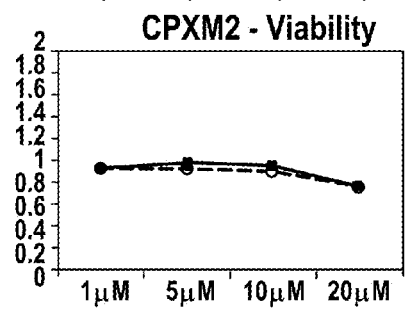
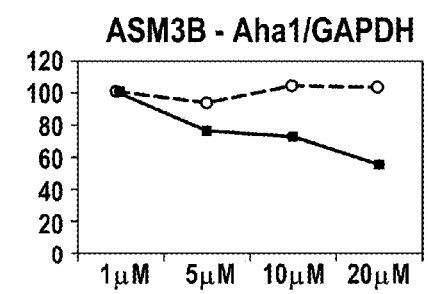
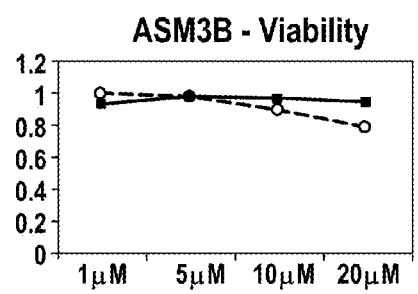
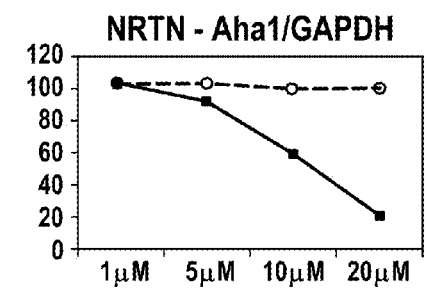
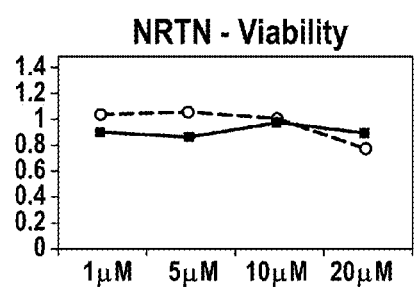
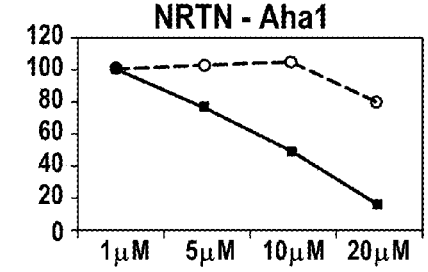
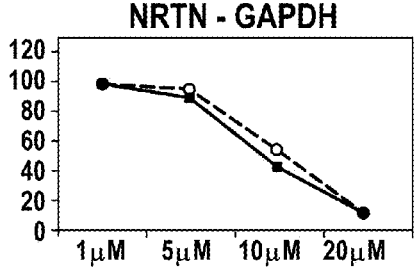

Fig. 11
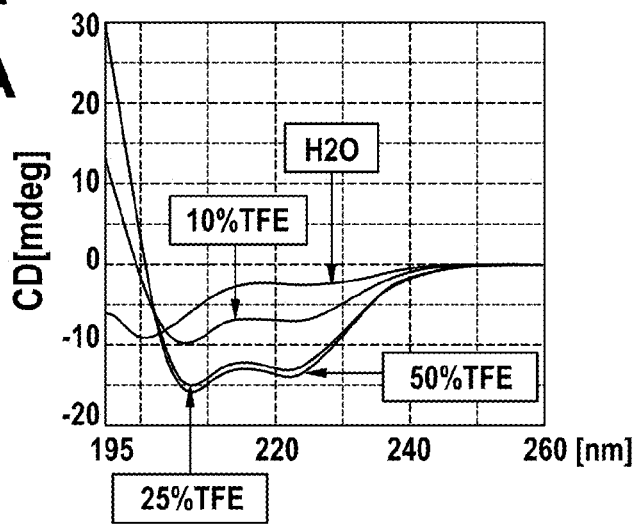
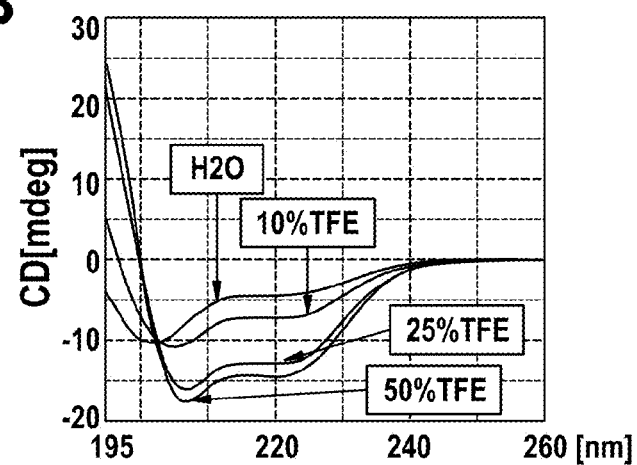
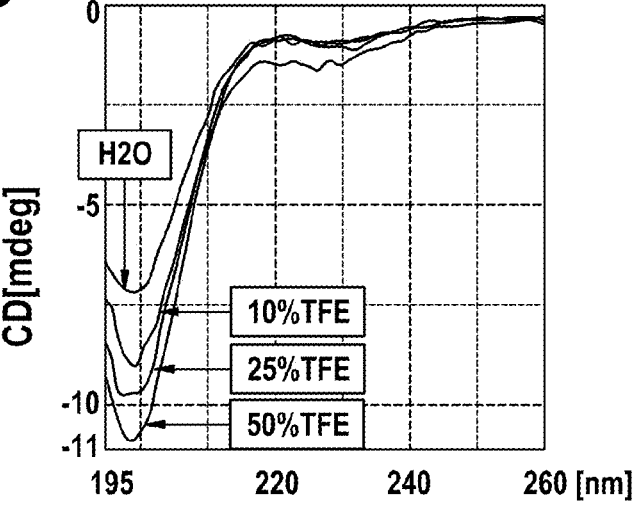

Fig. 12
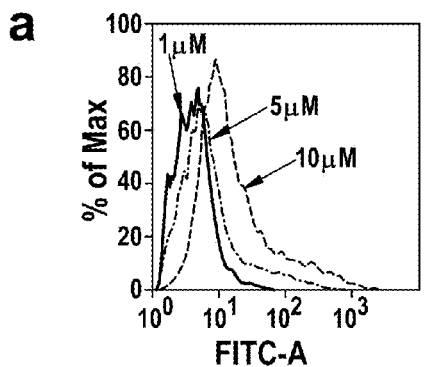
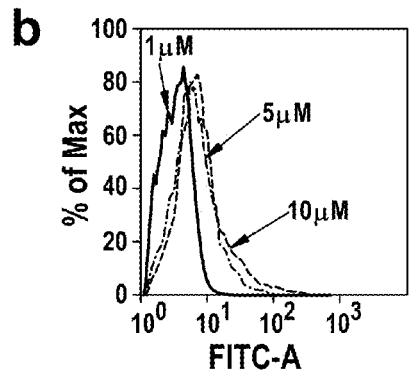
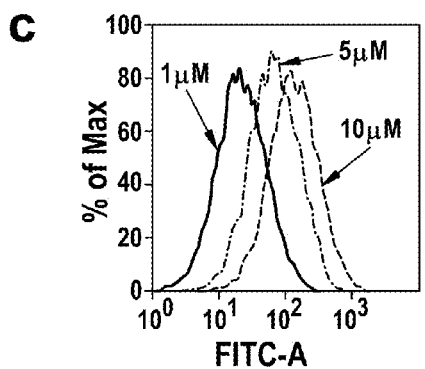
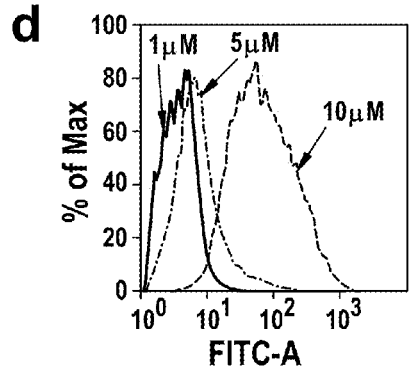

FITC-NRTN NRTN-FITC

Nor/Nur ● FSRSLHSLLVDL

NRTN ■ GAAEAAARVYDLGLRRLRQRRRLRRERVRA

NurNRTN ▲ FSRSLHSLLYDLGLRRLRQRRRLRRERVRA

BCL2-conversion functionalitiy

CPP functionalitiy

Fig. 16
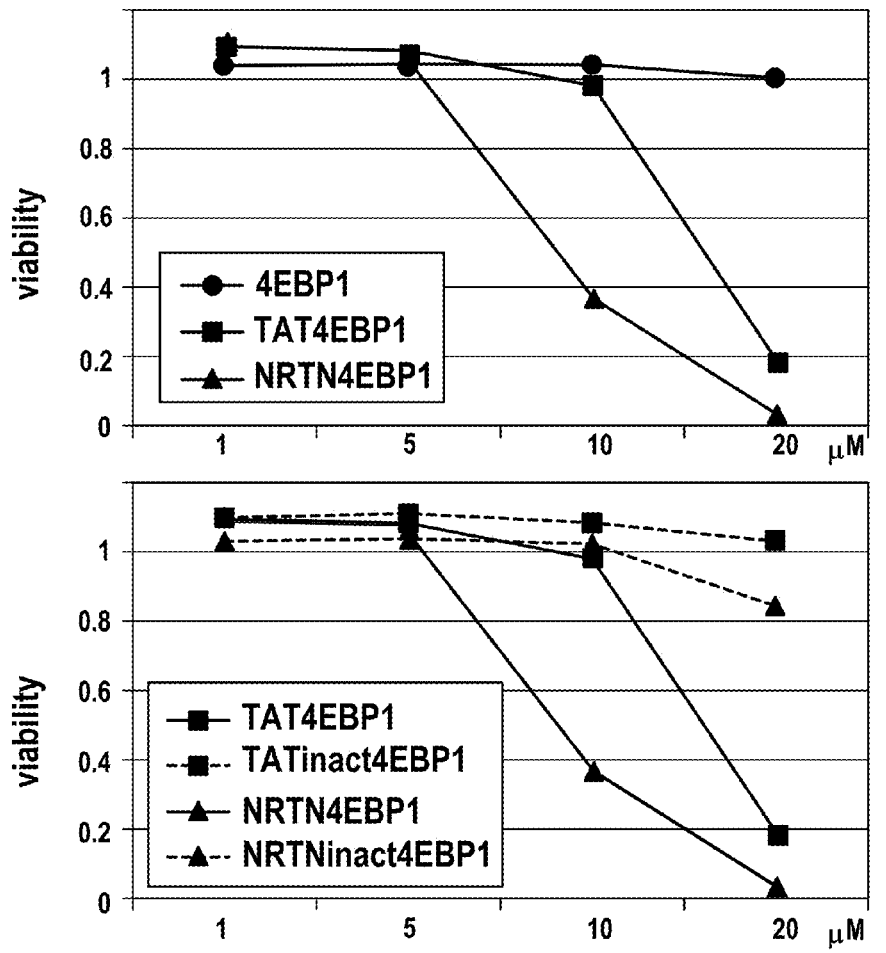
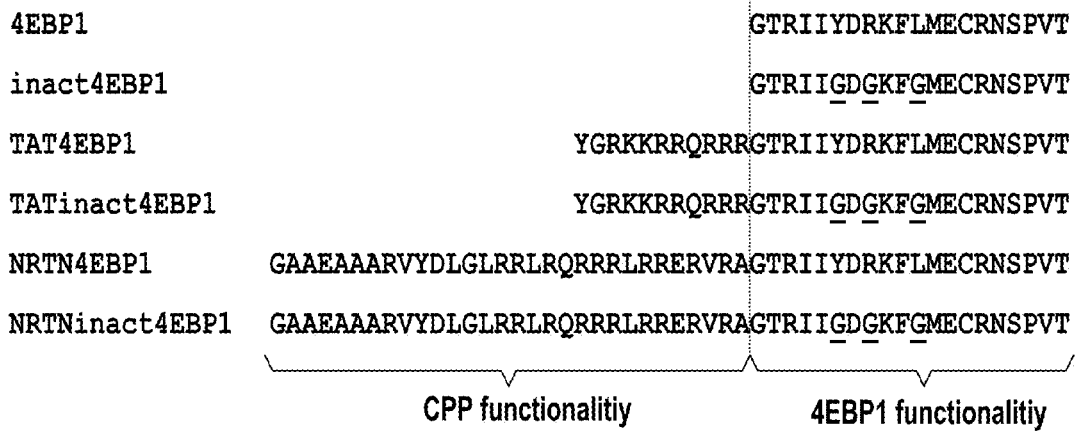

CELL-PENETRATING PEPTIDES AND USES THEREOF

CROSS-REFERENCE TO RELATED APPLICATION

This application is a continuation of International Application No. PCT/EP2011/059853 having an international filing date of Jun. 14, 2011, the entire contents of which are incorporated herein by reference, and which claims benefit under 35 U.S.C. §119 to European Patent Application Nos. 10165793.0 filed Jun. 14, 2010 and Ser. No. 10/195,278.6 filed on Dec. 15, 2010.

SEQUENCE LISTING

The instant application contains a Sequence Listing submitted via EFS-Web and hereby incorporated by reference in its entirety. Said ASCII copy, created on Dec. 6, 2012, is named P4983SequenceList.txt, and is 27,535 bytes in size.

FIELD OF THE INVENTION

The present invention relates to the identification and functional characterization of human cell-penetrating peptides (CPPs) and their use, in particular as transfection vehicles.

BACKGROUND

The cell plasma membrane represents an efficient barrier that prevents most molecules that are not actively imported from cellular uptake, thus also hampering the targeted delivery of therapeutic substances. Only a small range of molecules having a particular molecular weight, polarity and/or net charge is able to (passively) diffuse through cell membranes. All other molecules have to be actively transported, e.g., by receptor-mediated endocytosis or via ATP-binding transporter molecules. In addition, molecules may also artificially be forced to pass the cell membrane, for example by means of electroporation, cationic lipids/liposomes, microinjection, viral delivery or encapsulation in polymers. However, these methods are mainly utilized to deliver hydrophobic molecules. Furthermore, the significant side effects associated with these methods and the fact that their applicability is mostly limited to in vitro uses has prevented them from becoming an efficient tool for the delivery of drugs or other therapeutically active agents to cells in order to prevent or treat medical conditions.

In particular, the requirement of targeted delivery has also turned out to represent a major challenge in the development of RNAi (RNA interference)-based drugs. Such agents comprise small RNA molecules (e.g., siRNAs, miRNAs or shRNAs) that interfere with the expression of disease-causing or disease-promoting genes. Following the demonstration of RNAi in mammalian cells in 2001 (Elbashir, S. M. et al. (2001) Nature 411, 494-498), it was quickly realized that this sequence-specific mechanism of posttranscriptional gene silencing might be harnessed to develop a new class of medicaments that might also be a promising means for the treatment of diseases not accessible to therapeutic intervention so far (De Fougerolles, A. et al. (2007) Nat. Rev. Drug Discov. 6, 443-453).

However, as RNAi takes place in the cytosol any RNA-based drugs have to pass the cell membrane in order to exert their therapeutic effect. Several methods have been described so far in order to accomplish this goal such as the use of lipids (Schroeder; A. et al. (2010) J. Intern. Med. 267, 9-21), viral carriers (Liu, Y. P: and Berkhout, B. (2009) Curr. Top. Med. Chem. 9, 1130-1143), and polycationic nanoparticles (Howard, K. A. (2009) Adv. Drug Deliv. Rev. 61, 710-720).

Another method for the translocation of molecules through the cell membrane is the use of cell penetrating peptides (CPPs) (also referred to as protein transduction domains (PTDs) or membrane translocation sequences (MTS); reviewed, e.g., in Fonseca, S. B et al. (2009) Adv. Drug Deliv. Rev. 61, 953-964; Heitz, F. et al. (2009) Br. J. Pharmacol. 157, 195-206).

CPPs are a heterogeneous group of peptide molecules—both in terms of their primary amino acid sequences and their structures. Prominent examples of CPPs include the HIV-1 TAT translocation domain (Green; M. and Loewenstein, P. M. (1988) Cell 55, 1179-1188) and the homeodomain of the Antennapedia protein from Drosophila (Joliot; A. et al. (1991) Proc. Natl. Acad. Sci. USA 88, 1864-1868). The exact translocation mechanism is still disputed.

Mutation studies of the Antennapedia protein revealed that a sequence of 16 amino acids called penetratin or pAntp (Derossi, D. et al. (1994) J. Biol. Chem. 269, 10444-10450) is necessary and sufficient for membrane translocation. In the following, other protein-derived CPPs were developed such as the basic sequence of the HIV-1 Tat protein (Vives, E. et al. (1997) J. Biol. Chem. 272, 16010-16017). A synthetic peptide developed is the amphipathic model peptide MAP (Oehlke, J. et al. (1998) Biochim. Biophys. Acta 1414, 127-139).

Coupling of antisense DNA or peptide nucleic acids (PNAs) to CPPs was shown to exert the desired effect in vivo. However, it is still questioned which features were necessary for a CPP to exert its translocation function. In general, little sequence and/or structural resemblance has been found between the different CPPs. So far, the only consistently present feature is the rather high content of basic (positively charged) amino acids resulting in a positive net charge. Thus, it is assumed that CPPs initially bind to negatively charged head groups of lipids or proteins (proteoglycans) in the cell membrane. Once bound, however, the peptides are still inside membrane bound compartments. The further mechanism of uptake is still a matter of extensive debate. It has been proposed that CPPS are either "retrogradely" transported to the ER where they enter the cellular translocation machinery (Fischer, R. et al. (2004) J. Biol. Chem. 279, 12625-12635) or that they directly translocate across the membrane (Rothbard, J. B. et al. (2005) Adv. Drug Deliv. Rev. 57, 495-504). Depending on the mechanism of internalization known CPPs mainly localize in the nucleus or, in case they are internalized in vesicles, mainly remain inside these vesicles, and only a small portion is released into the cytoplasm.

Many CPPs have severe side effects on the cells applied, which is understandable in view of the fact that most of the proteins from which the CPPs are derived function as, e.g., antimicrobial substances or toxins. For example, CPPs can cause cytoplasmic leakage due to membrane disruption and also interfere with the normal functioning of membrane proteins. CPPs might also exhibit cellular toxic effects, such as transportan, which affects GTPase activity (Soomets, U. et al. (2000) Biochim. Biophys. Acta 1467, 165-176). Furthermore, there is a burgeoning body of evidence that many CPPs only exert their function under certain very specific conditions that cannot be met in an in vivo setting. Another drawback is that, depending on the target cell, the CPPs may be rapidly degraded in the cells. Lastly, as many known CPPs are derived from non-human proteins, toxic and/or immunogenic effects have been regularly observed, which may interfere with the utilization of these peptides, e.g., for therapeutic applications in humans.

Thus, there still remains a need for improved cell-penetrating peptides that overcome the above-mentioned limitations. In particular, there is a need for cell-penetrating peptides that represent suitable transfection vesicles or cargos enabling delivery of compounds such as therapeutic agents into target cells with high efficiency but without exerting significant cytotoxic and/or immunogenic effects.

Furthermore, there is also a need for compositions comprising such CPPs as well as for methods employing such CPPs as molecular tools for diagnostic and therapeutic applications.

Accordingly, it is an object of the present invention to provide such CPPs and corresponding compositions and methods.

SUMMARY OF THE INVENTION

In one aspect, the present invention relates to a peptide molecule capable of being internalized into a cell, wherein the peptide molecule (a) has a length of at least 10, preferably of at least 15 amino acid residues; (b) comprises in its primary amino acid sequence at least 25%, preferably at least 30% positively charged amino acid residues; and (c) is internalized into a cell with an efficacy being at least 80%, preferably at least 90% of the internalization efficacy of the TAT peptide having the amino acid sequence GRKKRR QRRRPPQ (SEQ ID NO: 1).

In specific embodiments, at least a part of the peptide forms an alpha-helical secondary structure.

Preferably, the peptide is of mammalian, particularly preferably of human origin.

In further preferred embodiments, the peptide has an amino acid sequence selected from the group consisting of: GAAEAAARVYDLGLRRLRQRRRLRRERVRA (SEQ ID NO: 2); IREIME KFGKQPVSLPARRLKLRGRKRRQR (SEQ ID NO: 3); YLKWRKHHRVIAGQFFGHHHTDSF RMLYD (SEQ ID NO: 4); SKVRFCSGRKRPVRRRPEPQLK-GIVTRLFS (SEQ ID NO: 5); SMSVLEPGTAKKHKGGIL-RKGAKLFFRRRH (SEQ ID NO: 6); QRKIGGRGRI-ISPYRTPVLR RHRYSIFRST (SEQ ID NO: 7); QHVRIRVIKKKKVIMKKRKKLTLTRPTPLV (SEQ ID NO: 8); FHFFPRRPRIHFRFPNRPFVPSRCNHRFPF (SEQ ID NO: 9); FALLGDFFRKSKEKIGKEFK RIVQRIKDFL-RNLVPRTES (SEQ ID NO: 10); and an amino acid sequence having over its total length at least 70%, preferably at least 80% overall sequence identity with any one of SEQ ID NO: 2 to SEQ ID NO: 10.

In particularly preferred embodiments, the peptide has an amino acid sequence selected from the group consisting of: GAAEAAARVYDLGLRRLRQRRRLRRERVRA (SEQ ID NO: 2); IREIMEKFGKQPVSLPARRLKLRGRKRRQR (SEQ ID NO: 3); YLKWRKHHRVIAGQFFGH HHTDS-FRMLYD (SEQ ID NO: 4); and an amino acid sequence having over its total length at least 70%, preferably at least 80% overall sequence identity with any one of SEQ ID NO: 2 to SEQ ID NO: 4.

In another aspect, the present invention relates to a nucleic acid molecule encoding the peptide as defined herein above.

In yet another aspect, the present invention relates to a vector comprising the nucleic acid molecule as defined herein above.

In yet another aspect, the present invention relates to host cell comprising the vector as defined herein above.

In a further aspect, the present invention relates to a method of producing the peptide as defined herein above, comprising: (a) culturing the host cell as defined herein above under suitable conditions; and (b) isolating the peptide produced.

In yet another aspect, the present invention relates to a composition comprising at least one peptide as defined herein above being attached to any one of the group consisting of one or more nucleic acid molecules, one or more peptides or proteins, one or more small molecules, and one or more nanoparticles, wherein the attachment is accomplished by a linkage selected from the group consisting of a covalent linkage and a non-covalent linkage.

In specific embodiments, the at least one peptide of the composition is attached to one or more other peptides. Preferably, the one or more other peptides form at least in part in an alpha-helical secondary structure. In particular embodiments, the one or more other peptides are pro-apoptotic peptides.

In a further aspect, the present invention relates to a method of producing the composition as defined herein above, comprising: (a) providing at least one peptide as defined herein above; and (b) contacting the at least one peptide with any one of the group consisting of one or more nucleic acid molecules, one or more peptides or proteins, one or more small molecules, and one or more nanoparticles, thus allowing for forming an attachment.

In yet another aspect, the present invention relates to a method of detecting the internalization behavior of the peptide as defined herein above or the composition as defined herein above, comprising: (a) administering the peptide or the composition to one or more cells; and (b) detecting the internalization of the peptide or the composition.

In a further aspect, the present invention relates to a pharmaceutical composition comprising at least one peptide as defined herein above or the composition as defined herein above, and optionally further comprising one or more pharmaceutically acceptable excipients and/or additives.

In another aspect, the present invention relates to the use of the peptide as defined herein above or the composition as defined herein above for the transformation or transfection of one or more cells.

In yet another aspect, the present invention relates to the peptide as defined herein above or the composition as defined herein above for use in the prevention and/or treatment of a condition selected from the group consisting of cancer, immune diseases, cardiovascular diseases, neuronal diseases, infections, and inflammatory diseases.

In yet another aspect, the present invention relates to a method for the prevention and/or treatment of a condition selected from the group consisting of cancer, immune diseases, cardiovascular diseases, neuronal diseases, infections, and inflammatory diseases, comprising: administering at least one peptide as defined herein above or the composition as defined herein above to a subject.

In a further aspect, the present invention relates to a kit-of-parts, comprising at least any one of: (a) the peptide as defined herein above; (b) the nucleic acid molecule as defined herein above; (c) the vector as defined herein above; (d) the host cell as defined herein above; and (e) the composition as defined herein above.

Other embodiments of the present invention will become apparent from the detailed description hereinafter.

Shown is a schematic representation of the screening procedure applied. All human entries in the SwissProt database were included along with description and Gene Ontology (GO) annotation (A) and analyzed with a sliding window of 30 amino acid residues (B). To identify putative cell-penetrating peptides (CPPs), bioinformatics filters were applied (C): first, only peptides with 10 or more positive charges were chosen; second, only extracellular proteins with low probability of immunogenicity were chosen ("steps 2 and 3"). In order to narrow down the number of peptides, several approaches were chosen: intersection of highest iso-electric point (IEP) and highest hydrophobicity, sequence similarity to the HIV-derived TAT peptide sequence as well as careful analysis of the literature and BLAST results.

Figure 2:
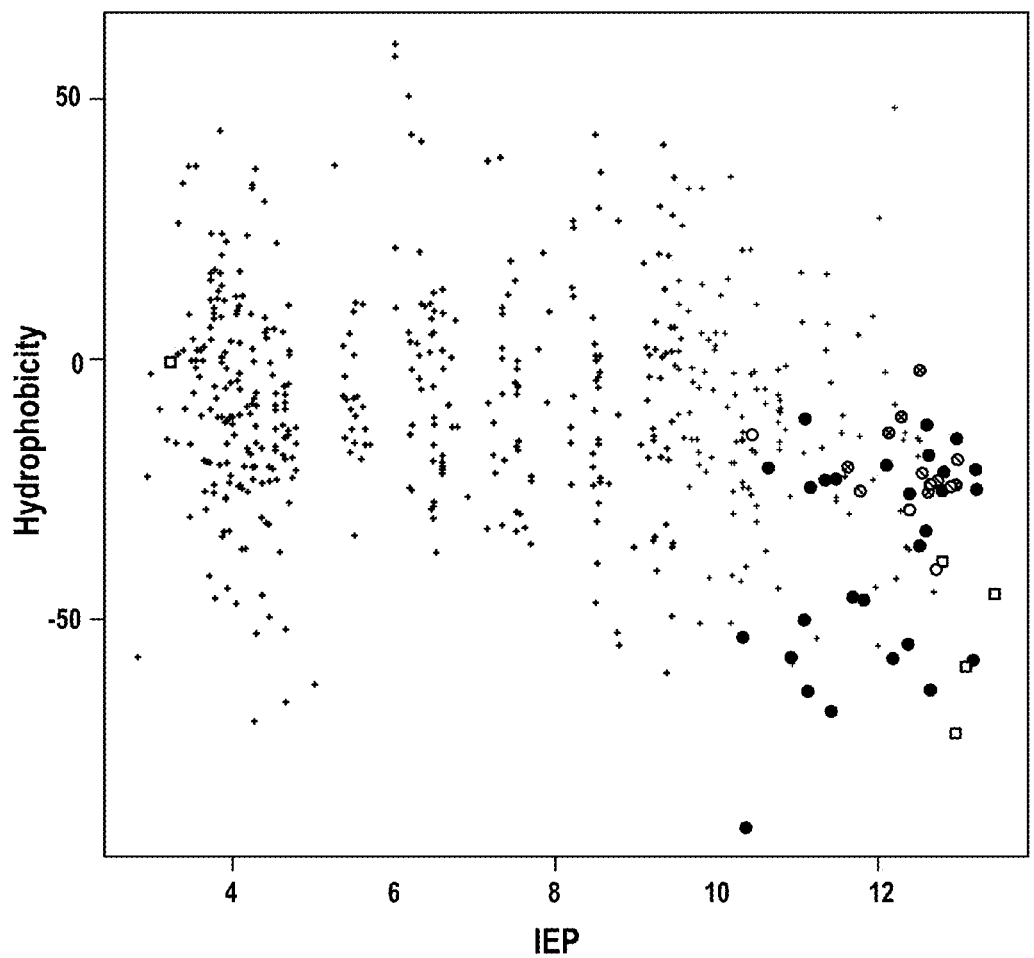

FIG. 2: Hydrophobicity Vs. IEP Plot of 500 Random Peptides.

500 randomly selected peptides from the entirety of $10.5 \times 10^6$ human 30mers were plotted for their hydrophobicity versus their IEP. The control peptides TAT, poly-Arg, REV, protamine and INF7 (non-filled squares) were added. Non-toxic and non-transfecting peptides are depicted as black dots, transfecting toxic peptides as blue dots, toxic peptides as red dots and non-toxic transfecting peptides as green dots.

Figure 3:
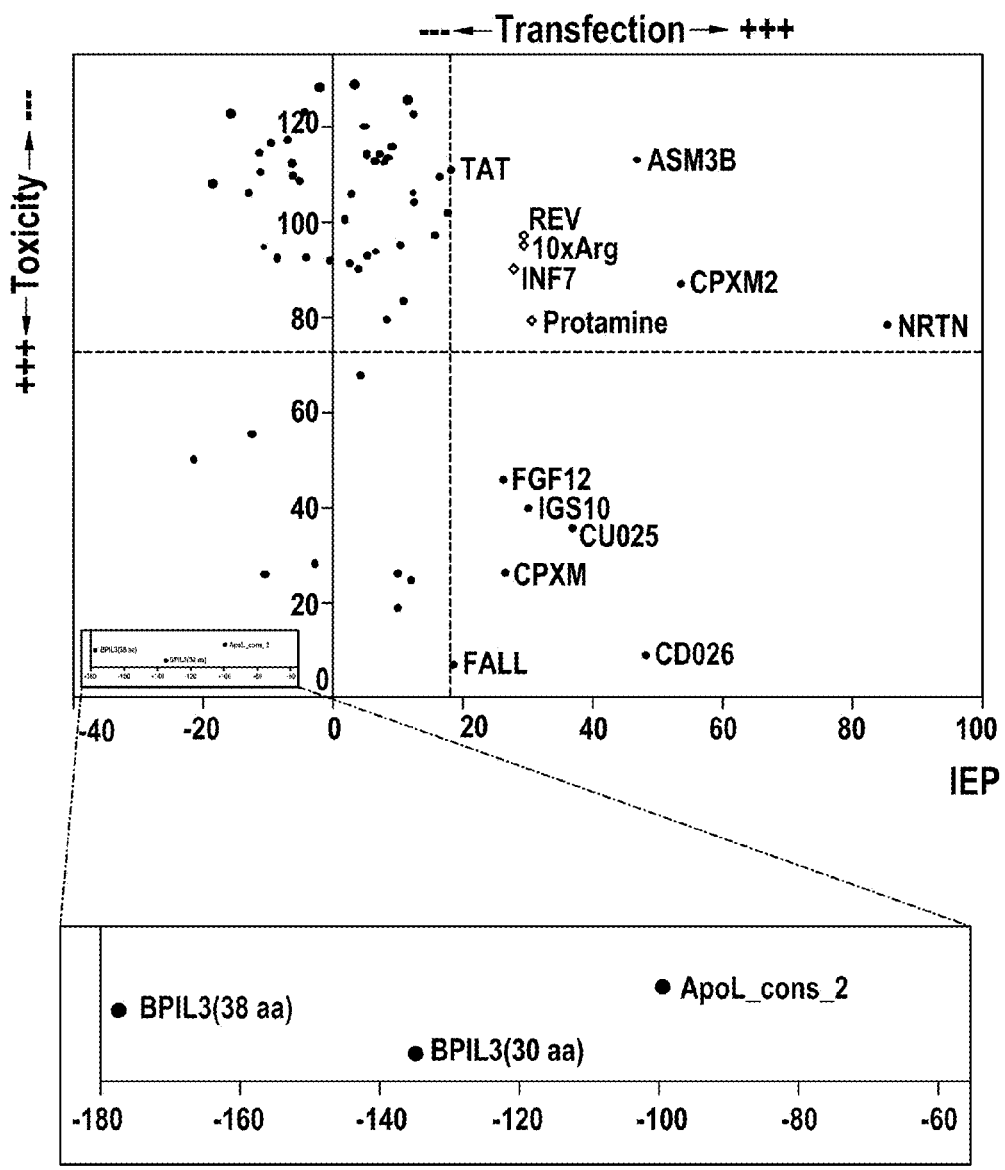

FIG. 3: Toxicity Vs. Transfection Ability Plot of all the Peptides Analyzed.

All peptides analyzed for their ability to transfect siRNAs and their cellular toxicity were plotted for the average GAPDH mRNA levels at 20 µM each of Aha1 siRNA and luciferase siRNA (y-axis, "Toxicity") as well as for the respective differences of Aha1/GAPDH for luciferase and Aha1/GAPDH for Aha1 siRNA at 20 µM each (x-axis, "Transfection"). Threshold values for toxicity (70% average GAPDH mRNA content) and transfection (>TAT, 18%) are indicated by red dotted lines. The dotted lines generate 4 quadrants: top left: non-transfecting, non-toxic peptides; top right: transfecting non-toxic peptides; bottom left: toxic peptides; bottom right: transfecting toxic peptides. Inset box shows toxic peptides outside of the range of the plotted area.

Figure 4:
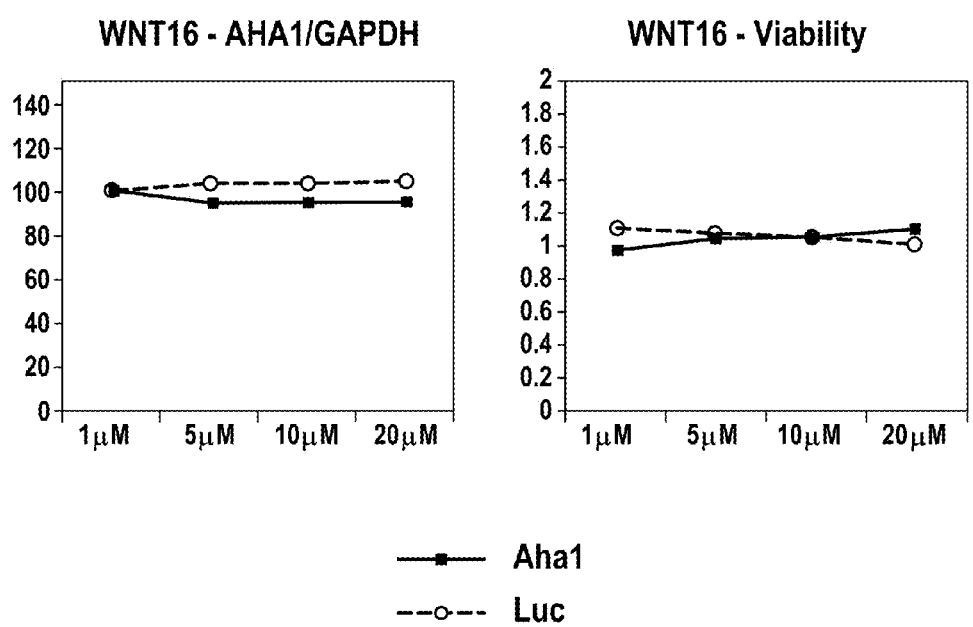

FIG. 4: Analysis of the Peptide WNT16.

WNT16 is an example of a non-toxic, not transfection competent (i.e. non-transfecting) peptide. The experimental approach was the same as in FIG. 3. The mRNA values obtained at 1 µM were set to 100% to show dose dependent effects. Viability is expressed as percent of medium control. Aha1 siRNA is shown as black filled squares; luciferase siRNA is shown as non-filled circles.

Figure 5:
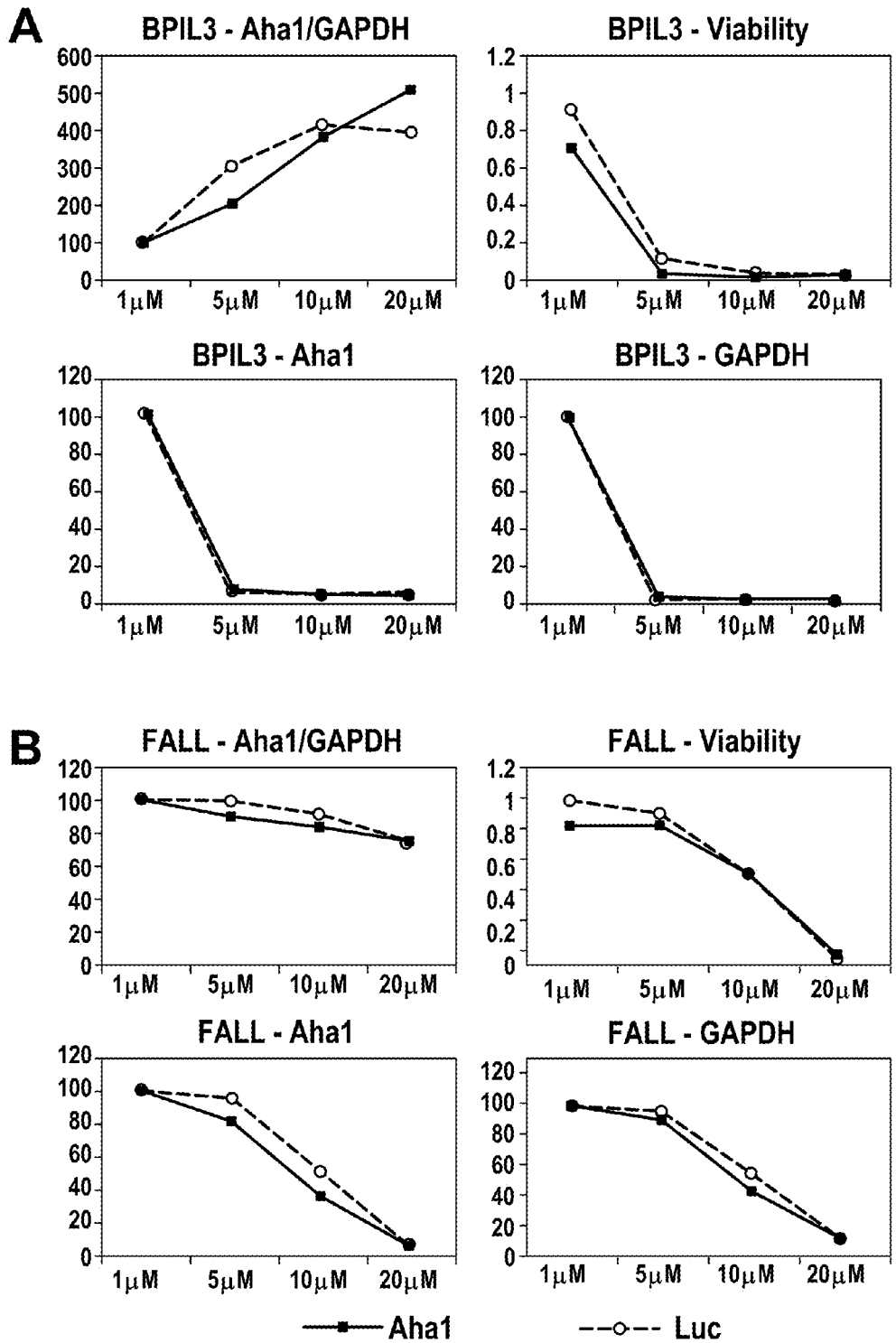

FIG. 5: Analysis of the Peptides BPIL3 and FALL.

BPIL3 is an example of a toxic, not transfection competent peptide. The experimental approach was the same as in FIG. 3. (A). Note that the levels of Aha1 and GAPDH exhibit a similar behavior, with GAPDH showing higher sensitivity. This explains the increase in the Aha1/GAPDH values. To show the potential therapeutic window for a toxic peptide with transfection efficiency that is masked by its toxicity, the same analysis was performed with FALL (B). The mRNA values for both peptides (A, B) obtained at 1 µM were set to 100% in order to elucidate dose dependent effects. Viability for both peptides (A, B) is expressed as percent of medium control. Aha1 siRNA is shown as black filled squares; luciferase siRNA is shown as non-filled circles.

Figure 6:
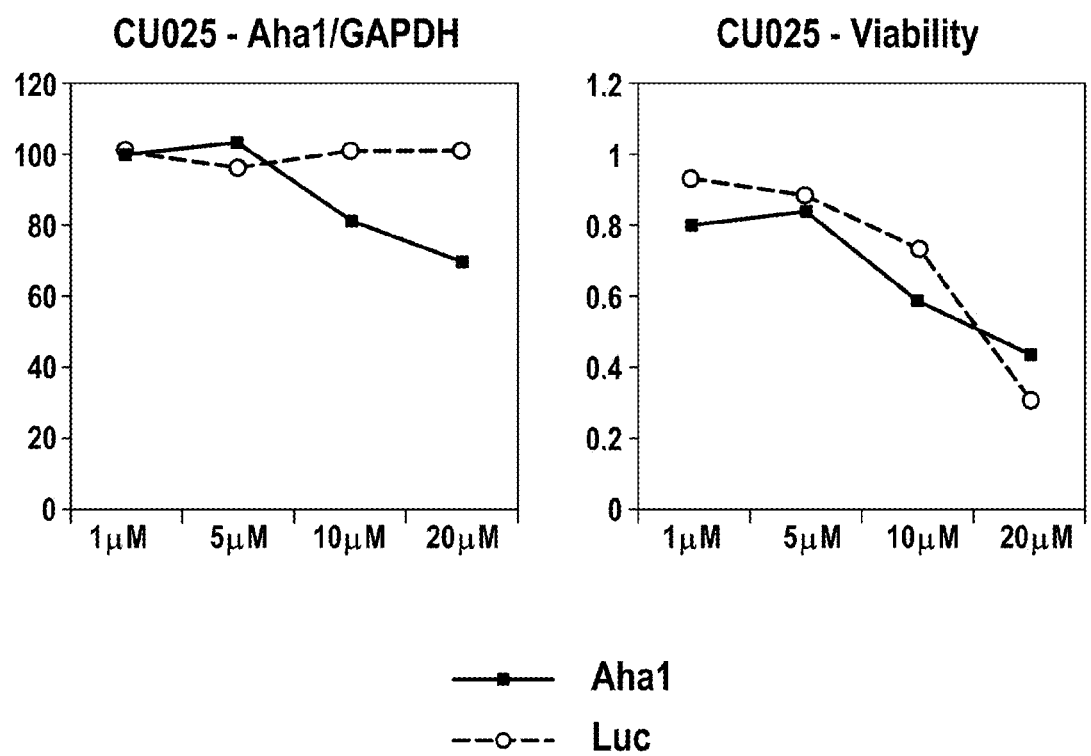

FIG. 6: Analysis of the Peptide CU025.

CU025 is an example of a toxic, transfection competent peptide. The experimental approach was the same as in FIG. 3. The mRNA values obtained at 1 µM were set to 100% to show dose dependent effects. Viability is expressed as percent of medium control. Aha1 siRNA is shown as black filled squares; luciferase siRNA is shown as non-filled circles.

FIG. 7: Analysis of Non-Toxic Transfection Competent Peptides.

CPXM2, ASM3B, and NRTN are examples of non-toxic transfection competent peptides. The experimental approach was the same as in FIG. 3. As a control, the Aha1/GAPDH ratios for TAT and Poly-Arg were determined (A). Both CPXM2 (B) and ASM3B (C) exhibit a concentration dependent reduction of the Aha1 mRNA over the GAPDH mRNA while not showing significant interference with cell viability. Detailed analysis of NRTN (D) results in a strong reduction of the Aha1 mRNA over the GAPDH mRNA without significant dose dependent effects on cell viability. (A, B, C, D) In all cases, the mRNA values obtained at 1 µM were set to 100% in order to show dose dependent effects. Viability is expressed as percent of medium control. Aha1 siRNA is shown as black filled squares; luciferase siRNA is shown as non-filled circles.

Figure 8:
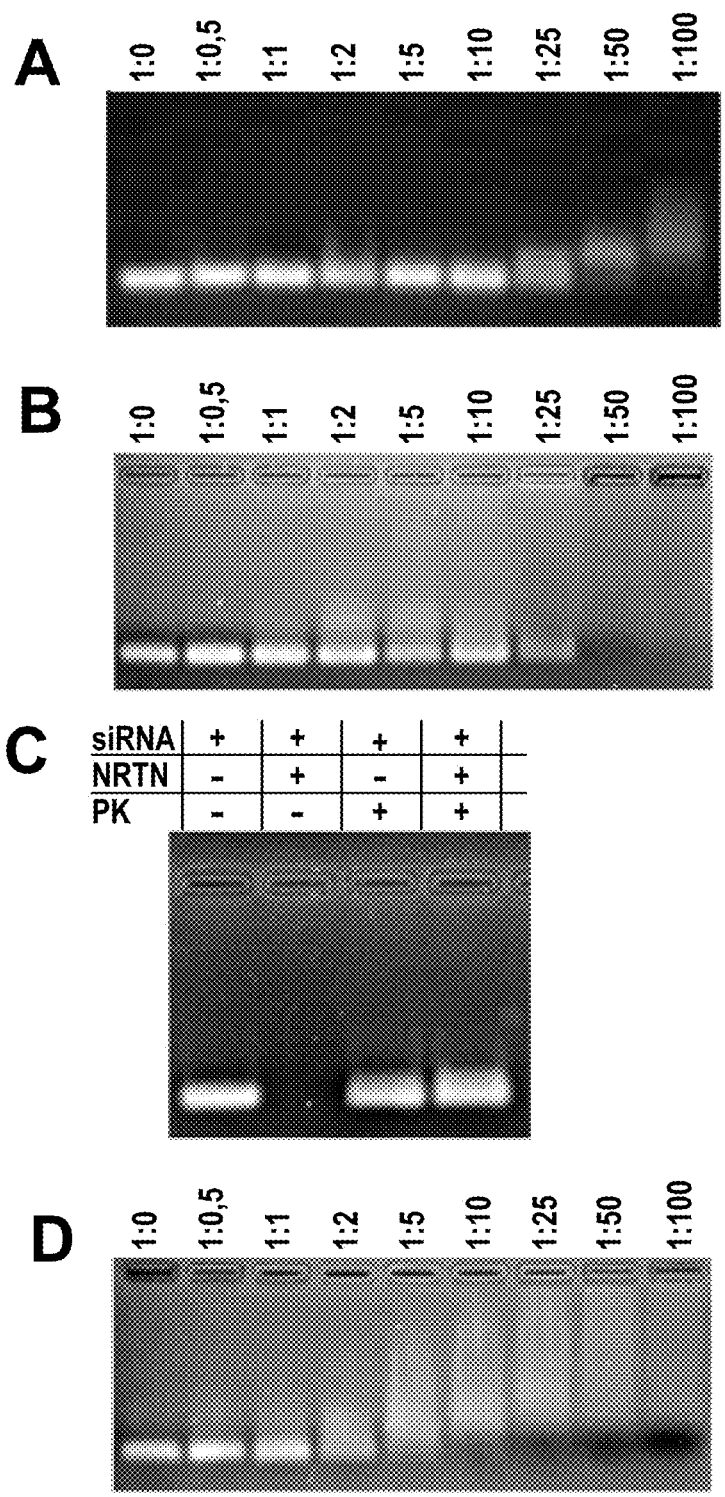

FIG. 8: Gel-Shift Analysis of Selected Peptides.

In order to show the respective complex formation of the peptides TAT (A), NRTN (B), and WNT16 (D), 500 µg siRNA duplex were incubated with the indicated molar ratios of peptide for one hour and analyzed by means of agarose gel electrophoresis and ethidium bromide staining. This analysis shows complex formation between siRNA and TAT, NRTN and WNT16, respectively. In order to demonstrate the effect of NRTN on the accessibility of siRNA to ethidium bromide, the complex was incubated in the presence and absence of proteinase K (C).

Figure 9:
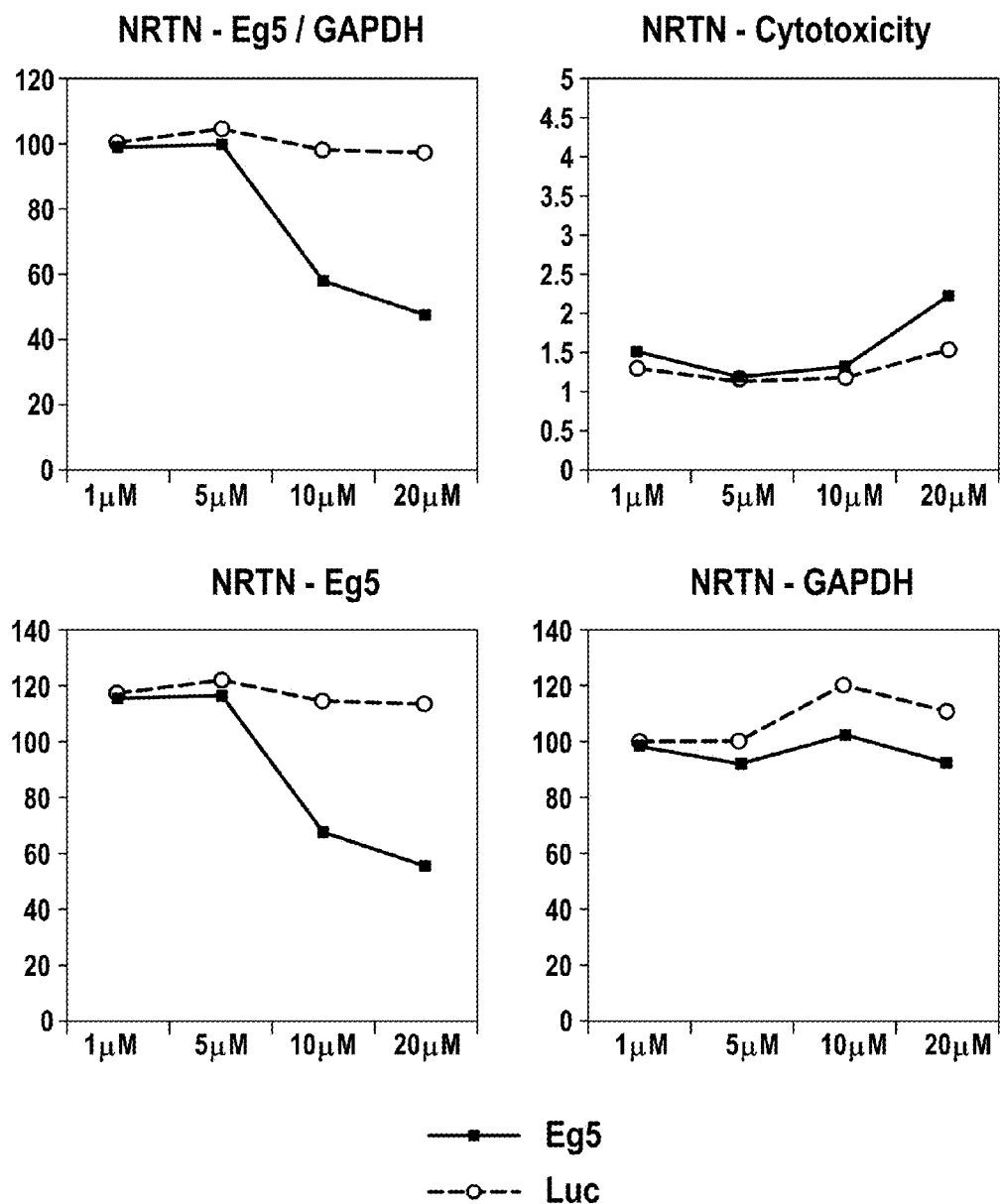

FIG. 9: NRTN Mediated Transfection is Sufficient to Cause a Cellular Phenotype.

The siRNA sequence specificity of NRTN was investigated via analysis of the peptide's ability to transfect a siRNA duplex targeting human Eg5 mRNA. The Eg5 knockdown dependent induction of apoptosis was determined by performing a CytoTox-Glo cytotoxicity assay (Promega Inc.). The mRNA values obtained at 1 µM were set to 100% to show dose dependent effects. Induction of apoptosis is expressed as percent of medium control. Aha1 siRNA is shown as black filled squares; luciferase siRNA is shown as non-filled circles.

Figure 10:
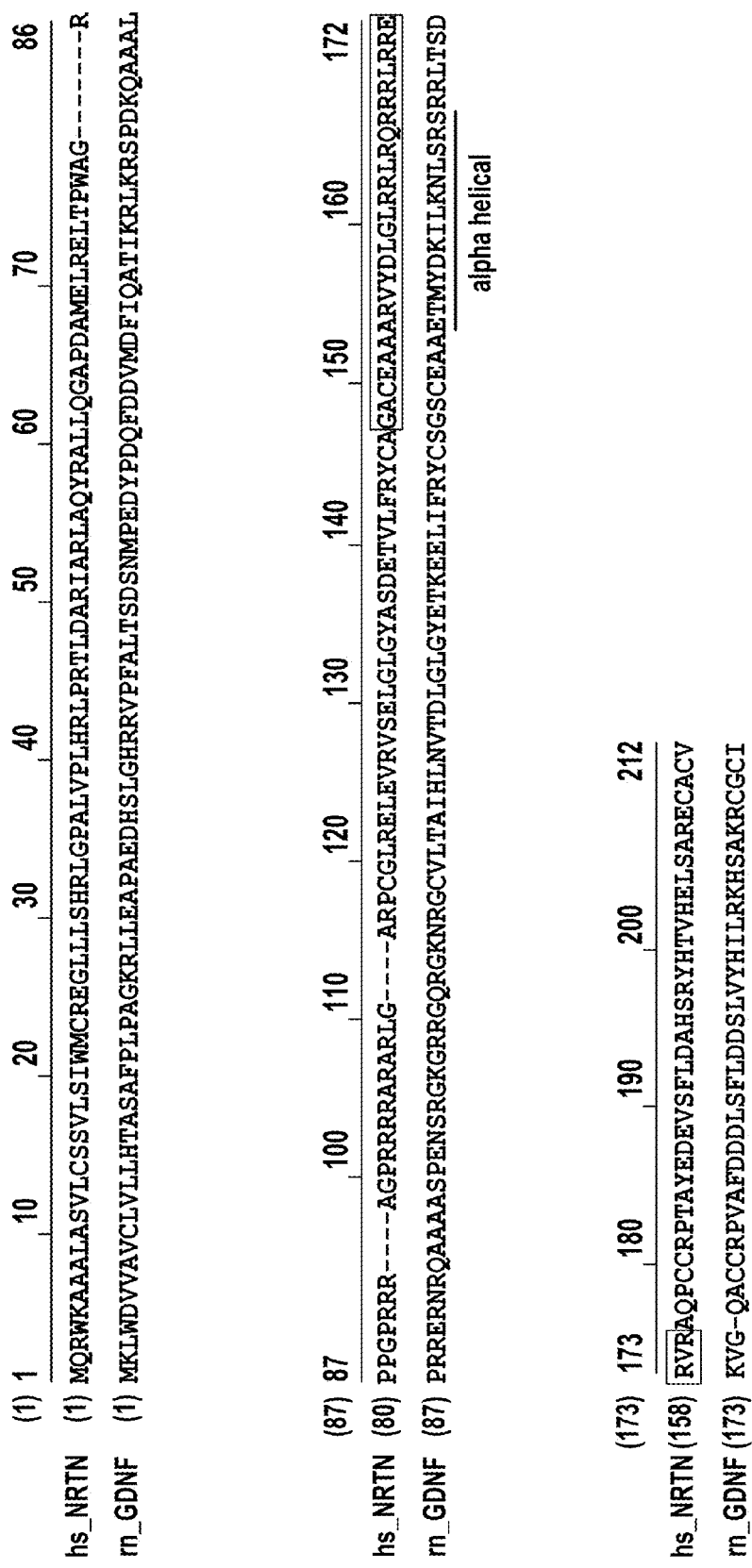

FIG. 10: Sequence Alignment of GDNF and NRTN.

An amino acid sequence alignment of rat GDNF and human NRTN shows their relationship. Identical amino acids are in light grey on white background, similar amino acids black on light gray background and different amino acids black on white background. An alpha helical stretch of rat GDNF is indicated. The NRTN peptide used is boxed.

FIG. 11: NTRN has an Alpha-Helical Structure Element.

UV CD spectroscopy analyses of FALL (A), NRTN (B), and TAT (C) peptides. The spectra were determined from 195 nm to 260 nm with a data pitch of 0.1 nm and a bandwidth of 1 nm using 0.1 mg/ml peptide in the absence ("H2O") or presence of 10%, 25%, and 50% trifluoro-ethanol (TFE), respectively.

FIG. 12: NRTN, TAT and FALL Function as Cell Penetrating Peptides.

FACS analyses of TAT (A), WNT16 (B), FALL (C), and NRTN (D) peptides encompassing a N-terminal FITC label. Cells were incubated for 3 hours in the presence of peptide, treated with proteinase K for 30 minutes and analyzed by FACS for internalized peptides in the FITC channel. Black lines indicate signals at 1 µM, light grey indicates signals at 5 µM, and dark grey lines indicate signals at 10 µM.

Figure 13:
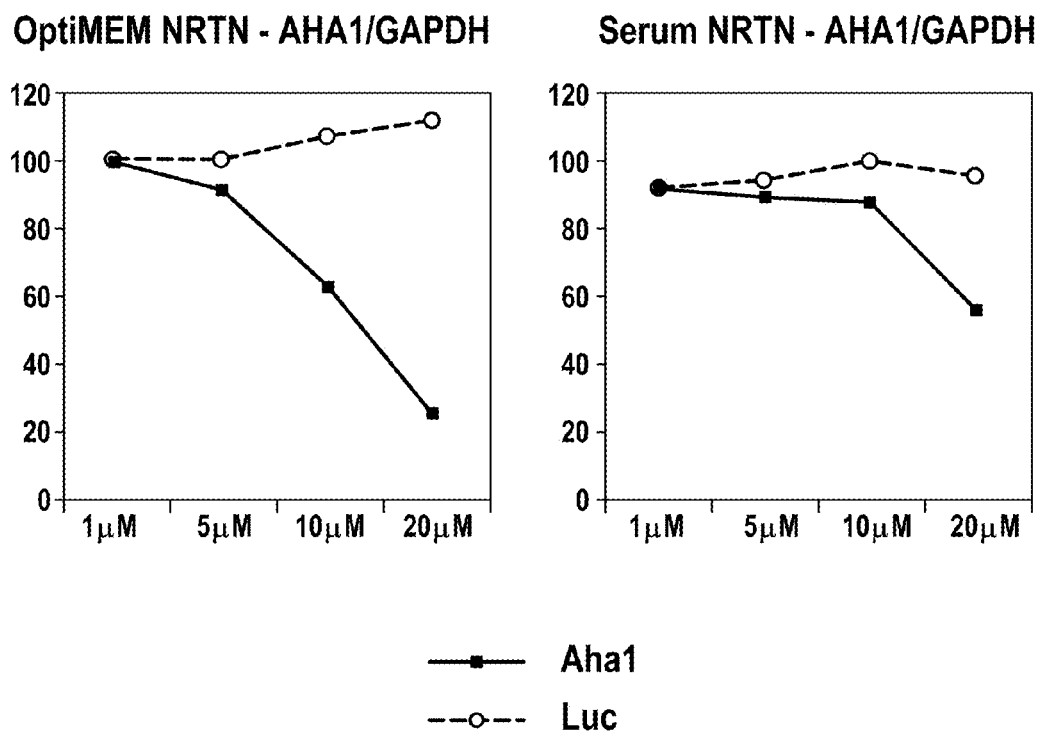

FIG. 13: NRTN Shows Activity Under Serum Conditions.

NRTN was analyzed for its ability to transfect siRNA duplexes in the absence (A) and presence (B) of serum in the transfection medium. The experimental approach was the same as in FIG. 3. The assay was either carried out in normal RPMI 1640 growth medium containing 10% FCS (B) or for three hours in OptiMEM reduced serum medium followed by change of the medium back to normal growth medium (A). The mRNA values obtained at 1 µM were set to 100% to show dose dependent effects. Aha1 siRNA is shown as black filled squares; luciferase siRNA is shown as non-filled circles.

Figure 14:
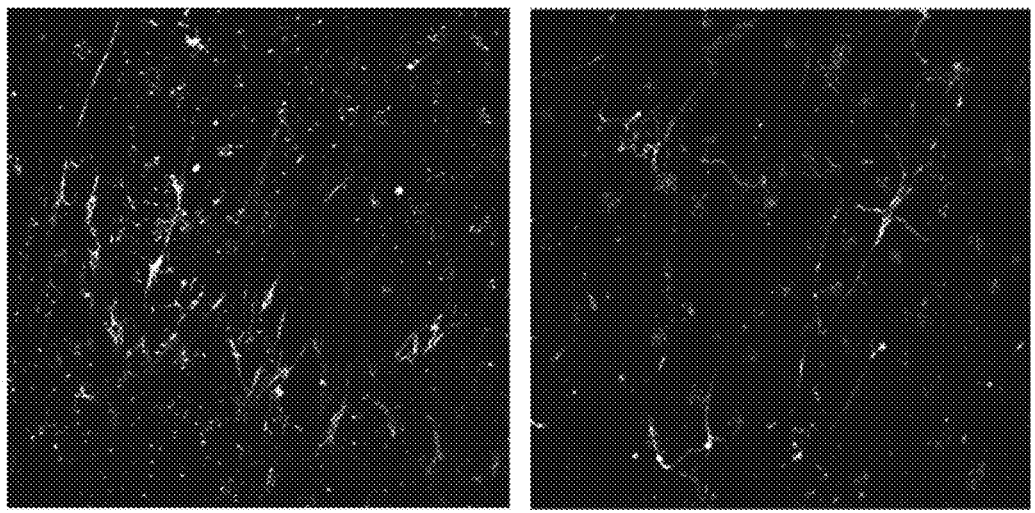

FIG. 14: NRTN Uptake into Human Brain Endothelial Cells.

Fluorescein isothiocyanate (FITC)-conjugated NRTN peptides (N-terminal and C-terminal conjugation, respectively) were incubated with hCMEC/D3 brain endothelial cells at 5 µM for 1 h at 37° C. Subsequently, the cells were washed and fixed. Images were taken using a fluorescence microscope. In both cases, the peptide localizes to intracellular endosomal structures.

Figure 15:
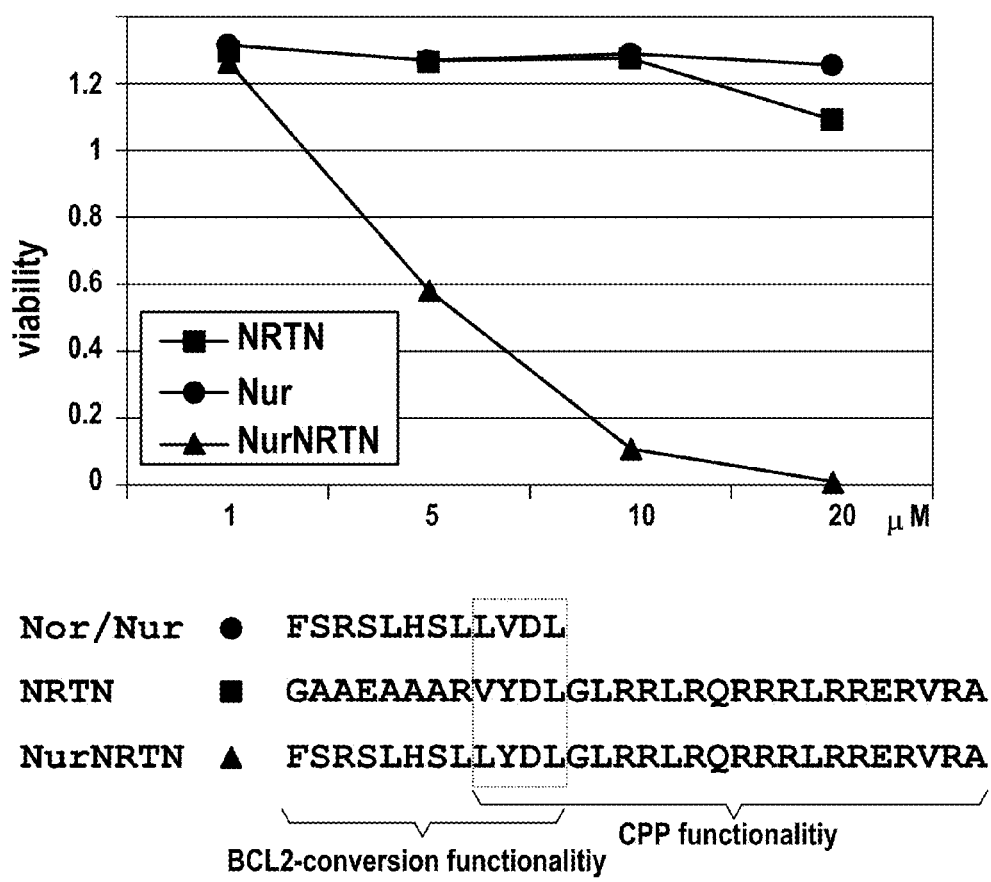

FIG. 15: NRTN-Mediated Cellular Uptake of a Pro-Apoptotic Nur77 Peptide.

MCF-7 human breast cancer cells were incubated for 24 h in the presence of various concentrations of NRTN (squares), Nur (circles), and NurNRTN (triangles) peptides. The respective amino acid sequences are given in the bottom panel. The experimental approach for assessing cell viability (and thus induction of apoptosis) was the same as in FIG. 3.

FIG. 16: NRTN-Mediated Cellular Uptake of a Pro-Apoptotic 4E-BP1 Peptide.

MCF-7 human breast cancer cells were incubated for 24 h in the presence of various concentrations of 4E-BP1 (circles), TAT4E-BP1 (squares), and NRTN4E-BP1 (triangles) peptides (top panel). The respective effects of the two fusion peptides (solid lines) were further compared with inactive variants (TATinact4E-BP1 and NRTNinact4E-BP1; dotted lines) thereof, respectively (medium panel). The respective amino acid sequences are given in the bottom panel. The experimental approach for assessing cell viability (and thus induction of apoptosis) was the same as in FIG. 3.

DETAILED DESCRIPTION OF THE INVENTION

The present invention is based on the unexpected finding that by combining bioinformatics screening and subsequent experimental evaluation of candidate peptides several CPPs could be identified that exhibit a superior functional profile as compared to the previous "gold standard" reference peptide TAT, in particular a higher overall transfection efficacy, a higher transfection activity in the presence of serum as well as a lower degree of cytotoxicity. Strikingly, these CPPs do not show any significant similarities with regard to their primary amino acid sequences. These peptides might thus serve as modules in the development of new potent delivery agents for therapeutic intervention.

The present invention illustratively described in the following may suitably be practiced in the absence of any element or elements, limitation or limitations, not specifically disclosed herein.

Where the term "comprising" is used in the present description and the claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun, e.g., "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like, in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In a first aspect, the present invention relates to a peptide molecule capable of being internalized into a cell, wherein the peptide molecule:

(a) has a length of at least 10, preferably of at least 15 amino acid residues;
(b) comprises in its primary amino acid sequence at least 25%, preferably at least 30% positively charged amino acid residues; and
(c) is internalized into a cell with an efficacy being at least 80%, preferably at least 90% of the internalization efficacy of the TAT peptide having the amino acid sequence GRKKRRQRRRPPQ (SEQ ID NO: 1).

The term "peptide molecule" (also referred to herein as "peptide"), as used herein, refers to any naturally occurring or synthetic (e.g., generated by chemical synthesis or recombinant DNA technology) linear macromolecules comprising a plurality of natural or modified amino acid residues connected via peptide bonds. Such peptides may form oligomers consisting of at least two identical or different peptide molecules.

The peptides of the invention have a length of at least 10 amino acid residues (e.g., 10, 11, 12, 13 or 14 amino acid residues), and preferably have a length of at least 15 amino acid residues, of at least 20 amino acid residues, of at least 25 amino acid residues, of at least 30 amino acid residues, of at least 35 amino acid residues, of at least 40 amino acid residues or of at least 45 amino acid residues. In specific embodiments, the peptides of the invention have a length of 15, 16, 17, 18, 19, 20, 21, 22, 23, 24, 25, 26, 27, 28, 29, 30, 31, 32, 33, 34, 35, 36, 37, 39, 40, 41, 42, 43, 44 or 45 amino acid residues.

The term "natural amino acid residue", as used herein, denotes any of the 22 "standard" amino acids that are naturally incorporated into peptides. Of these twenty-two, twenty are directly encoded by the universal genetic code. The remaining two, selenocysteine and pyrrolysine are incorporated into proteins by unique synthetic mechanisms. Typically, the amino acid residues of a peptide according to the invention are present as L-isomers. In some embodiments, one or more amino acid residues of a peptide according to the invention are present as D-isomers. The term "modified amino acid residue", as used herein, denotes non-standard amino acids such as post-translationally modified amino acids. Examples of post-translational modifications include inter alia phosphorylation, glycosylation, acylation (e.g., acetylation, myristoylation, palmitoylation), alkylation, carboxylation, hydroxylation, glycation, biotinylation, ubiquitinylation, changes of the chemical nature (e.g., β-elimination deimidation, deamidation,), and structural changes (e.g., the forming of disulfide bridges).

The amino acid sequences of the peptides as defined herein are written, according to the general convention, from the amino (N)-terminus to the carboxyl (C)-terminus. However, the corresponding "reverse" peptides are also within the present invention. The term "reverse peptide", as used herein, denotes peptides having the same sequence as their "regular" counterparts but in reverse orientation, that is, from the C-terminus to the N-terminus. For example, the "regular" TAT peptide has the amino acid sequence GRKKRRQRRRPPQ. The corresponding "reverse" TAT peptide has the amino acid sequence QPPRRRQRRKKRG.

The peptides of the present invention have in their respective primary amino acid sequences (that is, over their entire length) at least 25%, preferably at least 30% positively charged amino acid residues. The term "positively charged amino acids" (herein also referred to as "basic amino acids"), as used herein, denotes the entirety of lysine (K), histidine (H), and arginine (R) residue present in a particular peptide. In specific embodiments, a peptide of the present invention comprises in its primary amino acid sequence 25%, 26%, 27%, 28%, 29%, 30%, 31%, 32%, 33%, 34% or 35% positively charged amino acid residues. In other embodiments, the peptides of the invention comprise in their respective primary amino acid sequences at least 35%, at least 40%, at least 45%, at least 50%, at least 55%, or at least 60% positively charged amino acid residues.

The term "capable of being internalized into a cell", as used herein, refers to the ability of the peptides to pass cellular membranes (including inter alia the outer "limiting" cell membrane (also commonly referred to as "plasma membrane"), endosomal membranes, and membranes of the endoplasmatic reticulum) and/or to direct the passage of a given agent or cargo through these cellular membranes. Such passage through cellular membranes is herein also referred to as "cell penetration". Accordingly, peptides having said ability to pass through cellular membranes are herein referred to as "cell-penetrating peptides". In the context of the present invention, any possible mechanism of internalization is envisaged including both energy-dependent (i.e. active) transport mechanisms (e.g., endocytosis) and energy-independent (i.e. passive) transport mechanism (e.g., diffusion). As used herein, the term "internalization" is to be understood as involving the localization of at least a part of the peptides that passed through the plasma cellular membrane into the cytoplasma (in contrast to localization in different cellular compartments such as vesicles, endosomes or in the nucleus). In specific embodiments, a given transport mechanism that is employed ensures that at least 0.01%, at least 0.05%, at least 0.1%, at least 0.5%, at least 1%, at least 2%, at least 5% or at least 10% of the peptides or compositions internalized localize into the cytoplasm.

The peptides of the present invention are internalized into a cell with an efficacy being at least 80%, preferably at least 90% of the internalization efficacy of the TAT peptide having the amino acid sequence GRKKRRQRRRPPQ (SEQ ID NO: 1; see also Vives; E. et al. (1997), supra). In other words, the functional activity of the peptides is characterized in comparison to a reference peptide (TAT represents the "gold standard" with regard to cell-penetrating peptides). In specific embodiments, the peptides of the invention are internalized with an efficacy being 80%, 85%, 90% or 95% of the internalization efficacy of the TAT peptide. In specific preferred embodiments, the peptides of the invention are internalized with at least the same efficacy (i.e. 100%) as the TAT peptide. Particularly preferably, the peptides of the invention are internalized with a higher efficacy (i.e. more than 100% or at least 101%) as the TAT peptide, e.g., with 105%, 110%, 115%, 120%, 125%, 130%, 140%, 150%, 160%, 170%, 180%, 190%, or 200% of the internalization efficacy of the TAT peptide.

The term "internalization efficacy", as used herein, is to be understood in a broad sense. The term does not only refer to the extent to which a peptide of the invention passes through the plasma membrane of cells (i.e. the internalization behavior per se) but also to the efficiency by which the peptide directs the passage of a given agent or cargo through the cell plasma membrane (i.e. its transfection capability; herein also referred to as "transfectivity"). Numerous methods of determining the internalization behavior and/or transfection capability of a given peptide are established in the art, for example, by attaching a detectable label (e.g. a fluorescent dye) to the peptide (and/or to the cargo to be transfected) or by fusing the peptide with a reporter molecule, thus enabling detection once cellular uptake of the peptide occurred, e.g., by means of FACS analysis or via specific antibodies (see, e.g., Ausubel, F. M. et al. (2001) *Current Protocols in Molecular Biology*, Wiley & Sons, Hoboken, N.J., USA). The skilled person is also well aware how to select the respective concentration ranges of the peptide and, if applicable, of the cargo to be employed in such methods, which may depend on the nature of the peptide, the size of the cargo, the cell type used, and the like.

In further embodiments, the peptides of the present invention do not exert significant cytotoxic and/or immunogenic effects to their respective target cells after having been internalized, that is, they do not interfere with cell viability (at least at concentrations that are sufficient to mediate cellular transfection and/or penetration). The term "not significant", as used herein, is to be understood that less than 50%, preferably less than 40% or 30%, and particularly less than 20% or 10% of the target cells are killed after internalization of a peptide of the invention. In other embodiments, the cytotoxic (and/or immunogenic) effects exerted by the peptides upon internalization into a cell are the same or less than the corresponding effects exerted by the TAT peptide having the amino acid sequence GRKKRRQRRRPPQ (SEQ ID NO: 1). In specific embodiments, the cytotoxic (and/or immunogenic) effects exerted by the peptides upon internalization into a cell are less than 95%, less than 90%, less than 85%, less than 80%, less than 75%, less than 70%, less than 60%, less than 50%, less than 40%, less than 30%, less than 20%, or less than 10% of the effects exerted by the TAT peptide. The skilled person is well aware of methods of determining the cytotoxicity of a given compound and/or the viability of a given target cell to which such a compound is applied (see also, e.g., Ausubel, F. M. et al. (2001), supra). Corresponding assay kits are commercially available from various suppliers.

In specific embodiments, the potential intrinsic cytotoxic and/or immunogenic effects of a peptide of the invention may "masked" by introducing one or more modifications into the peptide, e.g., by means of chemical synthesis or recombinant DNA technology. Such modifications may relate, for example, to the addition, removal or substitution of functional groups or to the variation of the positions of such functional groups. The skilled person is well aware how such "masking" may be accomplished for a given peptide.

In further embodiments, the peptide molecules of the invention comprise at least one structured domain, that is, an element that forms (i.e. folds into) a stable secondary structure, that is, a particular spatial arrangement of amino acid residues that are located in proximity to each in the linear sequence. Often, the steric relationships between amino acid residues are of a regular kind, giving rise to periodic structures well known in the art such as α-helices (a rod-like tightly coiled structure) and β-strands (an extended stretch, with multiple such stretches optionally forming parallel or anti-parallel β-sheets). Within the present invention, the peptide molecule may comprise one such structured domain encompassed in an unstructured surrounding or may comprise two or more such structured domains (of the same type or of different types, e.g., two α-helices or one α-helix and one β-strand) separated from each other. In some embodiments, the peptide molecule forms a secondary structure over its entire length (i.e. does not comprise unstructured regions).

In preferred embodiments, at least a part of the peptide molecule as defined herein forms an alpha-helical secondary structure. The α-helical element may comprise at least 4 or 6 amino acid residues, and preferably at least 8 or 10 amino acid residues. In specific embodiments, the peptide molecule of the invention comprises a single α-helical element as the only secondary structure.

In preferred embodiments, the peptide molecules of the present invention are of mammalian origin, that is, that they are derived from an organism such as a mouse, rat, hamster, rabbit, cat, dog, pig, cow, horse or monkey. Particularly preferably, the peptide molecules are of human origin, that is, they are derived from or represent human sequences. The term "derived from human sequences", as used herein, denotes sequences of human origin bearing minor modifications (e.g., one or more amino acid substitutions) as compared to naturally occurring human sequences. The term "represent human sequences", as used herein, denotes a sequence being identical to a naturally occurring human sequence (i.e. bearing no sequence variations or modifications).

In further preferred embodiments, the peptide molecule of the invention has an amino acid sequence selected from the group consisting of:
  GAAEAAARVYDLGLRRLRQRRRLRRERVRA
    (NRTN peptide; SEQ ID NO: 2);
  IREIMEKFGKQPVSLPARRLKLRGRKRRQR
    (CPXM2 peptide; SEQ ID NO: 3);
  YLKVVRKHHRVIAGQFFGHHHTDSFRMLYD
    (ASM3B peptide; SEQ ID NO: 4);
  SKVRFCSGRKRPVRRRPEPQLKGIVTRLFS (FGF 12 peptide; SEQ ID NO: 5);
  SMSVLEPGTAKKHKGGILRKGAKLFFRRRH
    (CU025 peptide; SEQ ID NO: 6);
  QRKIGGRGRIISPYRTPVLRRHRYSIFRST (IGS10 peptide; SEQ ID NO: 7);
  QHVRIRVIKKKKVIMKKRKKLTLTRPTPLV (CPXM peptide; SEQ ID NO: 8);
  FHFFPRRPRIHFRFPNRPFVPSRCNHRFPF (CD026 peptide; SEQ ID NO: 9);
  FALLGDFFRKSKEKIGKEFKRIVQRIKD-FLRNLVPRTES (FALL39 Var.1 peptide (also referred to as FALL peptide; SEQ ID NO: 10); and
  an amino acid sequence having over its total length at least 70%, preferably at least 80% overall sequence identity with any one of SEQ ID NO: 2 to SEQ ID NO: 10.

In particularly preferred embodiments, the peptide has an amino acid sequence selected from the group consisting of SEQ ID NO: 2, SEQ ID NO: 3, SEQ ID NO: 4, and amino acid sequence having over its total length at least 70%, preferably at least 80% overall sequence identity with any one of SEQ ID NO: 2 to SEQ ID NO: 4.

The term "percent (%) sequence identity", as used herein, describes the number of matches of identical amino acids of two or more aligned amino acid sequences as compared to the number of amino acid residues making up the overall length of the template amino acid sequences. In other terms, when using an alignment for two or more sequences or sub-sequences (i.e. fragments or truncations derived thereof) the percentage of amino acid residues that are the same may be determined, when the (sub)sequences are compared and aligned for maximum correspondence over a window of comparison, or over a designated region as measured using a sequence comparison algorithm as known in the art, or when manually aligned and visually inspected. Hence, the above definition applies not only to the full-length sequences of SEQ ID NO: 2 to SEQ ID NO: 10 but also to any truncation of at least 10, preferably of at least 15 amino acid sequences comprised in any of SEQ ID NO: 2 to SEQ ID NO: 10.

To evaluate the identity level between two protein sequences, they can be aligned electronically using suitable computer programs known in the art. Such programs include inter alia BLAST (Altschul, S. F. et al. (1990) *J. Mol. Biol.* 215, 403-410), FASTA (Lipman, D. J. and Pearson, W. R. (1985) *Science* 227, 1435-1441) or implementations of the Smith-Waterman algorithm (Smith, T. F. and Waterman, M. S. (1981) *J. Mol. Biol.* 147, 195-197). These programs, in addition to providing a pairwise sequence alignment, also report the sequence identity level (usually in percent identity) and the probability for the occurrence of the alignment by chance (P-value). For amino acid sequences, the BLASTP program uses as default a word length (W) of 3, and an expectation (E) of 10. The BLOSUM62 scoring matrix (Henikoff, S, and Henikoff, J. G. (1992) *Proc. Natl. Acad. Sci. USA* 89, 10915-10919) uses alignments (B) of 50, expectation (E) of 10, M=5, N=4, and a comparison of both strands. Computer programs such as CLUSTALW (Higgins, D. et al. (1994) *Nucl. Acids Res.* 2, 4673-4680) can be employed to align more than two sequences. In addition, CLUSTALW does take sequence gaps into account in its identity calculations.

As long as an amino acid sequence having over its total length at least 70%, preferably at least 80% overall sequence identity with any one of SEQ ID NO: 2 to SEQ ID NO: 10, it is within the embodiments of the present invention. The type of amino acid alterations present (e.g., the terminal addition, insertion, deletion, and substitution of one or more amino acid residues or combinations thereof) are of no relevance. In specific embodiments, the "amino acid sequence derivatives" have at least 70%, at least 72%, at least 74%, at least 76%, or at least 78% overall sequence identity with any one of SEQ ID NO: 2 to SEQ ID NO: 10. Preferably, the "amino acid sequence derivatives" have at least 80%, at least 82%, at least 84%, at least 86%, at least 88%, at least 90%, at least 92%, at least 94%, at least 95%, at least 96%, at least 97%, at least 98%, or at least 99% overall sequence identity with any one of SEQ ID NO: 2 to SEQ ID NO: 10.

In a second aspect, the present invention relates to a nucleic acid molecule encoding the peptide molecule as defined herein above.

The term "nucleic acid molecule", as used herein, denotes any nucleic acid encoding the peptide of the invention. Examples of such nucleic acid molecules include naturally occurring nucleic acids such as deoxyribonucleic acid (DNA) or ribonucleic acid (RNA) as well as artificially designed nucleic acids that are chemically synthesized or generated by means of recombinant gene technology including, e.g., nucleic acid analogs such as inter alia peptide nucleic acids (PNA) or locked nucleic acids (LNA), (see, e.g., Sambrook, J., and Russel, D. W. (2001), *Molecular cloning: A laboratory manual* (3rd Ed.) Cold Spring Harbor, N.Y., Cold Spring Harbor Laboratory Press). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, target nucleic acids of the invention are 30 to 5.000 nucleotides in length, e.g., 30 to 3.000 nucleotides, 45 to 2.000 nucleotides, 60 to 1.000 nucleotides or 75 to 500 nucleotides. As used herein, the term "nucleotide" is to be understood as referring to both ribonucleotides and deoxyribonucleotides (i.e. RNA and DNA molecules).

Preferably, the nucleic acid molecule of the present invention is present as an integral part of a genetic construct (also commonly denoted as an "expression cassette") that enables its expression. A genetic construct is referred to as "capable of expressing a nucleic acid molecule" or capable "to allow expression of a nucleic acid (i.e. nucleotide) sequence" if it comprises sequence elements which contain information regarding to transcriptional and/or translational regulation, and if such sequences are "operably linked" to the nucleotide sequence encoding the peptide. An operable linkage is a linkage in which the regulatory sequence elements and the sequence to be expressed (and/or the sequences to be expressed among each other) are connected in a way that enables gene expression.

The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell. Suitable prokaryotic promoters include inter alia the lacUV5, trp, tet and tac promoters of $E.$ $coli$ and the T7 phage promoter Suitable eukaryotic promoters include inter alia the SV40 early and late promoters, the RSV and CMV promoters, and the yeast AOX1 and GAL1 promoters. In addition, the 3' non-coding sequences may contain regulatory elements involved in transcriptional termination, polyadenylation, or the like. If, however, these termination sequences are not satisfactory functional in a particular host cell, then they may be substituted with signals functional in that cell. The skilled person is well aware of all these regulatory elements, and the selection of such elements suitable for the expression of a nucleic acid molecule in a given setting is within his common knowledge.

The nucleic acid molecules of the invention, optionally as part of an expression cassette, may also be comprised in a vector or other cloning vehicle. Accordingly, in a further aspect, the present invention relates to a vector comprising the nucleic acid molecule of the present invention.

The vector of the invention may be, e.g., a plasmid, cosmid, phagemid, virus, bacteriophage, artificial chromosome, or another vehicle commonly used in genetic engineering. Preferably, the vector is an expression vector that is capable of directing the expression of the nucleic acid molecule of the invention. Such an expression vector can include, aside from the regulatory sequences described above and a nucleic acid sequence to be expressed, at least one origin of replication as well as control sequences derived from a species compatible with the host that is used for expression as well as one or more selection markers conferring a selectable phenotype on transfected cells. Specifically designed vectors (i.e. shuttle vectors) comprising more than one origin of replication allow the shuttling between different hosts, such as between bacteria and fungal cells or between bacteria and animal cells. Suitable origins of replication for prokaryotic cells include, for example, ColE1 and M13. An exemplary origin of replication in mammalian vectors is SV40. Suitable prokaryotic selection markers include inter alia the kanamycin, ampicillin, and tetracycline resistance genes. In eukaryotes, the dihydrofolate reductase gene and the glutamine synthase gene represent exemplary selection markers to be employed. Methods that can be used to design and/or modify recombinant vectors are well established in the art (see, e.g., Sambrook, J., and Russel, D. W. (2001), supra).

Large numbers of suitable vectors are commercially available and well known to the skilled person who is also able to determine which vectors are suitable for expressing a nucleic acid molecule of interest in a given setting. Examples of such vectors include inter alia prokaryotic vectors, such as the pUC-series, pBluescript, the pET-series, pCRTOPO, lambda gt11, the pBBR1-MCS series, and pBC2, as well as vectors compatible with expression in mammalian cells, such as pCEP4, pXT1, pSG5, pRSVneo, pSV2-dhfr, pcDNA3 pSIR, and pIRES-EGFP. Examples of plasmid vectors suitable for gene expression in $Pichia$ $pastoris$ include inter alia pAO815, pPIC9K, and pPIC3.5K.

Alternatively, the nucleic acid molecule of the present invention, as defined herein, may also be inserted into vectors such that a translational fusion with another nucleic acid molecule occurs. The other nucleic acid molecule may, e.g., encode a peptide or protein that increase the solubility and/or facilitate the purification of the peptide of the invention. Examples of such vectors include pET32, pET41, and pET43.

In another aspect, the present invention relates to a host cell comprising the vector as defined herein above.

Introduction of a nucleic acid vector into a host cell may be accomplished by means of various transformation, transduction or transfection methods, all of them well established in the art (see, e.g., Sambrook, J., and Russel, D. W. (2001), supra).

Within the present invention, the vector introduced may be propagated and maintained in the host cell as an independent genetic unit or it may become stably integrated into the host cell's genome via genetic recombination. Such recombination may either occur at random positions of the genome by non-homologous recombination or at specific positions of the genome by homologous recombination or via site-specific integrases.

The host cell of the present invention may be a prokaryotic or a eukaryotic cell, with the latter one being preferred. Suitable prokaryotic host cells include inter alia strains of $Escherichia$ $coli$ ($E.$ $coli$) (e.g., BL21, DH5α, XL-1-Blue, JM105, JM110, and Rosetta®), $Bacillus$ $subtilis,$ $Salmonella$ spec., and $Agrobacterium$ $tumefaciens$. Suitable eukaryotic host cells include inter alia yeasts (e.g., $Pichia$ $pastoris$ and $Saccharomyces$ $cerevisiae$), insect cells (e.g., $Drosophila$ $melanogaaster$ S2 cells and $Spodoptera$ $frugiperda$ Sf9 cells), and plant cells. Preferably, the eukaryotic host cells employed herein are mammalian cells, in particular human cells.

Suitable mammalian cells include inter alia immortalized cell lines such as human Hela, HEK293, H9, MCF7, and Jurkat cells, mouse NIH3T3, C127, and L cells, simian COS1 and COS7 cells, quail QC1-3 cells, and Chinese hamster ovary (CHO) cells. All these host cells may be obtained from depositories such as the American Type Culture Collection (Manassas, Va., USA) or the Deutsche Sammlung von Mikroorganismen and Zellkulturen (Braunschweig, Germany) as well as from various commercial suppliers. Also within the present invention are primary mammalian cells, that is, cells directly obtained from an organism (at any developmental stage including inter alia blastocytes, embryos, larval stages, and adults). Examples of suitable primary cells comprise cardiomyocytes, primary hepatocytes, fibroblasts, neuronal cells, as well as stem cells. Also within the present invention are immortalized stable cell lines derived from primary cells.

In some embodiments, the host cell of the present invention constitutes a part of a multi-cellular organism. In other words, the invention also relates to transgenic organisms comprising at least one host cell as defined herein. Preferably, the transgenic organism is a mammal, e.g., a mouse, rat, hamster, rabbit, cat, dog, pig, cow, horse, monkey or human.

In a further aspect, the present invention relates to a method of producing a peptide as defined herein, comprising:
(a) culturing the host cell of the invention under suitable conditions; and
(b) isolating the peptide produced.

A large number of suitable methods are available to produce peptides in appropriate host cells. If a unicellular host is employed, such as a prokaryote or a mammalian cell line, the person skilled in the art can revert to a variety of culture conditions. Conveniently, the peptide produced is harvested from the culture medium, lysates or extracts of the cultured cells or from isolated (biological) membranes by established techniques (see, e.g., Sambrook, J., and Russel, D. W. (2001), supra). In case, the host cell is part of a multi-cellular organism, a fraction of these cells may serve as source for isolating the peptide of the invention.

Appropriate culture media and conditions for the above-described host cells are well known in the art. For example, suitable conditions for culturing bacteria involve growing them under aeration in Luria Bertani (LB) medium. In order to increase the yield and the solubility of the expression product, the medium can be buffered or supplemented with suitable additives known in the art (such as chaperones, rare codon tRNAs, prostethic groups, co-factors, metal ions, and the like). Typically, *E. coli* can be cultured from 4° C. to 37° C., the exact temperature or sequence of temperatures depends on the molecule to be expressed. In general, the skilled person is also aware that these conditions may have to be adapted to the needs of the host and the requirements of the peptide or protein expressed. If an inducible expression system (e.g., the tetracycline-inducible Tet-On/Tet-Off system or the ecdysone-inducible system) is used to regulate expression of the nucleic acid molecule of interest in the host cell, expression can be induced by addition of an appropriate inducing agent.

Depending on the particular cell type employed and its specific growth requirements, mammalian cell culture can be performed, e.g., in RPMI 1640 medium or DMEM (Dulbecco's Modified Eagle Medium) supplemented with 10% (v/v) FCS (fetal calf serum), 2 mM L-glutamine, and 100 U/ml penicillin/streptomycin. Alternatively, a growth medium with a reduced serum concentration, such as OptiMEM, may be used. The cells may be incubated at 37° C. in a 5% $CO_2$, water saturated atmosphere.

Suitable media for insect cell culture include inter alia TNM supplemented with 10% FCS or SF900 medium. Insect cells are usually grown at 27° C. as adhesion or suspension cultures.

Suitable expression protocols for both prokaryotic and eukaryotic cells are well known in the art (see, e.g., Sambrook, J., and Russel, D. W. (2001), supra). The respective assay systems, kits, and reagents are commercially available from various suppliers.

An alternative method for producing the peptide molecules of the invention involves in vitro translation of mRNA. Suitable cell-free in vitro translation systems include inter alia rabbit reticulocyte lysate, wheat germ extract, canine pancreatic microsomal membranes, *E. coli* S30 extract, as well as coupled transcription/translation systems. Corresponding assay systems are commercially available from various suppliers.

Methods of isolation of the peptide produced are well known in the art and include inter alia ion exchange chromatography, affinity chromatography, gel filtration chromatography (size exclusion chromatography), high-pressure liquid chromatography (HPLC), reversed phase HPLC, disc gel electrophoresis, and immunoprecipitation (see, e.g., Sambrook, J., and Russel, D. W. (2001), supra).

In another aspect, the present invention relates to a composition (herein also referred to as "complex") comprising at least one peptide as defined herein above being attached to at least one other moiety (herein also referred to as "cargo"), the at least one other moiety preferably being any one of the group consisting of one or more nucleic acid molecules, one or more peptides or proteins, one or more small molecules, and one or more nanoparticles, wherein the attachment is accomplished by a linkage selected from the group consisting of a covalent linkage and a non-covalent linkage.

The term "attachment", as used herein, is to be understood in its broadest sense, that is, it refers to any type of molecular interaction between two or more compounds. The term "covalent linkage" refers to an intra-molecular form of chemical bonding characterized by the sharing of one or more pairs of electrons between two components, producing a mutual attraction that holds the resultant molecule together. The term "non-covalent linkage" refers to a variety of interactions that are not covalent in nature, between molecules or parts of molecules that provide force to hold the molecules or parts of molecules together usually in a specific orientation or conformation. Such non-covalent interactions include inter alia ionic bonds, hydrophobic interactions, hydrogen bonds, Van-der-Waals forces, and dipole-dipole bonds. In case of a covalent linkage, the peptide of the invention may be directly coupled to the at least one other moiety or via a linker molecule that serves to physically separate the peptide of the invention and the at least one other moiety and thus to ensure that neither entity is limited in their function due to the close vicinity to the other. Depending on the at least one other moiety, the linker may be, e.g., a peptide bond, an amino acid, a peptide of appropriate length, or a different molecule providing the desired features. In specific embodiments, the linker is a lysine or an arginine residue whose ε-amino groups are suitable to couple the peptides as defined herein to various other moieties. The skilled person knows how to design appropriate linker molecules, in particular linker peptides based on his common knowledge. For example, peptide linkers can be chosen from the LIP (Loops in Proteins) database (Michalsky, E. et al. (2003) *Prot. Eng.* 56, 979-985). Such linker may be attached to the N- or the C-terminus or, if deemed suitable, also to a non-terminal amino acid residue of the peptide of the present invention.

In preferred embodiments, the at least one peptide as defined herein above is attached to the at least one other moiety via a non-covalent interaction, for example, via a (reversible) complex formation.

In other particular embodiments, the at least one peptide as defined herein above is attached to the at least one other moiety via a covalent interaction, for example, in form of a fusion molecule. The term "fusion molecule, as used herein, denotes an at least bipartite molecule comprising a peptide of the invention coupled to at least one other moiety, thus forming a single entity. The peptide and the at least one other moiety may be separated by a linker as described above or may be directly coupled. The at least one other moiety may be fused to the peptide of the invention at the N-terminus, the C-terminus or any amino acid other than the terminal amino acids, with a fusion to the N-terminus being preferred. Additional moieties may be fused to the moiety already comprised in the fusion molecule. The skilled person is well aware of assays for determining the optimal order and/or combination of moieties in the fusion molecule of the invention. Typically, when the fusion molecule comprises a peptide of the invention and at least one other peptide, the term does not include fusion molecules, wherein the fusion results in naturally occurring peptides. Such fusion molecule can be produced and isolated according to the methods described above for the production of the peptides of the invention.

The composition of the invention may comprise one or more peptides as defined herein. In case of a plurality of at least two peptides, these may be of the same type or of different types. Vice versa, if the at least one peptide of the invention is attached to two or more other moieties, these moieties may be of the same type or of different types (e.g., two nucleic acid molecules or one nucleic acid molecule and one peptide molecule). In specific embodiments, a single peptide of the invention is attached to a plurality of two or more other moieties. In other embodiments, a plurality of two or more peptides of the invention is attached to a single other moiety.

In preferred embodiments, the at least one other moiety is selected from the group consisting of one or more nucleic acid molecules, one or more peptides or proteins, one or more small molecules, and one or more nanoparticles.

The composition according to the present invention may also comprise further components, for example, agents for stabilizing the attachment between the one or more peptides as defined herein and the at least one other moiety (e.g., chelating agents); agents for protecting the composition (e.g., against cellular nucleases); or agents for compensating a net charge of the composition in order to facilitate cellular uptake.

The term "small molecules", as used herein, is to be understood in its broadest meaning and does not only include low molecular weight organic compounds but also labels and reporter molecules (cf. below), haptens (i.e. a small molecule that can elicit an immune response only when attached to a larger carrier) such as hydralazine, urushiol, fluorescein, biotin, and digoxigenin, and aptamers.

The term "nanoparticles", as used herein, denotes microscopic particles with at least one dimension less than 100 nm. Typically, nanoparticles have a diameter in the range of 50 nm to 500 nm (i.e. 0.05 µm to 0.5 µm), are structurally stable in physiological environments, and are capable to house smaller molecules, such as drugs or other bioactive agents, which can then be delivered at the desired site. Many nanoparticles (or nanocarriers) are temperature-sensitive and/or pH-sensitive, that is, they release their cargo upon heating and/or a change in the pH. Such nanocarriers protect enclosed compounds against degradation and digestive fluids until they are released.

In specific embodiments, the at least one peptide of the invention that is comprised in the composition is attached to one or more nucleic acid molecules. Preferably, the at least one peptide of the invention to which the one or more nucleic acid molecules are attached has an amino acid sequence selected from the group consisting of SEQ ID NO: 2, SEQ ID NO: 3, SEQ ID NO: 4, and an amino acid sequence having over its total length at least 70%, preferably at least 80% overall sequence identity with any one of SEQ ID NO: 2 to SEQ ID NO: 4.

The one or more nucleic acid molecules to which the at least one peptide as defined herein is attached may be naturally occurring or artificial DNA molecules or RNA molecules of any length (including aptamers) that may be single-stranded or double-stranded. In embodiments with more than one nucleic acid molecules being attached to the at least one peptide, these nucleic acid molecule may be of the same type (i.e. have identical nucleotide sequences) or of different types. Typically, one peptide of the invention is attached to a single nucleic acid molecule.

In specific embodiments, the one or more nucleic acid molecules are RNA molecules, typically small non-coding RNA molecules (i.e. RNAs not translated into a peptide or protein such as snRNAs, snoRNAs, stRNAs, siRNAs, miRNAs, and shRNAs), and preferably the RNA molecules are selected from the group consisting of siRNA molecules, miRNA molecules, and shRNA molecules.

The term "miRNA molecule" (or "miRNA"), as used herein, is given its ordinary meaning in the art (reviewed, e.g. in Bartel, D. P. (2004) Cell 23, 281-292; He, L. and Hannon, G. J. (2004) Nat. Rev. Genet. 5, 522-531). Accordingly, the term "microRNA" denotes an endogenous RNA molecule derived from a genomic locus that is processed from transcripts that can form local RNA precursor miRNA structures. The mature miRNA is usually 20, 21, 22, 23, 24, or 25 nucleotides in length, although other numbers of nucleotides may be present as well, for example 18, 19, 26 or 27 nucleotides.

The miRNA encoding sequence has the potential to pair with flanking genomic sequences, placing the mature miRNA within an imperfect RNA duplex (herein also referred to as stem-loop or hairpin structure or as pre-miRNA), which serves as an intermediate for miRNA processing from a longer precursor transcript. This processing typically occurs through the consecutive action of two specific endonucleases termed Drosha and Dicer, respectively. Drosha generates from the primary transcript (referred to as "pri-miRNA") a miRNA precursor (herein also denoted "pre-miRNA") that typically folds into a hairpin or stem-loop structure. From this miRNA precursor a miRNA duplex is excised by means of Dicer that comprises the mature miRNA at one arm of the hairpin or stem-loop structure and a similar-sized segment (commonly referred to miRNA*) at the other arm. The miRNA is then guided to its target mRNA to exert its function, whereas the miRNA* is degraded in most cases. Depending on the degree of complementarity between the miRNA and its target, miRNAs can guide different regulatory processes. Target mRNAs that are highly complementary to miRNAs are specifically cleaved by mechanisms identical to RNA interference (RNAi) and the miRNAs function as short interfering RNAs (siRNAs). Target mRNAs with less complementarity to miRNAs are either directed to cellular degradation pathways and/or are translationally repressed. However, the mechanism of how miRNAs repress translation of their target mRNAs is still a matter of controversy.

In some embodiments, the one or more nucleic acid molecules attached to the at least one peptide molecule as defined herein are mature miRNA molecules. In other embodiments, miRNA precursor molecules are employed. The term "miRNA precursor" (or "precursor miRNA" or "pre-miRNA"), as used herein, refers to the portion of a miRNA primary transcript from which the mature miRNA is processed. Typically, the pre-miRNA folds into a stable hairpin (i.e. a duplex) or a stem-loop structure. The hairpin structures range from 50 to 120 nucleotides in length, typically from 55 to 100 nucleotides, and preferably from 60 to 90 nucleotides (counting the nucleotide residues pairing to the miRNA (i.e.

the "stem") and any intervening segment(s) (i.e. the "loop") but excluding more distal sequences).

The term "siRNA molecule" (or "siRNA"), as used herein, is also given its ordinary meaning in the art (reviewed, e.g., in Dorsett, Y. and Tuschl, T. (2004) Nat. Rev. Drug Disc. 3, 318-329; Rana, T. M. (2007) Nat. Rev. Mol. Cell. Biol. 8, 23-36). Accordingly, a "siNA" denotes a double-stranded RNA molecule, typically having 2 nucleotides overhang at their 3'-ends and phosphate groups at their 5'-ends. A mature siRNA is usually 20, 21, 22, 23, 24, or 25 nucleotides in length, although other numbers of nucleotides may be present as well, for example 18, 19, 26 or 27 nucleotides. Within the present invention, siRNA precursor molecules having a length of up to 49 nucleotides may be employed as well. The mature siRNA is processed from such precursor by Dicer.

Traditionally, the term "siRNA" was used to refer to interfering RNAs that are exogenously introduced into cells. In the meantime, endogenous siRNAs have been discovered in various organisms and fall into at least four classes: trans-acting siRNAs (tasiRNAs), repeat-associated siRNAs (rasiRNAs), small-scan (scn)RNAs and Piwi-interacting (pi)RNAs (reviewed, e.g., in Rana, T. M. (2007) supra).

One strand of the siRNA is incorporated into a ribonucleoprotein complex known as the RNA-induced silencing complex (RISC). RISC uses this siRNA strand to identify mRNA target molecules that are at least partially complementary to the incorporated siRNA strand, and then cleaves these target mRNAs. The siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of a siRNA can be incorporated into RISC and function as a guide strand. However, siRNA design (e.g., decreased siRNA duplex stability at the 5' end of the desired guide strand) can favor incorporation of the desired guide strand into RISC. The antisense strand of a siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein.

The term "shRNA molecule" (i.e. short hairpin RNA molecule), as used herein, denotes an artificial single-stranded interfering RNA molecule comprising both sense and antisense strand of a "siRNA duplex" in a stem-loop or hairpin structure. The stem of this hairpin structure typically ranges from 19 to 29 nucleotides in length, and a loop typically ranges from 4 to 15 nucleotides in length (see, e.g., Siolas, D. et al. (2004) Nat. Biotechnol. 23, 227-231). Usually, a shRNA molecule is encoded within a DNA expression vector under the control of a RNA polymerase III promoter (e.g., the U6 promoter).

In some embodiments, the RNA molecules described above comprise a backbone structure exclusively comprising ribonucleotide units. In other embodiments, such a RNA molecule comprises at least one ribonucleotide backbone unit and at least one deoxyribonucleotide backbone unit. Furthermore, the RNA molecule may contain one or more modifications of the ribose 2'-OH group into a 2'-O-methyl group or 2'-O-methoxyethyl group (also referred to as "2'-O-methylation"), which prevented nuclease degradation in the culture media and, importantly, also prevented endonucleolytic cleavage by the RNA-induced silencing complex nuclease, leading to irreversible inhibition of the small RNA molecule. Another possible modification, which is functionally equivalent to 2'-O-methylation, involves locked nucleic acids (LNAs) representing nucleic acid analogs containing one or more LNA nucleotide monomers with a bicyclic furanose unit locked in an RNA-mimicking sugar conformation (cf., e.g., Orom, U. A. et al. (2006) Gene 372, 137-141).

In some other embodiments, the nucleic acid molecules to be attached to the at least one peptide molecule of the invention represent silencers of endogenous miRNA expression. One example of such silencers are chemically engineered oligonucleotides, named "antagomirs", which represent single-stranded 23-nucleotide RNA molecules conjugated to cholesterol (Krutzfeldt, J. et al. (2005) Nature 438, 685-689). Alternative to such chemically modified oligonucleotides, microRNA inhibitors that can be expressed in cells as RNAs produced from transgenes were generated. Termed "microRNA sponges", these competitive inhibitors are transcripts expressed from strong promoters, and containing multiple tandem-binding sites to a microRNA of interest (Ebert, M. S. et al. (2007) Nat. Methods 4, 721-726).

In specifically preferred embodiments, the at least one peptide comprised in the composition is attached to one or more other peptides. The term "other peptides", as used herein, denotes that these peptides are different from the peptides capable of being internalized into a cell as defined herein (i.e. the peptides specified in the claims).

Particularly preferably, the at least one peptide of the invention to which the one or more other peptide molecules are attached has an amino acid sequence selected from the group consisting of SEQ ID NO: 2, SEQ ID NO: 3, SEQ ID NO: 4, and an amino acid sequence having over its total length at least 70%, preferably at least 80% overall sequence identity with any one of SEQ ID NO: 2 to SEQ ID NO: 4.

The one or more other peptides to which the at least one peptide as defined herein is attached may be naturally occurring or artificial molecules of any length. For example, the length of such other peptides may range from 2 to 500 amino acids or from 5 to 200 amino acids. Typically, such peptides have a length between 8 and 100 amino acids or from 10 and 50 amino acids. Preferably, the length of such peptides may range from 10 to 40 amino acids, from 12 to 35 amino acids or from 15 to 30 amino acids. Artificial peptide molecules may be obtained by chemical synthesis, by means of recombinant DNA technology or a combination thereof. All these synthesis methods are well established in the art (see, e.g., Sambrook, J., and Russel, D. W. (2001), supra).

In embodiments with more than one other peptide molecules being attached to the at least one peptide of the invention, these other peptide molecules may be of the same type (i.e. have identical amino acid sequences) or of different types. Typically, one peptide of the invention is attached to a single other peptide molecule.

In further embodiments, the one or more other peptide molecules comprise at least one structured domain, that is, an element that forms (i.e. folds into) a stable secondary structure, that is, a particular spatial arrangement of amino acid residues that are located in proximity to each in the linear sequence. Often, the steric relationships between amino acid residues are of a regular kind, giving rise to periodic structures well known in the art such as α-helices (a rod-like tightly coiled structure) and β-strands (an extended stretch, with multiple such stretches optionally forming parallel or anti-parallel β-sheets). The peptide molecules may comprise one such structured domain encompassed in an unstructured surrounding or may comprise two or more such structured domains (of the same type or of different types, e.g., two α-helices or one α-helix and one β-strand) separated from each other. The peptide molecules may form such a secondary structure over its entire length (i.e. does not comprise unstructured regions). In case of more than one other peptide molecules being comprised in the composition as defined herein, it is also possible that part of the other peptide molecules comprises at least one structured domain, whereas the remaining part is unstructured.

In preferred embodiments, at least a part of the one or more other peptide molecules as defined herein forms an alpha-helical secondary structure. The α-helical element may comprise at least 4 or 6 amino acid residues, and preferably at least 8 or 10 amino acid residues. In specific embodiments, the peptide molecule of the invention comprises a single a-helical element as the only secondary structure.

In other particular embodiments, the one or more other peptides are pro-apoptotic peptides, that is, peptides being capable of inducing and/or modulating apoptosis (i.e. programmed cell death). The skilled person is well aware of protein factors that are responsible for the onset and/or mediation of apoptosis as well as of suitable means for selecting peptide sequences that retain the pro-apoptotic functionality. For example, such pro-apoptotic factors may be retrieved from the scientific literature as well as various databases such as the 'APOPTOSIS Database' (Doctor, K. S. et al. (2003) *Cell Death Diff.* 10, 621-623).

In other embodiments, the one or more other peptides have functionalities being selected from the group consisting of activation/derepression of cellular tumor suppressors, inhibition of cellular oncogenes, and inhibition of constitutively active protein variants. In yet other embodiments, the one or more peptides represent naturally occurring or synthetic ligands (e.g., agonists and antagonists) of cellular receptors such as cytokine receptors, angiotensin receptors, endothelin receptors, vasopressin receptors, and bradykinin receptors. Again, numerous such peptides are well known in the art or can be readily retrieved from various resources.

In a further aspect, the present invention relates to a method of producing the composition as defined herein above, comprising:
(a) providing at least one peptide of the invention; and
(b) contacting the at least one peptide with any one of the group consisting of one or more nucleic acid molecules, one or more peptides or proteins, one or more small molecules, and one or more nanoparticles, thus allowing for forming an attachment.

The skilled person is well aware of suitable reaction conditions for performing such method (see, e.g., Sambrook, J., and Russel, D. W. (2001), supra; Ausubel, F. M. et al. (2001) supra). In a further aspect, the present invention relates to a method of detecting the internalization behavior of the peptide of the invention or the composition (i.e. at least one peptide attached to a cargo) of the invention, comprising:
(a) administering the peptide or the composition to one or more cells; and
(b) detecting the internalization of the peptide or the composition.

The method may be particularly suitable to estimate the applicability of the peptide or composition for medical (e.g., diagnostic) or research purposes. If efficient internalization of the peptide or the composition is detected and, optionally, its localization is in the cytoplasm, this indicates that the respective compound can be used in a particular application.

To this end, the peptide or composition of the invention may be fused to one or more detectable labels. Labels that may be used according to the invention include any compound, which directly or indirectly generates a detectable compound or signal in a chemical, physical or enzymatic reaction. Labeling and subsequent detection can be achieved by methods well known in the art (see, for example, Sambrook, J., and Russel, D. W. (2001), supra; and Lottspeich, F., and Zorbas H. (1998) *Bioanalytik*, Spektrum Akademischer Verlag, Heidelberg/Berlin, Germany). The labels can be selected inter alia from fluorescent labels, enzyme labels, chromogenic labels, luminescent labels, radioactive labels, haptens, biotin, metal complexes, metals, and colloidal gold. All these types of labels are well established in the art and can be commercially obtained from various suppliers. An example of a physical reaction that is mediated by such labels is the emission of fluorescence or phosphorescence upon irradiation. Alkaline phosphatase, horseradish peroxidase, β-galactosidase, and β-lactamase are examples of enzyme labels, which catalyze the formation of chromogenic reaction products, and which may be used in the invention.

In another aspect, the present invention relates to the use of the peptide as defined herein or the composition as defined herein for the transformation or transfection of one or more cells, that is, the application of said compounds as delivery vehicle for the transport of a cargo into particular target cells.

In specific embodiments, the invention relates to the use of a composition as defined herein above comprising at least one peptide of the invention being attached to at least any one of the group consisting of one or more nucleic acid molecules and one or more peptides or proteins for the transfection of and/or targeted delivery of agents to particular cells.

In yet another aspect, the present invention relates to a pharmaceutical composition comprising at least one peptide molecule as defined herein or the composition as defined herein (i.e. at least one peptide attached to a cargo) and optionally further comprising one or more pharmaceutically acceptable excipients and/or additives.

The term "pharmaceutical composition", as used herein, relates to a composition for administration to a subject, preferably to a human patient. Pharmaceutical compositions according to the present invention include any pharmaceutical dosage forms established in the art, such as inter alia capsules, microcapsules, cachets, pills, tablets, powders, pellets, multi-particulate formulations (e.g., beads, granules or crystals), aerosols, sprays, foams, solutions, dispersions, tinctures, syrups, elixirs, suspensions, water-in-oil emulsions such as ointments, and oil-in water emulsions such as creams, lotions, and balms. The formulations may be packaged in discrete dosage units or in multi-dose containers.

The pharmaceutical compositions of the invention include formulations suitable for oral, rectal, nasal, topical (including buccal and sub-lingual), peritoneal and parenteral (including intramuscular, subcutaneous and intravenous) administration, or for administration by inhalation or insufflation. Administration may be local or systemic.

The pharmaceutical compositions can be prepared according to established methods (see, for example, Gennaro, A. L. and Gennaro, A. R. (2000) *Remington: The Science and Practice of Pharmacy*, 20th Ed., Lippincott Williams & Wilkins, Philadelphia, Pa.; Crowder, T. M. et al. (2003) *A Guide to Pharmaceutical Particulate Science*. Interpharm/CRC, Boca Raton, Fla.; Niazi, S. K. (2004) *Handbook of Pharmaceutical Manufacturing Formulations*, CRC Press, Boca Raton, Fla.).

For the preparation of said compositions, one or more pharmaceutically acceptable (i.e.) inert inorganic or organic excipients (i.e. carriers) can be used. To prepare, e.g., pills, tablets, capsules or granules, for example, lactose, talc, stearic acid and its salts, fats, waxes, solid or liquid polyols, natural and hardened oils may be used. Suitable excipients for the production of solutions, suspensions, emulsions, aerosol mixtures or powders for reconstitution into solutions or aerosol mixtures prior to use include inter alia water, alcohols, glycerol, polyols, and suitable mixtures thereof as well as vegetable oils. The pharmaceutical composition may also contain additives, such as, for example, fillers, binders, wetting agents, glidants, stabilizers, preservatives, emulsifiers, and furthermore solvents or solubilizers or agents for achieving a depot effect. The latter is to be understood that the active peptides or compositions of the invention may be incorporated into slow or sustained release or targeted delivery systems, such as liposomes, nanoparticles, and microcapsules.

The pharmaceutical composition of the invention will be administered to the subject at a suitable dose. The particular dosage regimen applied will be determined by the attending physician as well as clinical factors. As is well known in the medical arts, an appropriate dosages for a given patient depend upon many factors, including the patient's size, sex, and age, the particular compound to be administered, time and route of administration, general health, pre-existing conditions, and other drugs being administered concurrently. The therapeutically effective amount for a given situation will readily be determined by routine experimentation and is within the skills and judgment of the ordinary clinician or physician. Generally, the dosage as a regular administration should be in the range of 1 µg to 1 g per day. However, a preferred dosage might be in the range of 0.01 mg to 100 mg, a more preferred dosage in the range of 0.01 mg to 50 mg and a most preferred dosage in the range of 0.01 mg to 10 mg per day.

In yet another aspect, the present invention relates to the peptide as defined herein or the composition as defined herein for use in the prevention and/or treatment of a condition, the condition preferably being selected from the group consisting of cancer, immune diseases, cardiovascular diseases, neuronal diseases, infections, and inflammatory diseases. For this purpose, the peptide or composition of the invention may be formulated to a pharmaceutical composition as defined herein above and administered to a subject, preferably to a human patient.

The term "cancer", as used herein, denotes any type or form of malignant neoplasm characterized by uncontrolled division of target cells based on genetic re-programming and by the ability of the target cells to spread, either by direct growth into adjacent tissue through invasion, or by implantation into distant sites by metastasis (where cancer cells are transported through the bloodstream or lymphatic system). Examples include inter alia breast cancer, colorectal cancer, prostate cancer, leukemia, lymphomas, neuroblastoma, glioblastoma, melanoma, liver cancer, and lung cancer.

The term "immune disease", as used herein, refers to any disorder of the immune system. Examples of such immune diseases include inter alia immunodeficiencies (i.e. congenital or acquired conditions in which the immune system's ability to fight infectious diseases is compromised or entirely absent, such as AIDS or SCID), hypersensitivity (such as allergies or asthma), and autoimmune diseases. The term "autoimmune disease", as used herein, is to be understood to denote any disorder arising from an overactive immune response of the body against endogenic substances and tissues, wherein the body attacks its own cells. Examples of autoimmune diseases include inter alia multiple sclerosis, Crohn's disease, lupus erythematosus, myasthenia gravis, rheumatoid arthritis, and polyarthritis.

The term "cardiovascular disease", as used herein, refers to any disorder of the heart and the coronary blood vessels. Examples of cardiovascular diseases include inter alia coronary heart disease, angina pectoris, arteriosclerosis, cardiomyopathies, myocardial infarction, ischemia, and myocarditis.

The term "neuronal disease" (or "neurological disorder), as used herein, refers to any disorder of the nervous system including diseases of the central nervous system (CNS) (i.e. brain and spinal cord) and diseases of the peripheral nervous system. Examples of CNS diseases include inter alia Alzheimer's disease, Parkinson's disease, Huntington's disease, Locked-in syndrome, and Tourettes syndrome. Examples of diseases of the peripheral nervous system include, e.g., mononeuritis multiplex and polyneuropathy.

The term "infection", as used herein, refers to any disorder based on the colonization of a host organism by a foreign pathogen such as bacteria, viruses or fungi. Examples of bacterial infections include inter alia bacterial meningitis, cholera, diphtheria, listeriosis, whooping cough, salmonellosis, tetanus, and typhus. Examples of viral infections include inter alia common cold, influenza, dengue fever, Ebola hemorrhagic fever, hepatitis, mumps, poliomyelitis, rabies, and smallpox. Examples of fungal infections include inter alia tinea pedis, blastomycosis, and candidiasis.

The term "inflammatory disease", as used herein, refers to any disorder associated with inflammation including, e.g., acne, asthma, hay fever, arthritis, inflammatory bowel disease, pelvic inflammatory disease, and transplant rejection.

In a further aspect, the present invention relates to a method for the prevention and/or treatment of a condition selected from the group consisting of cancer, immune diseases, cardiovascular diseases, neuronal diseases, infections, and inflammatory diseases, comprising: administering at least one peptide of the invention or the composition of the invention to a subject. Preferably, the subject is a human patient.

In a final aspect, the present invention relates to a kit-of-parts comprising at least any one of:
(a) the peptide molecule as defined herein above;
(b) the nucleic acid molecule as defined herein above;
(c) the vector as defined herein above;
(d) the host cell as defined herein above; and
(e) the composition as defined herein above.

The various components (a) to (e) of the kit may be packaged in one or more containers, such as one or more vials. For example, each component comprised in the kit may be packaged in a separate container.

The above components of the kit may be provided in lyophilized or dry form or dissolved in a suitable buffer such as phosphate-buffered saline or Tris/EDTA (TE)-buffer. The host cell of the present invention may be provided, e.g., as a "step culture", streaked on an agar plate or any other form suitable for long-term storage. Such storage methods are well established in the art.

The kit may also comprise additional reagents including inter alia preservatives, growth media and/or buffers for storage and/or reconstitution of the above-referenced components, washing solutions, and the like. These reagents may be provided in combination with one or more of the components (a) to (e), that is, in the same container (e.g. a peptide or nucleic acid molecule dissolved in an appropriate buffer). Alternatively, at least some of these additional reagents may be provided in separate containers.

The invention is further described by the figures and the following examples, which are solely for the purpose of illustrating specific embodiments of this invention, and are not to be construed as limiting the scope of the invention in any way.

EXAMPLES

Example 1

Materials and Methods 1.1 Mammalian Cell Culture

MCF7 cells were seeded at a density of 15.000 cells per well in 96 well plates. The cells were incubated for 24 hours at 37° C., 5% $CO_2$ and 85% humidity in RPMI 1640 medium supplemented with 10% FCS (fetal calf serum) and L-glutamine. For functional assays, the cells were washed in OptiMEM medium and RPMI 1640 was replaced with Opti-MEM (all reagents were purchased from Invitrogen Corporation, Carlsbad, Calif., USA). Complexes of siRNAs and peptides were formed by incubation of 100 nM siRNA with the indicated peptide concentrations in OptiMEM for 30 minutes at room temperature. The complexes were added to the cells and incubated for 3 hours. Subsequently, OptiMEM was replaced with normal RPMI 1640 growth medium. The cells were incubated for further 21 hours for generating bDNA lysates, and for further 45 hours for performing CellTiter-Glo or CytoTox-Glo assays (cf. below).

1.2 Quantification of mRNA Levels

For the quantification of cellular mRNA levels bDNA (branched DNA) assays were performed which enable the detection of individual mRNA levels. To this end, a defined number of the cells to be analyzed was seeded into 96-well plates and allowed to attach over night. On the next day, the cells were transfected with siRNA.

After further 24 hours, the mRNA species were quantified using the QuantiGene Plex 2.0 assay kit according to the manufacturer's instructions (Affymetrix Inc., Santa Clara, Calif., USA). In brief, cell lysates were transferred to a capture plate in the presence of a gene-specific probe set and incubated at 53° C. over night. After washing, the wells were sequentially incubated at 53° C. with an amplifier agent and an alkaline phosphatase (AP)-linked label probe with a washing step in between. Subsequently, the luminescent AP substrate dioxitane was added and incubated for 30 min at 53° C. Luminescence was assayed using an InfiniteF200 luminescence reader (Tecan Austria GmbH, Gröding, Austria).

1.3 Cell Viability Assays

In order to measure the number of living cells the CellTiter-Glo Luminescent Cell Viability Assay (Promega Corporation, Madison, Wis., USA) was used according to the protocol of the manufacturer. The cells were incubated for 48 hours in the presence of peptides and siRNAs. Subsequently, the cells are lysed, and a luminescent signal proportional to the amount of ATP present is generated which, in turn, is proportional to the number of living cells present. Luminescence was analyzed in an InfiniteF200 luminescence reader.

1.4 Cytotoxicity Assays

In order to the cytotoxicity of the peptides the CytoTox-Glo Cytotocity Assay (Promega Corporation, Madison, Wis., USA) was used according to the protocol of the manufacturer. The cells were incubated for 48 hours in the presence of peptides and siRNA. Then, the cells were treated with a luminogenic peptide substrate in order to measure dead-cell protease activity, which is released from cells that have lost membrane integrity. The substrate cannot cross the intact membrane of live cells and does not generate any appreciable signal from the live-cell population. The luminescence of this assay therefore represents dead cells. The 96 well plates were then analyzed in an InfiniteF200 luminescence reader.

1.5 Peptide Synthesis

Peptide synthesis was performed according to established protocols (FastMoc 0.25 mmol) in an automated Applied Biosystems ABI 433A peptide synthesizer using Fmoc chemistry. In iterative cycles, the respective peptide sequences were assembled via the sequential coupling of the corresponding Fmoc amino acids.

In each coupling step, the N-terminal Fmoc group was removed by treatment of the resin with 20% piperidine in N-methylpyrrolidone. Couplings were carried out employing Fmoc protected amino acids (1 mmol) activated by HBTU/HOBt (1 mmol each) and DIPEA (2 mmol) in DMF. After a coupling step, unreacted amino groups were capped by treatment with a mixture of Ac2O (0.5 M), DIPEA (0.125 M) and HOBt (0.015 M) in NMP. Between two steps, the resin was extensively washed with N-methyl-pyrrolidone and DMF. Incorporation of sterically hindered amino acids was accomplished in automated double couplings. For this purpose, the resin was treated twice with 1 mmol of the activated building block without an intermediate capping step. Upon completion of the target sequences, Fmoc-12-amino-4,7,10-trioxadodecanoic acid (TEG-spacer) was coupled to the peptides using standard reaction conditions. Subsequently, Fmoc-Cys(Trt)-OH was attached to the amino terminus of all peptide sequences. After final Fmoc deprotection, the peptide resin was placed into a filter frit and treated with a mixture of tri-fluoroacetic acid, water and tri-isopropyl-silane (ratio of 19 ml to 0.5 ml to 0.5 ml) for 2.5 h. The cleavage solution was filtered and the peptides were precipitated by addition of cold (0° C.) di-isopropyl ether (300 ml) to yield a colorless solid, which was repeatedly washed with di-isopropyl ether. The crude product was re-dissolved in a mixture of acetic acid and water, lyophilized and purified by preparative reversed phase HPLC employing an acetonitrile/water gradient containing 0.1% TFA (Chromolith prep RP-18e column, 100×25 mm; Merck KGaA, Darmstadt, Germany).

1.6 FACS Analysis

For FACS analysis, MCF7 cells (ATCC number HTB-22) were detached by 15 min incubation in accutase (an enzyme solution having proteolytic and collagenolytic activities; commercially available from various suppliers). After washing in FACS buffer (PBS containing 5% FCS), the cells were seeded in a 96 well, rounded bottom multi-well plate (Cat. No. 3799, Corning Inc., Corning, N.Y. USA) in a final density of $3 \times 10^5$ cells/ml and used immediately. The cells were incubated in the respective presence of 1 µM, 5 µM and 10 µM FITC-labeled peptides in OptiMEM medium for 3 hours at 37° C. Afterwards, the cells were washed in FACS buffer and incubated in proteinase K (0.02 mg/ml) containing buffer for 30 minutes at 37° C. The cells were washed twice and analyzed with the FACSCanto II (BD Biosciences; San Jose, Calif., USA) using the FITC channel.

1.7 Gel-Shift Assays

Gel-shift assays were performed by mixing 500 µg siRNA duplex with the respective peptides in a given molar ratio in water. The complexes were formed for 1 hour at 37° C. and analyzed on a 2.5% agarose gel with ethidium bromide (run: 40 minutes at 125 V). For proteinase K treatment, 1 µl proteinase K was added to a standard reaction as indicated above.

Example 2

Identification of Potential Human CPPs 2.1 Bioinformatics Approach

Figure 1:
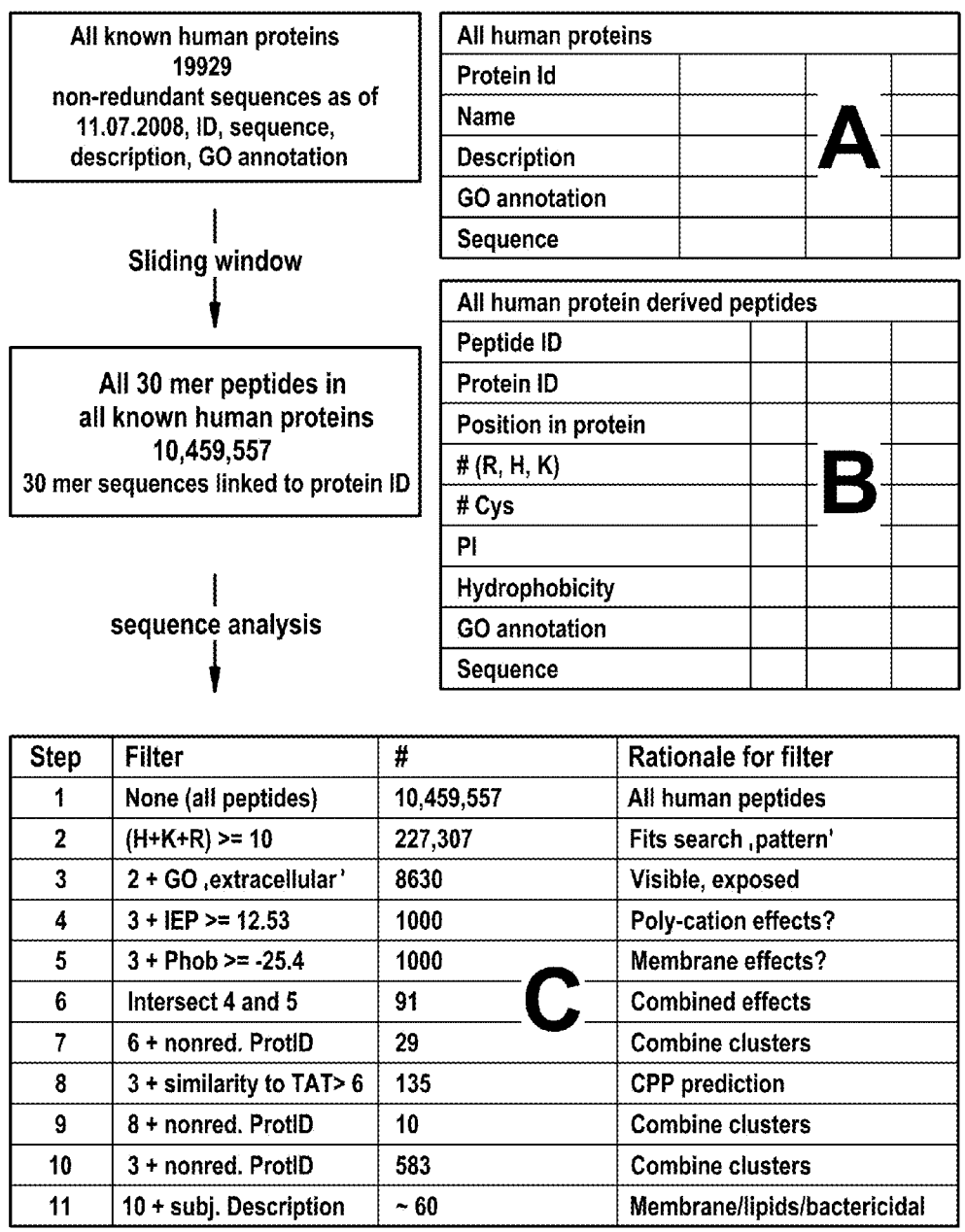
FIG. 1: Bioinformatics Approach for the Identification of Human Cell-Penetrating Peptides.

One group of cell-penetrating peptides (CPPs), exemplified by the HIV derived TAT (Frankel, A. D. and Pabo, C. O. (1988) *Cell* 55, 1189-1193; Vives; E. et al. (1997), supra) and the model peptide Poly-arginine (Wender, P. A. et al. (2000) *Proc. Natl. Acad. Sci. USA* 97, 13003-13008; Futaki, S. et al. (2001) *J. Biol. Chem.* 276, 5836-5840), is characterized by a high content of positively charged amino acids. Other CPPS, so called tilted peptides, are composed of both charged, hydrophilic stretches and uncharged lipophilic stretches of amino acids (Lins, L. et al. (2008) *Biochim. Biophys. Acta* 1778, 1537-1544). It is thus tempting to speculate that CPPs should have both of these characteristics. To identify such sequences in the human proteome a bioinformatics approach was employed. FIG. 1 depicts a schematic illustration of the workflow used to generate candidate lists of peptides.

To generate a library of peptides a sliding window approach was used. A window size of 30 amino acids was chosen and applied to all entries of the SwissProt protein database (Swiss Institute of Bioinformatics; http://www.expasy.org/sprot/). This resulted in a library of 10,459,557 individual peptides with 1,024,818 being unique. 163,887 peptides were found more than once, on average 2.7 times, which reflects the repetitive nature of several proteins. Within the generated library, each individual peptide sequence is linked to its corresponding source information (sequence of the peptide, source protein and position within the protein), as well as Gene Ontology (GO) annotations (Ashburner, M. et al. (2000) *Nat. Genet.* 25, 25-39) of the source protein. Additional information associated with each peptide includes its amino acid composition such as number of charges, isoelectric point (IEP), and predicted hydrophobicity. The rationale for using a sliding window of 30 amino acids was to generate larger peptides than usually used for CPPs as a larger peptide has a higher probability of being structured in terms of secondary structure (e.g., alpha-helices or beta-sheets). Peptides comprising such secondary structures were shown to be advantageous for cell penetration as compared to unstructured peptides (Deshayes, S. et al. (2004) *Biochemistry* 43, 7698-7706). Furthermore, alpha-helical peptides less than 12 amino acids in length were reported to have a decreased ability to interact with, and thus to transfect nucleic acid molecules (Niidome, T. et al. (1999) *Bioconjug. Chem.* 10, 773-780).

In a further step, peptides comprising in their primary amino acid sequence more than 30% positively charged amino acid residues (i.e., arginine (R), histidine (H), and lysine (K)) were filtered in order to generate peptides with higher similarity to the positive charged model peptides TAT and Poly-Arg. This filter resulted in 227,307 individual peptides. To enrich the selection obtained for peptides that have a higher potential of being tolerated by the immune system (i.e. that have a lower probability to be immunogenic) the results were aligned to the GO of the corresponding protein entries and restricted to extracellular proteins. In the end, this filter (i.e. the selection of candidates derived from human extracellular proteins that are thus "visible" to the human immune system) drastically reduced the number of peptides from 8630 to 583 individual proteins.

2.2 Selection of Peptide Candidates for Experimental Characterization

A major factor for reducing the number of peptide candidates was a shift from in silico approaches (with virtually no limitations in numbers of samples that can be analyzed) to experimental wet-lab analyses (only limited number of candidates that can be addressed comprehensively). Furthermore, another practical consideration to shorten the list of candidates was ease of handling, applicability in biological assays, and finally feasibility to develop a pharmacologically active compound. In the other hand, peptide sequences that are obviously poorly soluble or difficult to synthesize were excluded from further evaluation.

In order to avoid that candidate selection at this final step is determined by a single, or possibly two, stringent parameters the final candidate list for experimental evaluation was compiled by means of three different approaches:

One subset of candidate peptides is characterized by comprising not only at least 30% positively charged ("KHR30") but also many hydrophobic residues. Hence, the peptides were ranked with respect to their IEP as well as their hydrophobicity. The intersection of the 1000 peptides with the highest score for both lists resulted in 91 peptides derived from 29 proteins. Finally, 20 peptides derived from the 20 proteins with the highest intersection values were selected.

A second subset of candidates was generated based on the similarity to the TAT peptide sequence. All peptides were subjected to a homology comparison using the FASTA algorithm (Lipman, D. J. and Pearson, W. R. (1985), supra). The peptides were ranked according to their respective E-value (the lower the E-value, the higher the ranking). This approach yielded 135 peptides derived from 10 proteins. Finally, 5 peptides derived from 5 proteins were chosen for further analysis.

As a third subset, 36 candidate peptides derived from 25 individual proteins were chosen for experimental evaluation based on literature analyses relating to the function(s) of their source proteins. The discrepancy in number of peptides to number of proteins is explained by the use of multiple sequences from one protein (e.g., CO9_mot1a, CO9_mot1b) or different variants of one sequence (e.g., including or lacking disulfide bridges, such as Granulysin WT, Granulysin G8, Granulysin G9). In general, the length of 30 amino acid residues was maintained, but if a known motif was identified to contain such a 30mer, the length of the peptide was extended to 39 amino acid residues as in FALL (Yang, Y. X. et al. (2004) *Acta Pharmacol. Sin.* 25, 239-245) or 48 amino acid residues as in LIP_Cons_C_WT, a consensus sequence for multiple lipases (Demant, T. et al. (1988) *J. Lipid Res.* 29, 1603-1611). The restriction was based on a careful analysis of the literature and BLAST results obtained for these sequences. Preferred were: peptides derived from proteins known to interfere with membranes like factors of the complement system; peptides derived from proteins that degrade lipids (such as lipases); peptides derived from proteins that give rise to bactericidal factors such as FALL (Nijink, A. and Hancock, R. E. (2009) *Curr. Opin. Hematol.* 16, 41-47) or BPIL3 (Mulero, J. J. et al. (2002) *Immunogenetics* 54, 293-300); and peptides similar to those reported to act as CPPs (Takeshima, K. et al. (2003) *J. Biol. Chem.* 278, 1310-1315; Arrighi, R. B. et al. (2008) *Antimicrob. Agents Chemother.* 52, 3414-3417).

All peptides (incl. controls) that were subjected to further experimental evaluation are listed in Table 1.

For visual demonstration of the initial filter, the IEP of the peptides was plotted against their hydrophobicity. Compared to 500 randomly selected peptides (out of the about $10 \times 10^6$), the initial filter obviously led to an accumulation of the peptides chosen (cf. FIG. 2). For further comparison, five positive control peptides (i.e. TAT, REV, protamine, Poly-Arg, and INF7) were also included. This analysis shows that the positively charged control peptides TAT, REV, protamine, and 10×Arg comply with the filter criteria, whereas INF7 as being a negatively charged and hydrophobic peptide is found at the other end of the scale.

In addition to the selected human-derived CPP candidates, eight peptides with reported CPP activities were included in the screen as controls (cf. Table 1). These peptides can form non-covalent complexes with nucleotides and have transfection capability: TAT, a CPP derived from the transactivating protein of HIV (Ignatovich, I. A. et al. (2003) *J. Biol. Chem.* 278, 42625-42636); REV, a TAT related peptide of HIV (Futaki, S. et al., supra); poly-Arg (Kim, W. J. et al. (2006) *Mol. Ther.* 14, 343-350) as the bona fide example of a positively charged peptide; crotamine (Nascimento, F. D. et al. (2007) *J. Biol. Chem.* 282, 21349-21360). Furthermore, truncated protamine (Song, E. et al. (2005) *Nat. Biotechnol.* 23, 709-717) and the N-terminus of perforin were included as examples of human peptides. Two further controls not falling in the class of TAT-like CPPs were Inf7, a peptide derived from influenza virus HA (a negatively charged and hydrophobic peptide; Plank, C. et al. (1994) *J. Biol. Chem.* 269, 12918-12924) and MTS (a mainly hydrophobic peptide; Lin, Y. Z. et al. (1995) *J. Biol. Chem.* 270, 14255-14258).

Example 3

Screening for Peptides Mediating siRNA Transfection

In order to analyze the potential CPPs for their ability to transfect siRNA into mammalian cells an increasing peptide concentration (from 1 µM to 20 µM) was employed along with a constant siRNA concentration (100 nM). This range of peptide concentrations was used as it had been shown that positively charged peptides such as TAT are internalized into cells in ranges up to 10 µM and remain in intracellular membrane compartments without significant egress into the cytosol (Duchardt, F. et al. (2007) *Traffic* 8, 848-866). Only above a threshold of about 5-10 µM these peptides were shown to egress into the cytosol. A concentration of 10 nM siRNA is in the saturation range as determined in control experiments using the DharmaFECT transfection reagent (Dharmacon, Inc., Lafayette, Colo., USA; data not shown.).

The siRNA oligonucleotides employed were directed against human Aha1 mRNA (Panaretou, B. et al. (2002) *Mol. Cell* 10, 1307-1318) or against luciferase mRNA as a control.

Complexes of siRNA and the respective peptides were formed in OptiMEM medium and incubated for 15 minutes at room temperature. The cells were incubated in the presence of the complexes for three hours in OptiMEM. After washing, the cells were incubated for further 21 or 45 hours in normal growth medium. Thereafter, the levels of Aha1 mRNA and a reference mRNA (i.e. GAPDH mRNA) were measured by means of a bDNA assay. These assays were performed with cells that were transfected with siAHA1 and with a control siRNA (siGL3, luciferase), respectively.

As a measure for specific RNAi, the reduction of Aha1 mRNA levels relative to GAPDH mRNA levels was compared in siAHA1-transfected cells and siGL3-transfected cells. Specific siRNA mediated transfection causes a reduction in Aha1/GAPDH mRNA values in siAhA1-compared to siGL3-transfected cells. FIG. 3 depicts the screening readout of these assays: the Aha1/GAPDH mRNA values of non-transfected control cells were set to 100% (for each assay), and the Aha1/GAPDH mRNA values of siAha1- or siGL3-transfected cells were expressed relative to that. For this normalized data set, the differences between the respective Aha1/GAPDH mRNA levels of siAha1- and siGL3-transfected cells were determined. Specific peptides caused a significant reduction in siAha1 transfection without reducing siGL3 transfections, which results in positive difference values. The more pronounced these values are, the more specific RNAi is observed (cf. FIG. 3).

In selected samples, Aha1 mRNA and/or GAPDH mRNA reductions were observed in all transfection approaches. This points towards growth inhibitory or toxic effects of the peptides applied, independent of the specificity of the siRNA. Peptides that interfere with membrane integrity (i.e. CPPs) frequently have an intrinsic ability to damage cells as highlighted by the fact that some of these peptides also act as bactericidal agents (Arrighi, R. B. et al. (2008), supra). Hence, the cytotoxic activity of the putative human CPPs was analyzed by means of CytoTox-Glo and CellTiter-Glo assay (Promega Corporation, Madison, Wis., USA). Peptide mediated growth inhibition or cytotoxicity as detected by CellTiterGlow assays correlated well with a corresponding reduction of GAPDH mRNA levels. Based on this observation, GAPDH mRNA levels were used as a general readout for toxicity: an average measurement of 100% GAPDH mRNA relative to the medium control was considered as non-toxic, values between 99% and 70% as moderate toxic, and values of less than 70% as toxic (cf. FIG. 3).

Based on the potency of peptides to mediate transfection and/or growth inhibition/toxicity different phenotype categories were defined: peptides that showed less Aha1-specific siRNA transfection efficacy than TAT were assigned to the category "non-transfecting" peptides; peptides that showed equal or higher transfection potency than TAT were termed "transfecting" peptides. Similarly, peptides resulting in GAPDH mRNA values >70% were classified as "nontoxic", whereas peptides that caused a reduction of GAPDH mRNA to lesser values were termed "toxic".

Based on these categories, all peptides were assigned to one of the following four classes:
(a) non-functional peptides (non-transfecting and non-toxic)
(b) non-transfecting toxic peptides
(c) transfecting toxic peptides
(d) transfecting non-toxic peptides 3.1 Non-Functional Peptides 41 of the 61 human-derived peptides screened fell into this category (Table 1 and FIG. 3). These peptides showed no significant toxicity towards cells, nor did they mediate siRNA transfection at the concentrations applied. Thus, 67% of the peptides that were selected as putative CPPs in the in silico approach did not show any phenotype in the transfection and viability experiments. From the group of 8 control peptides, which had previously been reported to have CPP activity, three peptides (crotamine, MTS, and perforin) fell into this category.

As an example, FIG. 4 depicts the phenotype of the peptide derived from the protein WNT16, which is involved in WNT signaling (Mazieres, J. et al. (2005) *Oncogene* 24, 5396-5400). The WNT16 peptide sequence was included as candidate for experimental evaluation as it complies with the "KHR10+ extracellular" search profile.

3.2 Non-Transfecting Toxic Peptides 11 of the 61 human-derived peptides screened showed evidence for toxicity (reduced viability and/or >70% reduction of GAPDH mRNA) but did not mediate siRNA transfection at the concentrations applied (cf. Table 1 and FIG. 3). Thus, their transfection capability was inferior as compared to the TAT peptide. None of the (positive) control peptides analyzed fell into this category, thus confirming the controls in fact have transfection capability. FIG. 5 illustrates the phenotypes of two examples of peptides belonging to this class.

One peptide is derived from the human protein BPLI3 (FIG. 5A; Bingle, C. D. and Craven, C. J. (2004) *Trends Immunol.* 25, 53-55). In CellTiter-Glo assays, a dose-dependent loss of viability was observed for cells exposed to this peptide. This was paralleled by dose-dependent reductions of GAPDH mRNA levels, which confirms the approach to use the average GAPDH mRNA values as readout for growth reduction and/or toxicity. Interestingly, CytoTox-Glo assays did not indicate significant apoptosis in cells exposed to the BPIL3 peptide (data not shown). Thus, this peptide causes growth inhibition and/or cell death by a non-apoptotic mechanism. Transfection activity (specific Aha1 mRNA reduction relative to GAPDH mRNA) could not be observed for this peptide.

Another peptide with cytotoxic properties (FIG. 5B) is derived from the human protein cathelicidine (Nijink, A. and Hancock, R. E. (2009), supra). The peptide, termed FALL, was also described to possess antimicrobial functionality. The FALL peptide exhibited significant toxicity upon exposure to cells, which is reflected by a loss of cell viability and reduction of GAPDH mRNA levels. Analysis of the potential transfection activity revealed only inconclusive evidence for a specific Aha1 mRNA reduction (relative to GAPDH mRNA) at concentrations of 10 µM or higher where toxicity is pronounced. Only some minor mRNA reductions were observed under these (toxic) conditions. However, at lower concentrations (5 µM), a clear and specific reduction of Aha1 mRNA can be observed. This indicates that FALL might be capable of transfecting siRNA, even though with an inferior transfection efficacy than TAT, i.e. below the threshold set for the class of transfecting peptides.

3.3 Transfecting Toxic Peptides

This class of peptides encompasses none of the controls but 5 of the human candidate peptides. The latter showed clear evidence for transfection activity (i.e. a specific Aha1 knockdown) but also caused cell growth inhibition and/or toxicity.

As an example, FIG. 6 shows the phenotype of cells exposed to a peptide derived from the CU025 protein. CU025 is a calcium-binding domain containing protein with unknown functionality (SwissProt accession no. Q9Y426). The siRNA transfection experiments demonstrated a significant and specific reduction of Aha1 mRNA levels as compared to GAPDH mRNA levels. However, this peptide also causes growth inhibition and/or toxicity, as determined by viability assays and a significant reduction of GAPDH mRNA. This reduced viability became already evident at peptide concentrations that are required to achieve transfection and RNAi. Thus, applicability of this peptide and of other members of this peptide class for siRNA transfection is severely restricted by their toxic phenotype.

3.4 Transfecting Non-Toxic Peptides

This class of peptides is most interesting for applications involving the transfection of siRNA as these peptides have transfecting functionality at concentrations that do not interfere with cell viability. Most control peptides fell into this class. Of the 61 human peptide candidates selected for experimental evaluation three peptides showed clear evidence for transfection activity at concentrations that mediated either no or only minimal interference with cell viability. These peptides were derived from CPXM2, a previously uncharacterized carboxypeptidase (SwissProt accession no. Q8N436), from ASM3B (SwissProt accession no. Q92485), an acid sphingomyelinase-like phosphodiesterase, and from the human GDNF related neurotrophic factor neurturin (NRTN; Kotzbauer, P. T. et al. (1996) Nature 384, 467-470).

FIG. 7 compares the transfection-mediated specific Aha1 knockdown and effects on cell viability of the CPXM2 (FIG. 7B), ASM3B (FIG. 7C), and NRTN (FIG. 7D) peptides with that of the TAT and Poly-Arg (FIG. 7A). Both CPXM2 and ASM3B resulted in a significant reduction of endogenous Aha1 mRNA levels when co-applied with a Aha1 specific siRNA without significant toxicity. This phenotype was similar to that observed for the control peptides TAT and Poly-Arg (data not shown).

The NRTN peptide mediated an even more effective reduction of Aha1 mRNA levels relative to GAPDH mRNA levels with only minor effects on cell viability. Cell growth/viability was only affected at high concentrations (above 10 µM). Interestingly, the NRTN peptide still showed marked transfection functionality at lower non-toxic concentrations. At these concentrations, the transfection efficacy of the NTRN-derived peptide was higher than that of all (positive) control peptides analyzed. In view of this phenotype, the NRTN peptide was subjected to a more detailed characterization.

Example 4

The Formation of Peptide/siRNA Complexes is Necessary but not Sufficient for Mediating Transfection Mechanisms that may explain transfection functionalities of charged peptides such as TAT or protamine include the formation of complexes between positively charged peptides and negatively charged nucleic acids. Such complexes enable peptide-mediated membrane-interacting and/or endosome escape functionalities to transfer the complexed nucleic acids into the cytosol of cells (Law, M. et al. (2008) Biotechnol. Prog. 24, 957-963) In order to address whether the above mechanism may apply to the NTRN-derived peptide as well gel-shift assays were performed (cf. FIG. 8). To this end, siRNA was co-incubated with increasing concentrations of peptide, followed by analyses of their migration pattern via gel electrophoresis. The TAT peptide exhibited the expected (positive control!) concentration-dependent retardation of siRNA migration (FIG. 8A). Thus, TAT forms complexes with the siRNA molecules. For TAT, gel-shifts were observed starting at peptide-to-siRNA ratios of 10:1, with most pronounced effects at ratios of 25:1 or higher.

A parallel analysis with siRNAs exposed to the NTRN-derived peptide is shown in FIG. 8B. A retardation of the siRNAs was already observed at peptide-to-siRNA ratios of 1:1 or higher. Furthermore, in contrast to TAT (which always migrated into the gel), NTRN-peptide/siRNA ratios of 25:1 resulted in retention of the complexes formed in the loading pocket. At higher ratios, detection via ethidium bromide staining was prevented. This finding is consistent with the observation that complexes of nucleic acids with poly cationic peptides are less accessible to intercalating agents (Wolfert, M. A. and Seymour, L. W. (1996) Gene Ther. 3, 269-273). However, upon treatment with protease K the corresponding siRNA signal could be observed in the gel (cf. FIG. 8C). Thus, the NRTN-derived peptide is able to form stable complexes with siRNA that appear to be highly condensed.

These results indicated that formation of peptide/siRNA complexes is associated with the transfection functionality of both TAT- and NTRN-derived peptides. Hence, it is reasonable to assume that said complexation (i.e. complex formation) is required in order to utilize of membrane interacting and/or "endosome escape" functionalities of peptides for siRNA transfection. However, the question to be answered is whether the observed complexation is also sufficient for transfection functionality? Accordingly, the siRNA complexation capability was also analyzed for the WNT16-derived peptide, which does neither show cytotoxicity nor transfection functionality (see above). The gel shift assay for siRNAs exposed to the WNT16-derived peptide showed a clear dose-dependent retardation of the electrophoretic siRNA mobility, even stronger than observed for the TAT peptide (cf. FIG. 8D). Peptide-to-siRNA ratios of 1:1 and higher mediated effective gel shifts. The observation that non-transfecting peptides effectively form complexes indicates that complexation of peptide and siRNA per se is not sufficient to confer transfection functionality. Thus, siRNA complexation appears to be a necessary prerequisite for functionality, but additional sequence and/or structural features of the peptides may also be important to mediate transfection The above data showed that the NTRN-derived peptide forms complexes with siRNA molecules and mediates their transfection in an effective manner. The siRNA applied was siAha1, which targets the mRNA of a cellular housekeeping gene, the activator of heat shock protein 90 ATPase homolog 1 (Panaretou, B. et al. (2002), supra). A siRNA directed against luciferase mRNA was used as a control.

In order to prove that the NTRN peptide is generally applicable for siRNA transfection (and not restricted to particular siRNA sequence), its ability to transfect a siRNA other than siAha1 was investigated. FIG. 9 shows the results of the NTRN peptide-mediated transfection of a siRNA targeting the mRNA of mitotic kinesin Eg5 (Blangy, A. et al. (1995) Cell 83, 1159-1169). An effective reduction of cellular Eg5 mRNA levels was found at concentrations of <10 µM. At these doses, the NTRN peptide does not interfere with cell viability. It is known that effective depletion of Eg5 mRNA causes mitotic arrest resulting in the onset of apoptosis (Blangy, A. et al. (1995), supra). Accordingly, an apoptotic phenotype was observed upon NTRN-peptide mediated siEg5 transfection (FIG. 9). Transfections with control siRNA under identical conditions were not cytotoxic either, thus confirming that the apoptotic phenotype was caused by Eg5 mRNA depletion.

The above data demonstrate that the human NRTN-derived peptide is not only generally applicable for mediating transfection of siRNAs but also that its transfection efficacy is sufficient to elicit RNAi mediated cellular phenotypes.

Example 5

Transfection Competent Peptides are Internalized into Cells

For determining the internalization behavior of the CPPs identified in the screening procedures FITC-labeled derivates of said peptides (at 1 µM, 5 µM, and 10 µM, respectively) were analyzed by means of FACS. The following peptides were used: NRTN as a transfecting peptide, WNT16 as a non-transfecting peptide, FALL as a toxic peptide and TAT as a reference (positive control) (cf. FIG. 12). MCF7 cells were incubated in the presence of the fluorescent peptide derivatives for 3 hours at 37° C. in OptiMEM. Subsequently, the cells were treated with proteinase K for 30 minutes at 37° C. to remove surface bound peptides, and thus to ensure the monitoring only of internalized peptides. The cells were then washed in PBS and analyzed by FACS.

The results show that the control peptide TAT is internalized into the MCF cells (cf. FIG. 12A). The uptake of TAT into the cells shows linear dependency on the concentration of the peptide, which is also in line with the finding that TAT functions as a siRNA transfection reagent (cf. above). The non-transfective non-toxic peptide WNT16 did not show significant uptake into MCF7 cells (FIG. 12B), which is consistent with the peptide's observed inability to transfect siRNA. This also demonstrates that uptake of a peptide does not simply correlate with the presence of positively charged amino acids. The toxic FALL peptide was internalized into MCF cells in a linear concentration-dependent manner (FIG. 12C).

The transfection-positive peptide NRTN was also internalized into MCF7 cells (FIG. 12D). In contrast to the other peptides, however, NRTN did not display a linear concentration-dependent uptake. In fact, a strong increase in internalization was observed when increasing the concentration from 5 µM to 10 µM. This finding suggests that there is a threshold value below of which the uptake is significant but weak. Above the threshold value, a marked increase in cellular uptake is observed.

Taken together, these results show the ability of transfection positive peptides to interact with and to become internalized into cells. In addition, these data show that the peptides analyzed do not only function as transfection reagents, but also act as cell penetrating peptides.

Example 6

Sorting, Filtering, and Classification of Peptide Candidates

By combining in silico and experimental screening procedures peptide sequences having potential CPP or transfection functionalities were found in the human proteome. Among these candidates, three peptides were found to be transfection-competent but non-toxic, that is, they possess transfection functionality at doses that do not interfere with cell viability. These peptides might inter alia serve as modules in the development of a siRNA delivery agent as part of future siRNA based drugs.

6.1 Bioinformatics Approach

The in silico procedures employed were based on a 30mer peptide library that contained all overlapping peptides present in human proteins. From these more than $10 \times 10^6$ peptides, 8630 peptides derived from 583 human extracellular proteins were identified that met the initial search string (>30% positively charged amino acid residues (i.e. H+K+R) in a 30mer peptide).

To generate a short-list of peptides that were subjected to wet-lab experimentation, the number of candidates were further limited by the negative and positive selection steps: in cases, where due to long basic stretches multiple peptide hits occurred in a single protein, redundancy was avoided. In most of these cases, one representative peptide derived from a given protein was selected. Peptides that deemed to be difficult to synthesize or to handle, e.g., due to the presence of multiple disulfide bridges or a predicted poor solubility, were excluded from further consideration. Several positive selection parameters for choosing (from the remaining list) candidates for experimental evaluation were applied, including (i) high IEP and a high degree of hydrophobicity; (ii) sequence similarity with TAT; and (iii) proposed membrane interacting functionality of the proteins from which the peptides were derived, such as proteins of complement system, bactericidal factors, and lipases.

6.2 Experimental Approach

Upon experimental evaluation the candidate peptides (defined by in-silico procedures) were grouped into four classes: (a) non-functional peptides (i.e. non-transfecting and non-toxic), (b) non-transfecting toxic peptides, (c) transfecting toxic peptides, and (d) transfecting non-toxic peptides.

In a first approach, peptide candidates were selected based on their top-ranking IEP values and hydrophobicity profiles, such as the transfection-competent toxic peptides CU025 and CPXM, the non-transfecting toxic peptides CD026 and MMP25. Hence, this filter is capable of identifying putative cell-penetrating peptides (CPPs) from a positive amino acid enriched peptide source.

Another filter applied was based on the candidate peptide's sequence similarity with the TAT reference peptide. Five peptides having the most pronounced similarity with TAT were experimentally evaluated. However, four of these peptides (including PROK2 displaying the highest similarity with TAT) did not show detectable transfection activity at doses that do not interfere with cell viability. The NRTN-derived peptide was the only functional (i.e. transfection-competent) member. This peptide showed the best transfection functionality in the assays performed, having an efficacy even higher than TAT. This indicates that for the transfection activity of these peptides is not only determined by the primary amino acid sequences but also by defined sequence motifs, and particularly by secondary structures.

In a third approach, both literature data and BLAST results were used for limiting the list of candidate peptides. Selected for experimental evaluation were peptides derived from proteins that require for their activity an interaction with membranes. Most of the peptides selected did not show any functional phenotype (i.e. transfection capability). Even peptides derived from proteins that are well known to disturb membrane integrity (such as complement factors or perforin) did not show transfection functionality. This finding suggests that properly structured domains may be necessary to confer the membrane-disrupting activities of these proteins (e.g., the MACPF domain (Rosado, C. J. et al. (2008) *Cell. Microbiol.* 10, 1765-1774)). Apparently, this functionality cannot be mimicked by peptides, even though they matched the search strategy employed.

On the other hand, the transfecting non-toxic peptides derived from CPXM2 and ASM3B, respectively, and the toxic peptides derived from BPIL3 and FALL39 are included in this third group. Interestingly, some of the peptides classified as toxic were derived from bactericidal peptides. Such peptides interfere with the membrane integrity of pathogens. In high concentrations, these peptides are toxic to human cancer cells. At least the FALL peptide was shown—in a particular concentration range—to mediate siRNA transfection. This finding could either be explained by the formation of holes in the plasma membrane through which non-specific uptake of the siRNA may occur. Another explanation would be a peptide-mediated siRNA uptake that is masked by the toxicity of the peptide. Furthermore, the recently proposed membrane repair mechanism involved in CPP uptake (Palm-Apergi, C. et al. (2009) *FASEB J.* 23, 214-223) might also contribute to explain the partial functionality of these peptides.

However, the fact that these peptides reduce cell viability already at concentrations that are necessary for transfection hampers the applicability of this class of peptides for siRNA delivery.

Example 7

Characterization of the NRTN-Derived Peptide 7.1 Structural Features of the NRTN-Derived Peptide The neurturin (NRTN)-derived peptide was the candidate identified in the present screening that consistently showed the highest ability to transfect siRNAs at concentrations that do not interfere with cell viability. This peptide is capable of forming non-covalent complexes with siRNA that involved a strong condensation of the nucleic acid. This feature is in line with the finding that NRTN-complexed siRNA is not accessible to ethidium bromide intercalation. As determined by means of gel-shift assays, complex formation between NRTN and siRNA was maximal at a ratio of 1:50. This corresponds to a ratio of 100 nM siRNA to 5 µM peptide in the in vitro test system for functionality (i.e. transfection capability) used herein. However, if the concentration of NRTN is increased in the in vitro system to ratios above complex saturation, an additional transfection activity is observed. This finding might be explained by the ability of free positive charged NRTN peptide to protect siRNA-NRTN complexes from disruption by anionic proteoglycans on the cellular surface.

What could be the mechanism by which the NRTN peptide mediates siRNA transfection? The formation of complexes with nucleic acids is certainly one necessary requirement for peptide functionality because all transfection-competent peptides displayed this feature. However, complexation per se is not sufficient to mediate transfection as there were also identified peptides that form siRNA complexes equally well or even better than TAT but do not possess transfection functionality. Furthermore, the composition of the primary sequence, i.e. the number of charged and/or hydrophobic residues present, is also unlikely to solely mediate functionality. Many peptides having sequence similarity with TAT (including peptides with a very high degree of sequence similarity) turned out to be non-functional.

One possible explanation for transfection functionality of the NRTN-derived peptide may be seen in its secondary structure. Choosing 30-mer peptides for performing the screen (in contrast to most other approaches that apply shorter peptides (Futaki, S. et al. (2001), supra; Crombez, L. et al. (2007) *Biochem. Soc. Trans.* 35, 44-46; Jafari, M and Chen, P. (2009) *Curr. Top. Med. Chem.* 9, 1088-1097)) has the advantage that these peptides have a higher probability to fold in and to maintain a particular secondary structure. NRTN is a member of the TGF growth factor protein family and similar to GDNF and Artemin whose respective structures have already been resolved (Eigenbrot, C. and Gerber, N. (1997) *Nat. Struct. Biol.* 4, 435-438; Wang, X. et al. (2006) *Structure* 14, 1083-1092).

A sequence alignment of the rat GDNF sequence and the human NRTN sequence and a comparison of proposed secondary structures reveal that the transfection active NRTN peptide stretch may form a secondary structure (cf. FIG. 10). The sequence corresponding to the functional NRTN-peptide is partially located on the accessible surface of the protein and contains a positively charged alpha-helical stretch of amino acids. The identification of alpha-helical structures within NRTN is fully in line with existing hypotheses that alpha-helical structures are advantageous with regard to membrane penetration (Deshayes, S. et al. (2004), supra). The observation that the NRTN-derived peptide analyzed encompasses the complete alpha-helical structure as well as surrounding regions supports the validity of the present approach to screen larger peptides. It remains to be clarified if the alpha-helical structure per se (which covers 12 amino acids of the 30mer peptide) is sufficient to mediate efficient transfection. However, it appears likely that at least some of the additional residues are also required for peptide functionality.

In order to obtain experimental evidence for these secondary structure predictions the NRTN peptide was further analyzed for the presence of secondary structural elements by means of UV circular dichroism (UV-CD) spectroscopy (reviewed, e.g., in Whitmore, L. and Wallace, B. A. (2008) *Biopolymers* 89, 392-400). This technique enables the identification of sequence elements folding into secondary structures based on their particular UV spectra as compared to non structured random coil stretches. The analysis was performed using a Jasco J 715 Spectropolarimeter (Jasco, Inc., Easton, Md., USA) from 195 nm to 260 nm with a data pitch of 0.1 nm and a bandwidth of 1 nm. The cell of the apparatus had a length of 0.1 cm. The peptides were employed at a concentration of 0.1 mg/ml (cf. FIG. 11).

The FALL peptide which was previously shown to fold in an alpha-helical structure was used as a positive control (Agerberth, B. et al. (1995) Proc. Natl. Acad. Sci. USA 92, 195-199). In aqueous solution, the FALL peptide adopted a random coil conformation. In the presence of 10% trifluoroethanol (TFE) as a co-solvent characteristic the spectra showed characteristic minimum peaks at 208 nm and 222 nm, respectively, which became more pronounced with an increase in TFE concentration (i.e. 25% TFE and 50% TFE; cf. FIG. 11A). TFE is known to stabilize and induce the formation of secondary structures in peptides and proteins (Buck, M. (1998) Q. Rev. Blophys. 31, 297-355).

When analyzing the NRTN peptide under the same assay conditions as the FALL peptide, an analogous spectrum was observed, that is, a spectrum exhibiting minimum peaks at 208 nm and 222 nm, respectively. Hence, the NRTN peptide in fact comprises an alpha-helical portion as predicted based on sequence homology data (cf. FIG. 11B).

In contrast, the spectrum obtained with the TAT peptide did not show indications that this peptide folds into a secondary structure. Even in the presence of 50% TFE the peptide adopted a random coil conformation (cf. FIG. 11C).

Furthermore, the internalization behavior monitored via FACS analysis demonstrated that the NRTN peptide does not only function as a transfection reagent, e.g., for siRNA molecules, but also as a cell penetrating peptide, even in the absence of nucleic acid molecules. This finding suggests that NRTN may also represent a suitable carrier for a conjugated cargo, such as other peptides or proteins. Notably, the internalization of NRTN does not seem to linearly depend on the concentration employed. Rather, there appears to be a specific threshold value above of which cellular uptake occurs. Such threshold phenomena were also observed for the internalization behavior of other peptides such as TAT and Poly-Arg (Duchardt, F. et al. (2007), supra).

Moreover, the FACS analysis revealed a strong accumulation of the FALL peptide in the cells. This finding is consistent with the observation that FALL acts as a cytotoxic peptide. Toxicity requires direct physical interaction of the peptide and the target cell. In contrast to the NRTN peptide, however, the internalization behavior of FALL was linearly dependent on its concentration. Hence, there is no threshold for the toxicity of FALL, which is consistent with the cell viability data obtained, demonstrating a concentration-dependent cytotoxicity.

On the other hand, the non-transfective peptide WNT16 was not internalized to a significant extent into the cells. Thus, the sole presence of positive charged amino acids in the primary sequence of peptides is not indicative for the peptide's usability as CPP. These results provide further hints that sequence motifs folding into a secondary structure (as in NRTN) may constitute major determinants for the cellular uptake of CPPs.

7.2 the NRTN-Derived Peptide has Transfection Activity in the Presence of Serum

Therapeutic siRNA delivery is one intriguing application for the human CPP-like peptides identified. The replacement of non-human pathogen derived entities with human sequences exhibiting a similar or even better functionality is advantageous for therapeutic approaches because it reduces the risk that transfection modules may be immunogenic. Therapeutic application of a given peptide also requires that said peptide has a sufficient (transfection) activity. Furthermore, the peptide's observed in vitro activities must also be true in the in vivo setting.

Most of the assays described herein were performed under the "standard in vitro conditions" for the detection of peptide-mediated transfection that are well established in the art (see, e.g., Simeoni, F. et al. (2003) Nucleic Acids Res. 31, 2717-2724; Richard, J. P. et al. (2005) J. Biol. Chem. 280, 15300-15306; Abes, R. et al. (2007) Biochem. Soc. Trans. 35, 775-779; Kumar, P. et al. (2007) Nature 448, 39-43; Mueller, J. et al. (2008) Bioconjug. Chem. 19, 2363-2374; Sugita, T. et al. (2008) Br. J. Pharmacol. 153, 1143-1152). Accordingly, the incubation for the initial "transfection step" is performed under basically serum free conditions. The addition of serum at this step interferes with the transfection ability of the CPPs (cf. FIG. 13; see also Ignatovich, I. A. et al. (2003), supra). However, therapeutic applicability of (CPP-like) peptides will obviously require serum contact. It is noteworthy that in the presence of medium (albeit with a reduced serum concentration) the NRTN peptide can still mediate transfection (cf. FIG. 13).

7.3 the NRTN-Derived Peptide Binds to and Internalizes into Epithelial Cells in a Blood-Brain-Barrier Cell Culture Model It has previously been reported that cell penetrating peptides are not only applicable as transfection vehicles for siRNA delivery into cells, but also appear to be functional in the penetration of barriers such as the blood-brain-barrier, e.g., in order to mediate RNAi in the brain (Mathupala, S. P. (2009) Expert Opin. Ther. Pat. 19, 137-140). It is tempting to speculate that NRTN may be functional in this regard as well, since NRTN is a glia cell-derived neurotrophic factor (Sariola, H. and Saarma, M. (2003) J. Cell Sci. 116, 3855-3862) potentially having good access to the central nervous system.

In order to evaluate potential interactions of the NRTN-derived peptide with endothelial cells forming the blood-brain-barrier, hCMEC/D3 cells or primary human brain endothelial cells were exposed to the NRTN-derived peptide in a blood-brain-barrier (BBB) model (Weksler, B. B. et al. (2005) FASEB J. 19, 1872-1874; Poller, B. et al. (2008) J. Neurochem. 107, 1358-1363). The results of these analyses (cf. FIG. 14) reveal that the NRTN-derived peptide accumulates (i.e. internalizes) under these assay conditions in endosomal structures. In BBB endothelial cells, cellular passage of hydrophilic molecules is efficiently prevented by tight junctions, and endosomes are a major component of the transcytosis mechanisms that enable controlled transport of macromolecules across the blood-brain-barrier. Thus, the NRTN-derived peptide localizes to a compartment that is important for BBB functionality (that is, for mediating and controlling transport across the BBB).

A further possible extension of the therapeutic applicability of CPPs would be their combination with targeting moieties such antibodies and antibody fragments.

Example 8

Application of the NRTN-Derived Peptide for the Intracellular Delivery of Pro-Apoptotic Peptides The internalization behavior of the NRTN-derived peptides (cf. above) indicated that these peptides do not only function as a transfection reagents, e.g., for siRNA molecules, but also as 'classical' cell penetrating peptides. This finding suggests that NRTN may also represent a suitable carrier for a conjugated cargo, such as other peptides or proteins.

In order to determine whether NRTN-derived sequences are capable to mediate cellular uptake of peptides, various biologically active peptides were fused to NRTN. The peptide fusion partners employed were shown to interact with cytoplasmic target proteins involved in mediating apoptosis. In other words, if expressed or actively delivered to the cytoplasm of cancer cells, these peptides induce apoptosis (i.e. they are "pro-apoptotic"). However, these pro-apoptotic peptides cannot penetrate biological membranes per se. Only their conjugation or fusion to known CPPs, such as TAT, penetratin, and poly-Arg, enables cellular uptake and thus induction of apoptosis.

For evaluating the cell penetrating functionality of the NRTN-derived sequences the following fusion partner were used: (i) a nuclear receptor Nur77-derived peptide which interacts with BCL2 and converts it into a pro-apoptotic molecule; and (ii) a 4E-BP1-derived peptide interacting with the translation factor eIF4E that binds the 5' CAP structure of mRNAs and is known to modulate apoptosis in cancer cells.

8.1 NRTN-Mediated Intracellular Uptake of a Pro-Apoptotic NUR77-Derived Peptide

Nur77 is a nuclear orphan receptor capable of interacting with key mediators of apoptosis, such as BCLB and BCL2. The interaction of Nur77 with BCL2 causes conformational changes of BCL2 resulting in the exposure of its BH3 domain. This converts BCL-2 into a protein with pro-apoptotic function (Lin, B. et al. (2004) *Cell* 116, 527-540; Luciano, F. et al. (2007) *Blood* 109, 3849-3855). The same conversion can also be achieved with peptides derived from related proteins such as Nor1 (Kolluri, S. K. et al. (2008) *Cancer Cell* 14, 285-298).

The respective BCL2-interacting sequences of Nor1 and Nur77 can be aligned as follows:

```
Nor1
                               (SEQ ID NO: 70)
GDWIDSILAFSRSLHSLLVDL

Nur77
                               (SEQ ID NO: 71)
GEWLDSIKDFSLNLQSLNLDI
```

An even smaller peptide capable of interacting with BCL-2 consists of the C-terminal 12 amino acids of Nor1: FSRSLHSLLVDL (SEQ ID NO: 72).

Despite its proven ability to convert BCL-2 into a pro-apoptotic molecule, addition of the latter peptide (i.e. "Nor/Nur"; SEQ ID NO: 72) to cancer cells, even in high concentrations, is not sufficient to induce apoptosis, as the cellular target protein is located in the cytoplasm, but the peptide per se cannot effectively penetrate through the cell membrane to reach the target. In brief, MCF-7 breast cancer cells were incubated in the presence of this peptide for 24 h. No reduction in cell viability or induction of apoptosis was observed (see Example 1 for cytotoxicity and viability assays). In analogy, exposure of these cells to the human-derived CPP NRTN did not affect cell viability or lead to induction of apoptosis either (cf. FIG. 15).

In order to analyze whether NRTN in fact has CPP functionality, a hybrid sequence was generated that encompasses a Nur77-derived peptide stretch at the N-terminus fused to a portion of the NRTN-peptide at the C-terminus. For defining a suitable fusion position, it was found that the C-terminal part of the Nur77-peptide was similar to a sequence stretch within the NRTN peptide and chose this region as fusion point. The amino acid sequences of the resulting NurNRTN fusion peptide as well as the two parent peptides are schematically shown in the bottom panel of FIG. 15. The fusion peptide retains the full length sequence stretch of Nur77 (in almost unmodified form) and a shortened N-terminal stretch of the NRTN peptide. The resulting peptide has the same length (30 amino acids) as the parent NRTN peptide.

The amino acid sequence of NurNRTN reads:

```
                               (SEQ ID NO: 73)
FSRSLHSLLYDLGLRRLRQRRRLRRERVRA.
```

In order to determine whether the BCL2 binding properties of the Nur77-derived peptide are maintained in the NurNRTN fusion peptide, the respective NurNRTN and NRTN peptides were coupled to iodoacetyl beads (Pierce Biotechnology, Inc., Rockford, Ill., USA). The beads were incubated with recombinant BCL2 (Calbiochem/Merck, Darmstadt, Germany) and washed with PBS and 0.5 M NaCl, 0.025 $NaN_3$, 0.05% Tween20 to remove unbound protein. Specific binding of BCL2 to the immobilized NurNTRN fusion peptide was determined by eluting bound peptide from the beads with elution buffer (pH 2.8), transfer of the eluted fraction to nitrocellulose (Invitrogen Corporation, Carlsbad, Calif., USA), and protein detection by means of the MemCode Reversible Protein Stain Kit (Pierce Biotechnology, Inc., Rockford, Ill., USA). The results of these analyses revealed that BCL2 can be detected in eluates from beads that were coated with the NurNRTN fusion peptide. In contrast, very small amounts of BCL2 were eluted from beads coated with the NRTN peptide. Hence, the NurNRTN fusion peptide retains the capability to bind BCL2.

Subsequently, it was evaluated whether the NurNRTN fusion peptide is capable of penetrating cellular membranes and thereby induces pro-apoptotic activity within cells. MCF-7 human breast cancer cells were used as a model. The experimental approach was as described above (cf. Example 1). At peptide concentrations that resulted in no cell toxicity when testing the Nur77 and NRTN peptides, respectively, the fusion peptide exhibited remarked cytotoxicity, which is also reflected by induction of apoptosis (cf. FIG. 15). This effect was dose dependent: cytotoxicity increased with increasing concentrations of peptide.

As a control, an inactive mutant of the NUR peptide was fused to the NRTN peptide. This peptide did not interfere with cell viability. Furthermore, a fusion of the NUR peptide with the inactive WNT16 peptide also did not interfere with cellular viability.

These results demonstrate that fusions of NRTN-derived sequences with peptides that are not cell-permeable per se can enter cells and elicit intracellular activity. In other words, the NRTN portion of the fusion peptide functions as vehicle in order to exert the pro-apoptotic activity of Nur77 (i.e. the cargo) in the cell. Furthermore, these results provide evidence that an NRTN-derived sequence that is altered at its amino terminus retains CPP functionality.

8.2 NRTN-Mediated Intracellular Uptake of a Pro-Apoptotic 4E-BP1-Derived Peptide eIF4E is a translation factor which binds the 5' CAP structure of mRNAs and is important for cell viability. Interference with the functionality of eIF4E can lead to apoptosis in cancer cells. The protein 4E-BP1 binds to and thereby modulated/interferes with the functionality of eIF4E. In consequence, increased levels of 4E-BP1 result in inhibition of translation and thus induction of apoptosis in cancer cells due to its modulation of eIF4E functionality (Flynn, A. and Proud, C. G. (1996) *Cancer Surv.* 27, 293-310; Robert, F. and Pelletier, J. (2009) *Expert Opin. Ther. Targets* 13, 1279-1293).

The pro-apoptotic functionality of full-length 4E-BP1 can also be achieved with a small peptide of 20 amino acids in length (Tomoo, K. et al. (2006) *Biochem. J.* 140, 237-246). This peptide comprises a eI4FE binding motif (YXRXXLB, where X is any amino acid and B is a hydrophobic residue; Moerke, N. J. et al. (2007) *Cell* 128, 257-267). Further analyses have shown that three remaining amino acid residues of the binding motif (i.e. Y, R, L) are important for pro-apoptotic functionality (Marcotrigiano, J. et al. (1999) *Mol. Cell.* 3, 707-716) Mutation of these residues (e.g., substitution by glycine residues) result in the conversion of active 4EBP1-derived peptides into inactive derivatives.

The amino acid sequences of the active and inactive 4E-BP1 peptides used herein read (for all sequences see also FIG. 16, bottom panel):

```
4E-BP1
                                        (SEQ ID NO: 74)
GTRIIYDRKFLMECRNSPVT inact4E-BP1
                                        (SEQ ID NO: 75)
GTRIIGDGKFGMECRNSPVT
```

Despite its proven capability to block eIF4E, simple addition of 4E-BP1-derived peptides to cancer cells, even in high concentrations, is not sufficient to induce apoptosis, as the cellular target protein is located in the cytoplasm, but the peptide per se cannot effectively penetrate through the cell membrane to reach the target. In brief, MCF-7 breast cancer cells were incubated in the presence of this peptide for 24 h. No reduction in cell viability or induction of apoptosis was observed (see Example 1 for cytotoxicity and viability assays). In analogy, exposure of these cells to the human-derived CPP NRTN did not affect cell viability or lead to induction of apoptosis either (cf. FIG. 16, top panel).

Previously, it was shown that the fusion of known CPPs such as TAT to 4EBP1-derived peptides result in cellular uptake of the fusion peptide (Ko, S. Y. et al. (2009) *Clin. Cancer Res.* 15, 4336-4347). The following TAT/eIFE4 fusion peptides were employed herein:

```
TAT4E-BP1
                                        (SEQ ID NO: 76)
YGRKKRRQRRRGTRIIYDRKFLMECRNSPVT

TATinact4E-BP1
                                        (SEQ ID NO: 77)
YGRKKRRQRRRGTRIIGDGKFGMECRNSPVT
```

MCF-7 breast cancer cells incubated for 24 h in the presence of these TAT/4E-BP1 fusion peptides showed clear evidence for reduction in cell viability and cytotoxicity due to induction of apoptosis (see Example 1 for cytotoxicity and viability assays) at concentrations of 20 µM. This effect is specifically mediated by the functionally active (i.e. pro-apoptotic) 4E-BP1 peptide sequence as the corresponding mutated variant was completely inactive. (cf. FIG. 16, medium panel).

In order to analyze whether NRTN in fact has CPP functionality, a hybrid sequence was generated that encompasses a portion of the NRTN-peptide at the N-terminus fused to the active or inactive 4EBP1-derived peptide stretch at the C-terminus. The amino acid sequences of the resulting two fusion peptides are schematically shown in the bottom panel of FIG. 16. The fusion peptides retain the full length sequence stretch of 4E-BP1 as well as the full-length NRTN peptide resulting in a total length of 50 amino acids. Thus, these molecules are significantly larger than known CPPs.

The amino acid sequences of the active or inactive NRTN/4E-BP1 fusion peptides read:

```
NRTN4E-BP1
                                        (SEQ ID NO: 78)
GAAEAAARVYDLGLRRLRQRRRLRRERVRAGTRIIYDRKFLMECRNSPVT

NRTNinact4E-BP1
                                        (SEQ ID NO: 79)
GAAEAAARVYDLGLRRLRQRRRLRRERVRAGTRIIGDGKFGMECRNSPVT
```

Subsequently, it was evaluated whether the NRTN4E-BP1 fusion peptide is capable of penetrating cellular membranes and thereby induces pro-apoptotic activity within cells. MCF-7 human breast cancer cells were used as a model. The experimental approach was as described above (cf. Example 1). At peptide concentrations that resulted in no cell toxicity when testing the 4E-BP1 and NRTN peptides, respectively, the fusion peptide exhibited remarked cytotoxicity, which is also reflected by induction of apoptosis (cf. FIG. 16, medium panel). This effect was dose dependent: cytotoxicity increased with increasing concentrations of peptide.

Furthermore, the NRTN-fusion peptide displayed a significantly higher potency as compared to its TAT-fused counterpart. In addition, the cytotoxic effect observed is specifically mediated by the functionally active (i.e. pro-apoptotic) 4E-BP1 peptide sequence portion as the corresponding mutated variant of the fusion peptide was inactive. (cf. FIG. 16, medium panel). A fusion of the 4E-BP1 peptide with the WNT16 peptide did not interfere with cellular viability.

These results demonstrate that fusions of NRTN-derived sequences with peptides that are not cell-permeable per se can enter cells and elicit intracellular activity. Direct comparison with TAT-fused peptides revealed NRTN-fusions to have higher potency. These results also provide evidence that an NRTN-derived sequence that is altered at its carboxy terminus retains CPP functionality. Finally, by utilizing NRTN-derived sequences functional CPPs can be generated that have a length of at least 50 amino acids.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

TABLE 1

Human candidate CPPs as well as control peptides subjected to experimental evaluation.

| SEQ ID NO: | PEPTIDE NAME | AMINO ACID SEQUENCE | CLASS |
|---|---|---|---|
| 1 | TAT | GRKKRRQRRRPPQ | + |
| 2 | NRTN | GAAEAAARVYDLGLRRLRQRRRLRRERVRA | + |
| 3 | CPXM2 | IREIMEKFGKQPVSLPARRLKLRGRKRRQR | + |
| 4 | ASM3B | YLKVVRKHHRVIAGQFFGHHHTDSFRMLYD | + |
| 5 | FGF12 | SKVRFCSGRKRPVRRRPEPQLKGIVTRLFS | +/tox |
| 6 | CU025 | SMSVLEPGTAKKHKGGILRKGAKLFFRRRH | +/tox |
| 7 | IGS10 | QRKIGGRGRIISPYRTPVLRRHRYSIFRST | +/tox |
| 8 | CPXM | QHVRIRVIKKKKVIMKKRKKLTLTRPTPLV | +/tox |
| 9 | CD026 | FHFFPRRPRIHFRFPNRPFVPSRCNHRFPF | +/tox |
| 10 | FALL39 Var.1 | FALLGDFFRKSKEKIGKEFKRIVQRIKDFLRNLV PRTES | +/tox |
| 11 | Poly-Arg | RRRRRRRRR | + |
| 12 | INF7 | GLFEAIEGFIENGWEGMIDGWYG | + |
| 13 | REV | TRQARRNRRRRWRERQR | + |
| 14 | Trunc_protamine | RSQSRSRYYRQRQRSRRRRRS | + |
| 15 | Crotamine | YKQCHKKGGKKGSG | - |
| 16 | MTS | KGEGAAVLLPVLLAAPG | - |
| 17 | Perforin_NT | PAHTAARSEAKRSHKPVPGAWLAGEGVDVTSL RR | - |
| 18 | BPIL3 (38 aa) | VAVAYPKSKPLTTQIKIKKPPKVTMKTGKSLLHL HSTL | tox |
| 19 | BPIL3 (30 aa) | KSKPLTTQIKIKKPPKVTMKTGKSLLHLHS | tox |
| 20 | Defensin-Cons ($C^{I,III,V,VI}$-S) | GLRRSRVRGGRCRKSSKEIERKKGKCSTRGRK SSRRKK | tox |
| 21 | LIP_Con_N | IKKMRRKRSSKMYLKTRAQMPFKVYHYQLKIHF IGYKN | tox |
| 22 | ApoL_cons_1 | REFPRLKRKLKGHIRKLRALADDVDKVHKKF | tox |
| 23 | ApoL_cons_2 | LRNTLKYAKKVVRAFWRARANPRLLNATKR | tox |
| 24 | FAM5C | FLKAQKIVHKLFSLSKRAHKQPLISLPRQR | tox |
| 25 | FAM5B | QHRYQQLGAGLKVLFKKTHRILRRLFNLAK | tox |
| 26 | COOA1 | MHLRAHRTRRGKVSPTAKTKSLLHFIVLAV | tox |
| 27 | MMP25 | GLVRRRRRYALSGSVWKKRTLTWRVRSFPQ | tox |
| 28 | NETR | RLLHRRQKRIIGGKNSLRGGWPWQVSLRLK | tox |
| 29 | SCUB3 | LRQRMERRLKGSLKMLRKSINQDRFLLRLA | tox |
| 30 | Defensin-Cons | GLRRCRVRGGRSRKSSKEIERKKGKSSTRGRK | - |

TABLE 1-continued

Human candidate CPPs as well as control peptides subjected to experimental evaluation.

| | | | |
|---|---|---|---|
| | ($C^{II,III,IV,VI}$-S) | CSRRKK | |
| 31 | Granulysin_WT | KLKKMVDKPTQRSVSNAATRVARTGRSRWR | - |
| 32 | Granulysin_G9 | QRSVSNAATRVSRTGRSRWRDVSRNFMRR | - |
| 33 | CO6_mot2 | AKHCVRIETKKRVLFAKKTKVEHRCTTNKL | - |
| 34 | CO6_mot1 | ASHKKDSSFIRIHKVMKVLNFTTKAKDLHL | - |
| 35 | CO8_mot1 | LGISSQSDRGKHYIRRTKRFSHTKSVFLHA | - |
| 36 | CO9_mot1a | EHYEEQIEAFKSIIQEKTSNFNAAISLKFT | - |
| 37 | CO9_mot1b | LHGKGSFRFSYSKNETYQLFLSYSSKKEKM | - |
| 38 | Perforin_SC | KKKKHKMTASFHQTYRERHSEVVGGHHTSIN | - |
| 39 | Factor_H_derived | AIDKLKKAKSSNLIILEEHKLKNKKEFDHNS | - |
| 40 | LIP_Cons_C_WT | IKKIRVKAGETQKKLTFCSEDKDSHLIKPKREKIF VKCRDKSKMKKRK | - |
| 41 | LIP_Cons_C_AA | IKKIRVKAGETQKKLTFASEDKDSHLIKPKREKIF VKARDKSKMKKRK | - |
| 42 | ApoL_cons_3 | RSKSAEELRAKAQELERKLDRLTQHHRHLQ | - |
| 43 | CRSPL | VPRYRRKRHISVRDMNALLDYHNHIRASVY | - |
| 44 | ATS7 | RRERWEQRQQWRRPRLRRLHQRSVSKEKWV | - |
| 45 | AREG | KTESENTSDKPKRKKKGGKNGKNRRNRKKK | - |
| 46 | FA20A | QEALRYYRRKVARWNRRHKMYREQMNLTSL | - |
| 47 | GNAS3 | KEEKQRRRAKPKKPTRRDASPESPSKKGPI | - |
| 48 | PAP2 | RRGWAKSRQRRQVWKRRAEDGQGDSGISSH | - |
| 49 | HISTATIN_1 | ISADSHEKRHHGYRRKFHEKHHSHREFPFY | - |
| 50 | HISTATIN_3 | ADSHAKRHHGYKRKFHEKHHSHRGYRSNYL | - |
| 51 | NPTX3 | LKAWVRKLQRRGRKVDTRLRALDLTLGERS | - |
| 52 | PROL4 | GHHRHPPPPPFQNQQRPPRRGHRQLSLPRF | - |
| 53 | YC002 | GSRPRHLLSERSRRSGRGWPRPRAAYRALL | - |
| 54 | CD029 | KYRPVAIHLAGTGDHHYWRRRTLMARPMIK | - |
| 55 | TOR2 | SPRVHHFSPVLHFPHPSHIERYKKDLKSWV | - |
| 56 | CO4AB | GRRNRRRREAPKVVEEQESRVHYTVAIWRN | - |
| 57 | SULF1 | FKEAAQEVDSKLQLFKENNRRRKKERKEKR | - |
| 58 | PROK2 | LTRKNNFGNGRQERRKRKRSKRKKEVPFFG | - |
| 59 | WNT16 | IQISDKTKRKMRRREKDQRKIPIHKDDLLY | - |
| 60 | GRAK | LVKLQTAAKLNKHVKMLHIRSKTSLRSGTK | - |
| 61 | APLD1 | DALRRFQGLLLDRRGRLHGQVLRLREVARR | - |
| 62 | CBPN | VNFHLKRSIPQVSPVRRAPSRRHGVRAKVQ | - |
| 63 | CFAI | AERRRIKSLLPKLSCGVKNRMHIRRKRIVG | - |
| 64 | FGF5 | VALNKRGKAKRGCSPRVKPQHISTHFLPRF | - |
| 65 | LTB1L | TVSGVHRRRPIHHHVGKGPVFVKPKNTQPV | - |
| 66 | LFTY1 | VPKAALHRHGRLSPRSARARVTVEWLRVRD | - |
| 67 | LOXL3 | GHRRLLRFSSQIHNLGRADFRPKAGRHSWV | - |
| 68 | PONL | RLASARVHHRAFRRLRALRSLDLAGNQLTR | - |
| 69 | PRS23 | LKKPHKRKFMKIGVSPPAKQLPGGRIHFSG | - |

Control peptides are shown in grey.

The column "Class" denotes the functional classification of the peptides with regard to their transfection capabilities as well as cytotoxicity: "−", non-transfecting non-toxic peptides; "tox", non-transfecting toxic peptides; "+/tox", transfecting toxic peptides; "+", transfecting non-toxic peptides.

The invention claimed is:

1. A peptide capable of being internalized into a cell, wherein the peptide:
   (a) has an amino acid sequence selected from the group consisting of: GAAEAAARVYDLGLRRLRQRRRL-RRERVRA (SEQ ID NO: 2); and
   an amino acid sequence having over its total length at least 80% overall sequence identity with SEQ ID NO: 2; and
   (b) is internalized into a cell with an efficacy being at least 200% of the internalization efficacy of the TAT peptide having the amino acid sequence GRKKRRQRRRPPQ (SEQ ID NO: 1).

2. The peptide of claim 1, wherein at least a part of the peptide forms an alpha-helical secondary structure.

3. The peptide of claim 1, wherein the peptide is of mammalian origin.

4. A nucleic acid molecule encoding the peptide of any one of claims 1 to 3.

5. A vector comprising the nucleic acid molecule of claim 4.

6. A host cell comprising the vector of claim 5.

7. A method of producing the peptide of any one of claims 1 to 3, comprising:
   (a) culturing the host cell of claim 6 under suitable conditions; and
   (b) isolating the peptide produced.

8. A composition comprising at least one peptide of any one of claims 1 to 3 being attached to any one of the group consisting of one or more nucleic acid molecules, one or more peptides or proteins, one or more small molecules, and one or more nanoparticles, wherein the attachment is accomplished by a linkage selected from the group consisting of a covalent linkage and a non-covalent linkage.

9. The composition of claim 8, wherein the at least one peptide is attached to one or more other peptides.

10. The composition of claim 9, wherein the one or more other peptides form at least in part in an alpha-helical secondary structure.

11. The composition of claim 9, wherein the one or more other peptides are pro-apoptotic peptides.

12. A method of producing the composition of claim 8, comprising:
   (a) providing at least one peptide of any one of claims 1 to 3; and
   (b) contacting the at least one peptide with any one of the group consisting of one or more nucleic acid molecules, one or more peptides or proteins, one or more small molecules, and one or more nanoparticles, thus allowing for forming an attachment.

13. A method of detecting the internalization behavior of the peptide of any one of claims 1 to 3 or the composition of claim 8, comprising:
   (a) administering the peptide or the composition to one or more cells; and
   (b) detecting the internalization of the peptide or the composition.

14. A pharmaceutical composition comprising at least one peptide of any one of claims 1 to 3.

15. A method for the transformation or transfection of one or more cells, comprising:
   contacting one or more cells to be transformed or transfected with at least one peptide of any one of claims 1 to 3.

16. A method for the prevention and/or treatment of a condition selected from the group consisting of cancer, immune diseases, cardiovascular diseases, neuronal diseases, infections, and inflammatory diseases, comprising:
   administering at least one peptide of any one of claims 1 to 3 to a subject suffering from any one or more of said conditions.

17. A method for the treatment of a condition selected from the group consisting of cancer, immune diseases, cardiovascular diseases, neuronal diseases, infections, and inflammatory diseases, comprising: administering at least one peptide of any one of claims 1 to 3 or the composition of claim 8 to a subject.

18. A kit comprising the peptide of any one of claims 1 to 3.

19. The peptide of claim 1, wherein the peptide has an amino acid sequence having over its total length at least 92% overall sequence identity with SEQ ID NO: 2.

20. The peptide of claim 3, wherein the peptide is of human origin.

21. The pharmaceutical compositions of claim 14, further comprising one or more pharmaceutically acceptable excipients and/or additives.

22. A peptide being in attachment to at least one nucleic acid molecule via a linkage selected from the group consisting of a covalent linkage and a non-covalent linkage, the peptide being capable of being internalized into a cell, wherein the peptide:
   (a) has an amino acid sequence selected from the group consisting of: GAAEAAARVYDLGLRRLRQRRRL-RRERVRA (SEQ ID NO: 2); and
   an amino acid sequence having over its total length at least 80% overall sequence identity with any one of SEQ ID NO: 2 to SEQ ID NO: 4; and
   (b) is internalized into a cell with an efficacy being at least 200% of the internalization efficacy of the TAT peptide having the amino acid sequence GRKKRRQRRRPPQ (SEQ ID NO: 1).

23. The peptide of claim 22, wherein the peptide has an amino acid sequence having over its total length at least 92% overall sequence identity with SEQ ID NO: 2.

24. The peptide of claim 22 or 23, wherein at least a part of the peptide forms an alpha-helical secondary structure.

25. The peptide of claim 22 or 23, wherein the peptide is of mammalian origin.

26. The peptide of claim 25, wherein the peptide is of human origin.

27. A pharmaceutical composition comprising at least one peptide of claim 22 or 23.

28. A method for the transformation or transfection of one or more cells, comprising:
  contacting one or more cells to be transformed or transfected with at least one peptide of claim 22 or 23.

29. A method for the treatment of a condition selected from the group consisting of cancer, immune diseases, cardiovascular diseases, neuronal diseases, infections, and inflammatory diseases, comprising:
  administering at least one peptide of claim 22 or 23 to a subject suffering from any one or more of said conditions.

* * * * *

SEQUENCE LISTING

<160> NUMBER OF SEQ ID NOS: 79

<210> SEQ ID NO 1
<211> LENGTH: 13
<212> TYPE: PRT
<213> ORGANISM: Human immunodeficiency virus 1
<220> FEATURE:
<223> OTHER INFORMATION: TAT peptide sequence

<400> SEQUENCE: 1

Gly Arg Lys Lys Arg Arg Gln Arg Arg Arg Pro Pro Gln
 1               5                  10

<210> SEQ ID NO 2
<211> LENGTH: 30
<212> TYPE: PRT
<213> ORGANISM: Homo sapiens
<220> FEATURE:
<223> OTHER INFORMATION: NRTN peptide sequence

<400> SEQUENCE: 2

Gly Ala Ala Glu Ala Ala Ala Arg Val Tyr Asp Leu Gly Leu Arg Arg
 1               5                  10                  15

Leu Arg Gln Arg Arg Arg Leu Arg Arg Glu Arg Val Arg Ala
            20                  25                  30

<210> SEQ ID NO 3
<211> LENGTH: 30
<212> TYPE: PRT
<213> ORGANISM: Homo sapiens
<220> FEATURE:
<223> OTHER INFORMATION: CPXM2 peptide sequence

<400> SEQUENCE: 3

Ile Arg Glu Ile Met Glu Lys Phe Gly Lys Gln Pro Val Ser Leu Pro
 1               5                  10                  15

Ala Arg Arg Leu Lys Leu Arg Gly Arg Lys Arg Arg Gln Arg
            20                  25                  30

<210> SEQ ID NO 4
<211> LENGTH: 30
<212> TYPE: PRT
<213> ORGANISM: Homo sapiens
<220> FEATURE:
<223> OTHER INFORMATION: ASM3B peptide sequence

<400> SEQUENCE: 4

Tyr Leu Lys Val Val Arg Lys His His Arg Val Ile Ala Gly Gln Phe
 1               5                  10                  15

Phe Gly His His His Thr Asp Ser Phe Arg Met Leu Tyr Asp
            20                  25                  30

<210> SEQ ID NO 5
<211> LENGTH: 30
<212> TYPE: PRT
<213> ORGANISM: Homo sapiens
<220> FEATURE:
<223> OTHER INFORMATION: FGF12 peptide sequence

<400> SEQUENCE: 5

Ser Lys Val Arg Phe Cys Ser Gly Arg Lys Arg Pro Val Arg Arg
 1               5                  10                  15

Pro Glu Pro Gln Leu Lys Gly Ile Val Thr Arg Leu Phe Ser
            20                  25                  30

<210> SEQ ID NO 6
<211> LENGTH: 30
<212> TYPE: PRT
<213> ORGANISM: Homo sapiens
<220> FEATURE:
<223> OTHER INFORMATION: CU025 peptide sequence

<400> SEQUENCE: 6

Ser Met Ser Val Leu Glu Pro Gly Thr Ala Lys Lys His Lys Gly Gly
                5                   10                  15

Ile Leu Arg Lys Gly Ala Lys Leu Phe Phe Arg Arg Arg His
            20                  25                  30

<210> SEQ ID NO 7
<211> LENGTH: 30
<212> TYPE: PRT
<213> ORGANISM: Homo sapiens
<220> FEATURE:
<223> OTHER INFORMATION: IGS10 peptide sequence

<400> SEQUENCE: 7

Gln Arg Lys Ile Gly Gly Arg Gly Arg Ile Ile Ser Pro Tyr Arg Thr
                5                   10                  15

Pro Val Leu Arg Arg His Arg Tyr Ser Ile Phe Arg Ser Thr
            20                  25                  30

<210> SEQ ID NO 8
<211> LENGTH: 30
<212> TYPE: PRT
<213> ORGANISM: Homo sapiens
<220> FEATURE:
<223> OTHER INFORMATION: CPXM peptide sequence

<400> SEQUENCE: 8

Gln His Val Arg Ile Arg Val Ile Lys Lys Lys Lys Val Ile Met Lys
                5                   10                  15

Lys Arg Lys Lys Leu Thr Leu Thr Arg Pro Thr Pro Leu Val
            20                  25                  30

<210> SEQ ID NO 9
<211> LENGTH: 30
<212> TYPE: PRT
<213> ORGANISM: Homo sapiens
<220> FEATURE:
<223> OTHER INFORMATION: CD026 peptide sequence

<400> SEQUENCE: 9

Phe His Phe Phe Pro Arg Arg Pro Arg Ile His Phe Arg Phe Pro Asn
                5                   10                  15

Arg Pro Phe Val Pro Ser Arg Cys Asn His Arg Phe Pro Phe
            20                  25                  30

<210> SEQ ID NO 10
<211> LENGTH: 39
<212> TYPE: PRT
<213> ORGANISM: Homo sapiens
<220> FEATURE:
<223> OTHER INFORMATION: FALL39 Var.1 peptide sequence

<400> SEQUENCE: 10

Phe Ala Leu Leu Gly Asp Phe Phe Arg Lys Ser Lys Glu Lys Ile Gly
                5                   10                  15

Lys Glu Phe Lys Arg Ile Val Gln Arg Ile Lys Asp Phe Leu Arg Asn
            20                  25                  30

```
Leu Val Pro Arg Thr Glu Ser
            35

<210> SEQ ID NO 11
<211> LENGTH: 10
<212> TYPE: PRT
<213> ORGANISM: Artificial sequence
<220> FEATURE:
<223> OTHER INFORMATION: Poly-Arg peptide sequence

<400> SEQUENCE: 11

Arg Arg Arg Arg Arg Arg Arg Arg Arg Arg
                5                   10

<210> SEQ ID NO 12
<211> LENGTH: 23
<212> TYPE: PRT
<213> ORGANISM: Influenza virus
<220> FEATURE:
<223> OTHER INFORMATION: INF7 peptide sequence

<400> SEQUENCE: 12

Gly Leu Phe Glu Ala Ile Glu Gly Phe Ile Glu Asn Gly Trp Glu Gly
                5                   10                  15

Met Ile Asp Gly Trp Tyr Gly
            20

<210> SEQ ID NO 13
<211> LENGTH: 17
<212> TYPE: PRT
<213> ORGANISM: Human immunodeficiency virus 1
<220> FEATURE:
<223> OTHER INFORMATION: REV peptide sequence

<400> SEQUENCE: 13

Thr Arg Gln Ala Arg Arg Asn Arg Arg Arg Arg Trp Arg Glu Arg Gln
                5                   10                  15

Arg

<210> SEQ ID NO 14
<211> LENGTH: 22
<212> TYPE: PRT
<213> ORGANISM: Homo sapiens
<220> FEATURE:
<223> OTHER INFORMATION: Trunc_protamine peptide sequence

<400> SEQUENCE: 14

Arg Ser Gln Ser Arg Ser Arg Tyr Tyr Arg Gln Arg Gln Arg Ser Arg
                5                   10                  15

Arg Arg Arg Arg Arg Ser
            20

<210> SEQ ID NO 15
<211> LENGTH: 14
<212> TYPE: PRT
<213> ORGANISM: Homo sapiens
<220> FEATURE:
<223> OTHER INFORMATION: Crotamine peptide sequence

<400> SEQUENCE: 15

Tyr Lys Gln Cys His Lys Lys Gly Gly Lys Lys Gly Ser Gly
                5                   10

<210> SEQ ID NO 16
<211> LENGTH: 17
```

```
<212> TYPE: PRT
<213> ORGANISM: Homo sapiens
<220> FEATURE:
<223> OTHER INFORMATION: MTS peptide sequence

<400> SEQUENCE: 16

Lys Gly Glu Gly Ala Ala Val Leu Leu Pro Val Leu Leu Ala Ala Pro
                5                   10                  15

Gly

<210> SEQ ID NO 17
<211> LENGTH: 34
<212> TYPE: PRT
<213> ORGANISM: Homo sapiens
<220> FEATURE:
<223> OTHER INFORMATION: Perforin_NT peptide sequence

<400> SEQUENCE: 17

Pro Ala His Thr Ala Ala Arg Ser Glu Ala Lys Arg Ser His Lys Phe
                5                   10                  15

Val Pro Gly Ala Trp Leu Ala Gly Glu Gly Val Asp Val Thr Ser Leu
            20                  25                  30

Arg Arg

<210> SEQ ID NO 18
<211> LENGTH: 38
<212> TYPE: PRT
<213> ORGANISM: Homo sapiens
<220> FEATURE:
<223> OTHER INFORMATION: BPIL (38 aa) peptide sequence

<400> SEQUENCE: 18

Val Ala Val Ala Tyr Pro Lys Ser Lys Pro Leu Thr Thr Gln Ile Lys
                5                   10                  15

Ile Lys Lys Pro Pro Lys Val Thr Met Lys Thr Gly Lys Ser Leu Leu
            20                  25                  30

His Leu His Ser Thr Leu
        35

<210> SEQ ID NO 19
<211> LENGTH: 30
<212> TYPE: PRT
<213> ORGANISM: Homo sapiens
<220> FEATURE:
<223> OTHER INFORMATION: BPIL (30 aa) peptide sequence

<400> SEQUENCE: 19

Lys Ser Lys Pro Leu Thr Thr Gln Ile Lys Ile Lys Lys Pro Pro Lys
                5                   10                  15

Val Thr Met Lys Thr Gly Lys Ser Leu Leu His Leu His Ser
            20                  25                  30

<210> SEQ ID NO 20
<211> LENGTH: 38
<212> TYPE: PRT
<213> ORGANISM: Homo sapiens
<220> FEATURE:
<223> OTHER INFORMATION: Defensin-Cons (C^I,III,V,VI -S) peptide
      sequence

<400> SEQUENCE: 20

Gly Leu Arg Arg Ser Arg Val Arg Gly Gly Arg Cys Arg Lys Ser Ser
                5                   10                  15

Lys Glu Ile Glu Arg Lys Lys Gly Lys Cys Ser Thr Arg Gly Arg Lys
```

```
                   20                  25                  30

Ser Ser Arg Arg Lys Lys
        35

<210> SEQ ID NO 21
<211> LENGTH: 38
<212> TYPE: PRT
<213> ORGANISM: Homo sapiens
<220> FEATURE:
<223> OTHER INFORMATION: LIP_Con_N peptide sequence

<400> SEQUENCE: 21

Ile Lys Lys Met Arg Arg Lys Arg Ser Ser Lys Met Tyr Leu Lys Thr
                  5                  10                  15

Arg Ala Gln Met Pro Phe Lys Val Tyr His Tyr Gln Leu Lys Ile His
                 20                  25                  30

Phe Ile Gly Tyr Lys Asn
        35

<210> SEQ ID NO 22
<211> LENGTH: 31
<212> TYPE: PRT
<213> ORGANISM: Homo sapiens
<220> FEATURE:
<223> OTHER INFORMATION: ApoL_cons_1 peptide sequence

<400> SEQUENCE: 22

Arg Glu Phe Pro Arg Leu Lys Arg Lys Leu Lys Gly His Ile Arg Lys
                  5                  10                  15

Leu Arg Ala Leu Ala Asp Asp Val Asp Lys Val His Lys Lys Phe
                 20                  25                  30

<210> SEQ ID NO 23
<211> LENGTH: 30
<212> TYPE: PRT
<213> ORGANISM: Homo sapiens
<220> FEATURE:
<223> OTHER INFORMATION: ApoL_cons_2 peptide sequence

<400> SEQUENCE: 23

Leu Arg Asn Thr Leu Lys Tyr Ala Lys Lys Val Val Arg Ala Phe Trp
                  5                  10                  15

Arg Ala Arg Ala Asn Pro Arg Leu Leu Asn Ala Thr Lys Arg
                 20                  25                  30

<210> SEQ ID NO 24
<211> LENGTH: 30
<212> TYPE: PRT
<213> ORGANISM: Homo sapiens
<220> FEATURE:
<223> OTHER INFORMATION: FAM5C peptide sequence

<400> SEQUENCE: 24

Phe Leu Lys Ala Gln Lys Ile Val His Lys Leu Phe Ser Leu Ser Lys
                  5                  10                  15

Arg Ala His Lys Gln Pro Leu Ile Ser Leu Pro Arg Gln Arg
                 20                  25                  30

<210> SEQ ID NO 25
<211> LENGTH: 30
<212> TYPE: PRT
<213> ORGANISM: Homo sapiens
<220> FEATURE:
<223> OTHER INFORMATION: FAM5B peptide sequence
```

```
<400> SEQUENCE: 25

Gln His Arg Tyr Gln Gln Leu Gly Ala Gly Leu Lys Val Leu Phe Lys
                 5                  10                  15
Lys Thr His Arg Ile Leu Arg Arg Leu Phe Asn Leu Ala Lys
             20                  25                  30

<210> SEQ ID NO 26
<211> LENGTH: 30
<212> TYPE: PRT
<213> ORGANISM: Homo sapiens
<220> FEATURE:
<223> OTHER INFORMATION: COOA1 peptide sequence

<400> SEQUENCE: 26

Met His Leu Arg Ala His Arg Thr Arg Arg Gly Lys Val Ser Pro Thr
                 5                  10                  15
Ala Lys Thr Lys Ser Leu Leu His Phe Ile Val Leu Ala Val
             20                  25                  30

<210> SEQ ID NO 27
<211> LENGTH: 30
<212> TYPE: PRT
<213> ORGANISM: Homo sapiens
<220> FEATURE:
<223> OTHER INFORMATION: MMP25 peptide sequence

<400> SEQUENCE: 27

Gly Leu Val Arg Arg Arg Arg Arg Tyr Ala Leu Ser Gly Ser Val Trp
                 5                  10                  15
Lys Lys Arg Thr Leu Thr Trp Arg Val Arg Ser Phe Pro Gln
             20                  25                  30

<210> SEQ ID NO 28
<211> LENGTH: 30
<212> TYPE: PRT
<213> ORGANISM: Homo sapiens
<220> FEATURE:
<223> OTHER INFORMATION: NETR peptide sequence

<400> SEQUENCE: 28

Arg Leu Leu His Arg Arg Gln Lys Arg Ile Ile Gly Gly Lys Asn Ser
                 5                  10                  15
Leu Arg Gly Gly Trp Pro Trp Gln Val Ser Leu Arg Leu Lys
             20                  25                  30

<210> SEQ ID NO 29
<211> LENGTH: 30
<212> TYPE: PRT
<213> ORGANISM: Homo sapiens
<220> FEATURE:
<223> OTHER INFORMATION: SCUB3 peptide sequence

<400> SEQUENCE: 29

Leu Arg Gln Arg Met Glu Arg Arg Leu Lys Gly Ser Leu Lys Met Leu
                 5                  10                  15
Arg Lys Ser Ile Asn Gln Asp Arg Phe Leu Leu Arg Leu Ala
             20                  25                  30

<210> SEQ ID NO 30
<211> LENGTH: 38
<212> TYPE: PRT
<213> ORGANISM: Homo sapiens
<220> FEATURE:
<223> OTHER INFORMATION: Defensin-Cons (C^II,III,IV,VI -S) peptide
      sequence
```

```
<400> SEQUENCE: 30

Gly Leu Arg Arg Cys Arg Val Arg Gly Gly Ser Arg Lys Ser Ser
1               5                   10                  15

Lys Glu Ile Glu Arg Lys Lys Gly Lys Ser Ser Thr Arg Gly Arg Lys
            20                  25                  30

Cys Ser Arg Arg Lys Lys
                35

<210> SEQ ID NO 31
<211> LENGTH: 30
<212> TYPE: PRT
<213> ORGANISM: Homo sapiens
<220> FEATURE:
<223> OTHER INFORMATION: Granulsin_WT peptide sequence

<400> SEQUENCE: 31

Lys Leu Lys Lys Met Val Asp Lys Pro Thr Gln Arg Ser Val Ser Asn
1               5                   10                  15

Ala Ala Thr Arg Val Ala Arg Thr Gly Arg Ser Arg Trp Arg
            20                  25                  30

<210> SEQ ID NO 32
<211> LENGTH: 29
<212> TYPE: PRT
<213> ORGANISM: Homo sapiens
<220> FEATURE:
<223> OTHER INFORMATION: Granulsin_G9 peptide sequence

<400> SEQUENCE: 32

Gln Arg Ser Val Ser Asn Ala Ala Thr Arg Val Ser Arg Thr Gly Arg
1               5                   10                  15

Ser Arg Trp Arg Asp Val Ser Arg Asn Phe Met Arg Arg
            20                  25

<210> SEQ ID NO 33
<211> LENGTH: 30
<212> TYPE: PRT
<213> ORGANISM: Homo sapiens
<220> FEATURE:
<223> OTHER INFORMATION: C06_mot2 peptide sequence

<400> SEQUENCE: 33

Ala Lys His Cys Val Arg Ile Glu Thr Lys Lys Arg Val Leu Phe Ala
1               5                   10                  15

Lys Lys Thr Lys Val Glu His Arg Cys Thr Thr Asn Lys Leu
            20                  25                  30

<210> SEQ ID NO 34
<211> LENGTH: 30
<212> TYPE: PRT
<213> ORGANISM: Homo sapiens
<220> FEATURE:
<223> OTHER INFORMATION: C06_mot1 peptide sequence

<400> SEQUENCE: 34

Ala Ser His Lys Lys Asp Ser Ser Phe Ile Arg Ile His Lys Val Met
1               5                   10                  15

Lys Val Leu Asn Phe Thr Thr Lys Ala Lys Asp Leu His Leu
            20                  25                  30

<210> SEQ ID NO 35
<211> LENGTH: 30
<212> TYPE: PRT
```

```
<213> ORGANISM: Homo sapiens
<220> FEATURE:
<223> OTHER INFORMATION: CO8_mot1 peptide sequence

<400> SEQUENCE: 35

Leu Gly Ile Ser Ser Gln Ser Asp Arg Gly Lys His Tyr Ile Arg Arg
                 5                   10                  15
Thr Lys Arg Phe Ser His Thr Lys Ser Val Phe Leu His Ala
            20                  25                  30

<210> SEQ ID NO 36
<211> LENGTH: 30
<212> TYPE: PRT
<213> ORGANISM: Homo sapiens
<220> FEATURE:
<223> OTHER INFORMATION: CO9_mot1a peptide sequence

<400> SEQUENCE: 36

Glu His Tyr Glu Glu Gln Ile Glu Ala Phe Lys Ser Ile Ile Gln Glu
                 5                   10                  15
Lys Thr Ser Asn Phe Asn Ala Ala Ile Ser Leu Lys Phe Thr
            20                  25                  30

<210> SEQ ID NO 37
<211> LENGTH: 30
<212> TYPE: PRT
<213> ORGANISM: Homo sapiens
<220> FEATURE:
<223> OTHER INFORMATION: CO9_mot1b peptide sequence

<400> SEQUENCE: 37

Leu His Gly Lys Gly Ser Phe Arg Phe Ser Tyr Ser Lys Asn Glu Thr
                 5                   10                  15
Tyr Gln Leu Phe Leu Ser Tyr Ser Ser Lys Lys Glu Lys Met
            20                  25                  30

<210> SEQ ID NO 38
<211> LENGTH: 31
<212> TYPE: PRT
<213> ORGANISM: Homo sapiens
<220> FEATURE:
<223> OTHER INFORMATION: Perforin_SC peptide sequence

<400> SEQUENCE: 38

Lys Lys Lys Lys His Lys Met Thr Ala Ser Phe His Gln Thr Tyr Arg
                 5                   10                  15
Glu Arg His Ser Glu Val Val Gly Gly His His Thr Ser Ile Asn
            20                  25                  30

<210> SEQ ID NO 39
<211> LENGTH: 31
<212> TYPE: PRT
<213> ORGANISM: Homo sapiens
<220> FEATURE:
<223> OTHER INFORMATION: Factor_H_derived peptide sequence

<400> SEQUENCE: 39

Ala Ile Asp Lys Leu Lys Lys Ala Lys Ser Ser Asn Leu Ile Ile Leu
                 5                   10                  15
Glu Glu His Lys Leu Lys Asn Lys Glu Phe Asp His Asn Ser
            20                  25                  30

<210> SEQ ID NO 40
<211> LENGTH: 48
<212> TYPE: PRT
```

-continued

```
<213> ORGANISM: Homo sapiens
<220> FEATURE:
<223> OTHER INFORMATION: LIP_Cons_C_WT peptide sequence

<400> SEQUENCE: 40

Ile Lys Lys Ile Arg Val Lys Ala Gly Glu Thr Gln Lys Lys Leu Thr
                 5                  10                  15

Phe Cys Ser Glu Asp Lys Asp Ser His Leu Ile Lys Pro Lys Arg Glu
             20                  25                  30

Lys Ile Phe Val Lys Cys Arg Asp Lys Ser Lys Met Lys Lys Arg Lys
         35                  40                  45

<210> SEQ ID NO 41
<211> LENGTH: 48
<212> TYPE: PRT
<213> ORGANISM: Homo sapiens
<220> FEATURE:
<223> OTHER INFORMATION: LIP_Cons_C_AA peptide sequence

<400> SEQUENCE: 41

Ile Lys Lys Ile Arg Val Lys Ala Gly Glu Thr Gln Lys Lys Leu Thr
                 5                  10                  15

Phe Ala Ser Glu Asp Lys Asp Ser His Leu Ile Lys Pro Lys Arg Glu
             20                  25                  30

Lys Ile Phe Val Lys Ala Arg Asp Lys Ser Lys Met Lys Lys Arg Lys
         35                  40                  45

<210> SEQ ID NO 42
<211> LENGTH: 30
<212> TYPE: PRT
<213> ORGANISM: Homo sapiens
<220> FEATURE:
<223> OTHER INFORMATION: ApoL_cons_3 peptide sequence

<400> SEQUENCE: 42

Arg Ser Lys Ser Ala Glu Glu Leu Arg Ala Lys Ala Gln Glu Leu Glu
                 5                  10                  15

Arg Lys Leu Asp Arg Leu Thr Gln His His Arg His Leu Gln
             20                  25                  30

<210> SEQ ID NO 43
<211> LENGTH: 30
<212> TYPE: PRT
<213> ORGANISM: Homo sapiens
<220> FEATURE:
<223> OTHER INFORMATION: CRSPL peptide sequence

<400> SEQUENCE: 43

Val Pro Arg Tyr Arg Arg Lys Arg His Ile Ser Val Arg Asp Met Asn
                 5                  10                  15

Ala Leu Leu Asp Tyr His Asn His Ile Arg Ala Ser Val Tyr
             20                  25                  30

<210> SEQ ID NO 44
<211> LENGTH: 30
<212> TYPE: PRT
<213> ORGANISM: Homo sapiens
<220> FEATURE:
<223> OTHER INFORMATION: ATS7 peptide sequence

<400> SEQUENCE: 44

Arg Arg Glu Arg Trp Glu Gln Arg Gln Gln Trp Arg Arg Pro Arg Leu
                 5                  10                  15

Arg Arg Leu His Gln Arg Ser Val Ser Lys Glu Lys Trp Val
```

```
                    20                  25                  30

<210> SEQ ID NO 45
<211> LENGTH: 30
<212> TYPE: PRT
<213> ORGANISM: Homo sapiens
<220> FEATURE:
<223> OTHER INFORMATION: AREG peptide sequence

<400> SEQUENCE: 45

Lys Thr Glu Ser Glu Asn Thr Ser Asp Lys Pro Lys Arg Lys Lys Lys
                    5                  10                  15

Gly Gly Lys Asn Gly Lys Asn Arg Arg Asn Arg Lys Lys Lys
                    20                  25                  30

<210> SEQ ID NO 46
<211> LENGTH: 30
<212> TYPE: PRT
<213> ORGANISM: Homo sapiens
<220> FEATURE:
<223> OTHER INFORMATION: FA20A peptide sequence

<400> SEQUENCE: 46

Gln Glu Ala Leu Arg Tyr Tyr Arg Arg Lys Val Ala Arg Trp Asn Arg
                    5                  10                  15

Arg His Lys Met Tyr Arg Glu Gln Met Asn Leu Thr Ser Leu
                    20                  25                  30

<210> SEQ ID NO 47
<211> LENGTH: 30
<212> TYPE: PRT
<213> ORGANISM: Homo sapiens
<220> FEATURE:
<223> OTHER INFORMATION: GNAS3 peptide sequence

<400> SEQUENCE: 47

Lys Glu Glu Lys Gln Arg Arg Arg Ala Lys Pro Lys Lys Pro Thr Arg
                    5                  10                  15

Arg Asp Ala Ser Pro Glu Ser Pro Ser Lys Lys Gly Pro Ile
                    20                  25                  30

<210> SEQ ID NO 48
<211> LENGTH: 30
<212> TYPE: PRT
<213> ORGANISM: Homo sapiens
<220> FEATURE:
<223> OTHER INFORMATION: PAP2 peptide sequence

<400> SEQUENCE: 48

Arg Arg Gly Trp Ala Lys Ser Arg Gln Arg Arg Gln Val Trp Lys Arg
                    5                  10                  15

Arg Ala Glu Asp Gly Gln Gly Asp Ser Gly Ile Ser Ser His
                    20                  25                  30

<210> SEQ ID NO 49
<211> LENGTH: 30
<212> TYPE: PRT
<213> ORGANISM: Homo sapiens
<220> FEATURE:
<223> OTHER INFORMATION: HISTATIN_1 peptide sequence

<400> SEQUENCE: 49

Ile Ser Ala Asp Ser His Glu Lys Arg His His Gly Tyr Arg Arg Lys
                    5                  10                  15

Phe His Glu Lys His His Ser His Arg Glu Phe Pro Phe Tyr
```

<210> SEQ ID NO 50
<211> LENGTH: 30
<212> TYPE: PRT
<213> ORGANISM: Homo sapiens
<220> FEATURE:
<223> OTHER INFORMATION: HISTATIN_3 peptide sequence

<400> SEQUENCE: 50

Ala Asp Ser His Ala Lys Arg His His Gly Tyr Lys Arg Lys Phe His
                 5                  10                  15
Glu Lys His His Ser His Arg Gly Tyr Arg Ser Asn Tyr Leu
             20                  25                  30

<210> SEQ ID NO 51
<211> LENGTH: 30
<212> TYPE: PRT
<213> ORGANISM: Homo sapiens
<220> FEATURE:
<223> OTHER INFORMATION: NPTX3 peptide sequence

<400> SEQUENCE: 51

Leu Lys Ala Trp Val Arg Lys Leu Gln Arg Arg Gly Arg Lys Val Asp
                 5                  10                  15
Thr Arg Leu Arg Ala Leu Asp Leu Thr Leu Gly Glu Arg Ser
             20                  25                  30

<210> SEQ ID NO 52
<211> LENGTH: 30
<212> TYPE: PRT
<213> ORGANISM: Homo sapiens
<220> FEATURE:
<223> OTHER INFORMATION: PROL4 peptide sequence

<400> SEQUENCE: 52

Gly His His Arg His Pro Pro Pro Pro Phe Gln Asn Gln Gln Arg
                 5                  10                  15
Pro Pro Arg Arg Gly His Arg Gln Leu Ser Leu Pro Arg Phe
             20                  25                  30

<210> SEQ ID NO 53
<211> LENGTH: 30
<212> TYPE: PRT
<213> ORGANISM: Homo sapiens
<220> FEATURE:
<223> OTHER INFORMATION: YC002 peptide sequence

<400> SEQUENCE: 53

Gly Ser Arg Pro Arg His Leu Leu Ser Glu Arg Ser Arg Arg Ser Gly
                 5                  10                  15
Arg Gly Trp Pro Arg Pro Arg Ala Ala Tyr Arg Ala Leu Leu
             20                  25                  30

<210> SEQ ID NO 54
<211> LENGTH: 30
<212> TYPE: PRT
<213> ORGANISM: Homo sapiens
<220> FEATURE:
<223> OTHER INFORMATION: CD029 peptide sequence

<400> SEQUENCE: 54

Lys Tyr Arg Pro Val Ala Ile His Leu Ala Gly Thr Gly Asp His His
                 5                  10                  15
Tyr Trp Arg Arg Arg Thr Leu Met Ala Arg Pro Met Ile Lys

```
<210> SEQ ID NO 55
<211> LENGTH: 30
<212> TYPE: PRT
<213> ORGANISM: Homo sapiens
<220> FEATURE:
<223> OTHER INFORMATION: TOR2 peptide sequence

<400> SEQUENCE: 55

Ser Pro Arg Val His His Phe Ser Pro Val Leu His Phe Pro His Pro
                 5                  10                  15

Ser His Ile Glu Arg Tyr Lys Lys Asp Leu Lys Ser Trp Val
            20                  25                  30

<210> SEQ ID NO 56
<211> LENGTH: 30
<212> TYPE: PRT
<213> ORGANISM: Homo sapiens
<220> FEATURE:
<223> OTHER INFORMATION: CO4AB peptide sequence

<400> SEQUENCE: 56

Gly Arg Arg Asn Arg Arg Arg Glu Ala Pro Lys Val Val Glu Glu
                 5                  10                  15

Gln Glu Ser Arg Val His Tyr Thr Val Ala Ile Trp Arg Asn
            20                  25                  30

<210> SEQ ID NO 57
<211> LENGTH: 30
<212> TYPE: PRT
<213> ORGANISM: Homo sapiens
<220> FEATURE:
<223> OTHER INFORMATION: SULF1 peptide sequence

<400> SEQUENCE: 57

Phe Lys Glu Ala Ala Gln Glu Val Asp Ser Lys Leu Gln Leu Phe Lys
                 5                  10                  15

Glu Asn Asn Arg Arg Arg Lys Lys Glu Arg Lys Glu Lys Arg
            20                  25                  30

<210> SEQ ID NO 58
<211> LENGTH: 30
<212> TYPE: PRT
<213> ORGANISM: Homo sapiens
<220> FEATURE:
<223> OTHER INFORMATION: PROK2 peptide sequence

<400> SEQUENCE: 58

Leu Thr Arg Lys Asn Asn Phe Gly Asn Gly Arg Gln Glu Arg Arg Lys
                 5                  10                  15

Arg Lys Arg Ser Lys Arg Lys Lys Glu Val Pro Phe Phe Gly
            20                  25                  30

<210> SEQ ID NO 59
<211> LENGTH: 30
<212> TYPE: PRT
<213> ORGANISM: Homo sapiens
<220> FEATURE:
<223> OTHER INFORMATION: WNT16 peptide sequence

<400> SEQUENCE: 59

Ile Gln Ile Ser Asp Lys Thr Lys Arg Lys Met Arg Arg Arg Glu Lys
                 5                  10                  15

Asp Gln Arg Lys Ile Pro Ile His Lys Asp Asp Leu Leu Tyr
```

<210> SEQ ID NO 60
<211> LENGTH: 30
<212> TYPE: PRT
<213> ORGANISM: Homo sapiens
<220> FEATURE:
<223> OTHER INFORMATION: GRAK peptide sequence

<400> SEQUENCE: 60

Leu Val Lys Leu Gln Thr Ala Ala Lys Leu Asn Lys His Val Lys Met
                 5                  10                  15
Leu His Ile Arg Ser Lys Thr Ser Leu Arg Ser Gly Thr Lys
            20                  25                  30

<210> SEQ ID NO 61
<211> LENGTH: 30
<212> TYPE: PRT
<213> ORGANISM: Homo sapiens
<220> FEATURE:
<223> OTHER INFORMATION: APLD1 peptide sequence

<400> SEQUENCE: 61

Asp Ala Leu Arg Arg Phe Gln Gly Leu Leu Asp Arg Arg Gly Arg
                 5                  10                  15
Leu His Gly Gln Val Leu Arg Leu Arg Glu Val Ala Arg Arg
            20                  25                  30

<210> SEQ ID NO 62
<211> LENGTH: 30
<212> TYPE: PRT
<213> ORGANISM: Homo sapiens
<220> FEATURE:
<223> OTHER INFORMATION: CBPN peptide sequence

<400> SEQUENCE: 62

Val Asn Phe His Leu Lys Arg Ser Ile Pro Gln Val Ser Pro Val Arg
                 5                  10                  15
Arg Ala Pro Ser Arg Arg His Gly Val Arg Ala Lys Val Gln
            20                  25                  30

<210> SEQ ID NO 63
<211> LENGTH: 30
<212> TYPE: PRT
<213> ORGANISM: Homo sapiens
<220> FEATURE:
<223> OTHER INFORMATION: CFAI peptide sequence

<400> SEQUENCE: 63

Ala Glu Arg Arg Arg Ile Lys Ser Leu Leu Pro Lys Leu Ser Cys Gly
                 5                  10                  15
Val Lys Asn Arg Met His Ile Arg Arg Lys Arg Ile Val Gly
            20                  25                  30

<210> SEQ ID NO 64
<211> LENGTH: 30
<212> TYPE: PRT
<213> ORGANISM: Homo sapiens
<220> FEATURE:
<223> OTHER INFORMATION: FGF5 peptide sequence

<400> SEQUENCE: 64

Val Ala Leu Asn Lys Arg Gly Lys Ala Lys Arg Gly Cys Ser Pro Arg
                 5                  10                  15
Val Lys Pro Gln His Ile Ser Thr His Phe Leu Pro Arg Phe

```
                        20                  25                  30

<210> SEQ ID NO 65
<211> LENGTH: 30
<212> TYPE: PRT
<213> ORGANISM: Homo sapiens
<220> FEATURE:
<223> OTHER INFORMATION: LTB1L peptide sequence

<400> SEQUENCE: 65

Thr Val Ser Gly Val His Arg Arg Pro Ile His His Val Gly
                 5                  10                  15

Lys Gly Pro Val Phe Val Lys Pro Lys Asn Thr Gln Pro Val
        20                  25                  30

<210> SEQ ID NO 66
<211> LENGTH: 30
<212> TYPE: PRT
<213> ORGANISM: Homo sapiens
<220> FEATURE:
<223> OTHER INFORMATION: LFTY1 peptide sequence

<400> SEQUENCE: 66

Val Pro Lys Ala Ala Leu His Arg His Gly Arg Leu Ser Pro Arg Ser
                 5                  10                  15

Ala Arg Ala Arg Val Thr Val Glu Trp Leu Arg Val Arg Asp
        20                  25                  30

<210> SEQ ID NO 67
<211> LENGTH: 30
<212> TYPE: PRT
<213> ORGANISM: Homo sapiens
<220> FEATURE:
<223> OTHER INFORMATION: LOXL3 peptide sequence

<400> SEQUENCE: 67

Gly His Arg Arg Leu Leu Arg Phe Ser Ser Gln Ile His Asn Leu Gly
                 5                  10                  15

Arg Ala Asp Phe Arg Pro Lys Ala Gly Arg His Ser Trp Val
        20                  25                  30

<210> SEQ ID NO 68
<211> LENGTH: 30
<212> TYPE: PRT
<213> ORGANISM: Homo sapiens
<220> FEATURE:
<223> OTHER INFORMATION: PONL peptide sequence

<400> SEQUENCE: 68

Arg Leu Ala Ser Ala Arg Val His His Arg Ala Phe Arg Leu Arg
                 5                  10                  15

Ala Leu Arg Ser Leu Asp Leu Ala Gly Asn Gln Leu Thr Arg
        20                  25                  30

<210> SEQ ID NO 69
<211> LENGTH: 30
<212> TYPE: PRT
<213> ORGANISM: Homo sapiens
<220> FEATURE:
<223> OTHER INFORMATION: PRS23 peptide sequence

<400> SEQUENCE: 69

Leu Lys Lys Pro His Lys Arg Lys Phe Met Lys Ile Gly Val Ser Pro
                 5                  10                  15

Pro Ala Lys Gln Leu Pro Gly Gly Arg Ile His Phe Ser Gly
```

```
                        20                  25                  30

<210> SEQ ID NO 70
<211> LENGTH: 21
<212> TYPE: PRT
<213> ORGANISM: Homo sapiens
<220> FEATURE:
<223> OTHER INFORMATION: Nor1 peptide sequence

<400> SEQUENCE: 70

Gly Asp Trp Ile Asp Ser Ile Leu Ala Phe Ser Arg Ser Leu His Ser
  1               5                  10                  15

Leu Leu Val Asp Leu
            20

<210> SEQ ID NO 71
<211> LENGTH: 21
<212> TYPE: PRT
<213> ORGANISM: Homo sapiens
<220> FEATURE:
<223> OTHER INFORMATION: Nur77 peptide sequence

<400> SEQUENCE: 71

Gly Glu Trp Leu Asp Ser Ile Lys Asp Phe Ser Leu Asn Leu Gln Ser
  1               5                  10                  15

Leu Asn Leu Asp Ile
            20

<210> SEQ ID NO 72
<211> LENGTH: 12
<212> TYPE: PRT
<213> ORGANISM: Homo sapiens
<220> FEATURE:
<223> OTHER INFORMATION: C-terminal Nor1 peptide sequence

<400> SEQUENCE: 72

Phe Ser Arg Ser Leu His Ser Leu Leu Val Asp Leu
  1               5                  10

<210> SEQ ID NO 73
<211> LENGTH: 30
<212> TYPE: PRT
<213> ORGANISM: Artificial sequence
<220> FEATURE:
<223> OTHER INFORMATION: NurNRTN peptide sequence

<400> SEQUENCE: 73

Phe Ser Arg Ser Leu His Ser Leu Leu Tyr Asp Leu Gly Leu Arg Arg
  1               5                  10                  15

Leu Arg Gln Arg Arg Leu Arg Arg Glu Arg Val Arg Ala
            20                  25                  30

<210> SEQ ID NO 74
<211> LENGTH: 20
<212> TYPE: PRT
<213> ORGANISM: Homo sapiens
<220> FEATURE:
<223> OTHER INFORMATION: 4E-BP1 peptide sequence

<400> SEQUENCE: 74

Gly Thr Arg Ile Ile Tyr Asp Arg Lys Phe Leu Met Glu Cys Arg Asn
  1               5                  10                  15

Ser Pro Val Thr
            20
```

```
<210> SEQ ID NO 75
<211> LENGTH: 20
<212> TYPE: PRT
<213> ORGANISM: Artificial sequence
<220> FEATURE:
<223> OTHER INFORMATION: inactive 4E-BP1 peptide sequence

<400> SEQUENCE: 75

Gly Thr Arg Ile Ile Gly Asp Gly Lys Phe Gly Met Glu Cys Arg Asn
                 5                  10                  15
Ser Pro Val Thr
            20

<210> SEQ ID NO 76
<211> LENGTH: 31
<212> TYPE: PRT
<213> ORGANISM: Artificial sequence
<220> FEATURE:
<223> OTHER INFORMATION: TAT4E-BP1 peptide sequence

<400> SEQUENCE: 76

Tyr Gly Arg Lys Lys Arg Arg Gln Arg Arg Gly Thr Arg Ile Ile
                 5                  10                  15
Tyr Asp Arg Lys Phe Leu Met Glu Cys Arg Asn Ser Pro Val Thr
        20                  25                  30

<210> SEQ ID NO 77
<211> LENGTH: 31
<212> TYPE: PRT
<213> ORGANISM: Artificial sequence
<220> FEATURE:
<223> OTHER INFORMATION: inactive TAT4E-BP1 peptide sequence

<400> SEQUENCE: 77

Tyr Gly Arg Lys Lys Arg Arg Gln Arg Arg Gly Thr Arg Ile Ile
                 5                  10                  15
Gly Asp Gly Lys Phe Gly Met Glu Cys Arg Asn Ser Pro Val Thr
        20                  25                  30

<210> SEQ ID NO 78
<211> LENGTH: 50
<212> TYPE: PRT
<213> ORGANISM: Artificial sequence
<220> FEATURE:
<223> OTHER INFORMATION: NRTN4E-BP1 peptide sequence

<400> SEQUENCE: 78

Gly Ala Ala Glu Ala Ala Ala Arg Val Tyr Asp Leu Gly Leu Arg Arg
                 5                  10                  15
Leu Arg Gln Arg Arg Arg Leu Arg Arg Glu Arg Val Arg Ala Gly Thr
            20                  25                  30
Arg Ile Ile Tyr Asp Arg Lys Phe Leu Met Glu Cys Arg Asn Ser Pro
        35                  40                  45
Val Thr
    50

<210> SEQ ID NO 79
<211> LENGTH: 50
<212> TYPE: PRT
<213> ORGANISM: Artificial sequence
<220> FEATURE:
<223> OTHER INFORMATION: inactive NRTN4E-BP1 peptide sequence

<400> SEQUENCE: 79

Gly Ala Ala Glu Ala Ala Ala Arg Val Tyr Asp Leu Gly Leu Arg Arg
```

```
                  5                  10                 15
Leu Arg Gln Arg Arg Arg Leu Arg Arg Glu Arg Val Arg Ala Gly Thr
            20                  25                  30

Arg Ile Ile Gly Asp Gly Lys Phe Gly Met Glu Cys Arg Asn Ser Pro
        35                  40                  45

Val Thr
    50
```